US006391566B1

(12) United States Patent
Foldes et al.

(10) Patent No.: US 6,391,566 B1
(45) Date of Patent: May 21, 2002

(54) IONOTROPIC HUMAN GLUTAMATE RECEPTOR SUBUNIT NR3

(75) Inventors: Robert L. Foldes, Willowdale; Sally-Lin Adams, Toronto; Rajender Kamboj, Mississauga, all of (CA)

(73) Assignee: NPS Allelix Corporation, Ontario (CA)

( * ) Notice: Subject to any disclaimer, the term of this patent is extended or adjusted under 35 U.S.C. 154(b) by 0 days.

(21) Appl. No.: 08/264,578

(22) Filed: Jun. 23, 1994

Related U.S. Application Data

(63) Continuation-in-part of application No. 07/987,953, filed on Dec. 11, 1992, now abandoned.

(51) Int. Cl.$^7$ ............................................. G01N 33/567
(52) U.S. Cl. ................... 435/7.2; 435/7.1; 435/69.1; 435/252.3; 435/320.1; 536/23.5
(58) Field of Search ........................... 435/6, 7.2, 69.1, 435/252.3, 220.1; 430/7.21; 536/23.5

(56) References Cited

FOREIGN PATENT DOCUMENTS

| WO | WO 91/06648 | 5/1991 |
| WO | WO 93/25679 | 12/1993 |
| WO | WO 94/11501 | 5/1994 |

OTHER PUBLICATIONS

Puckett et al., *P.N.A.S.* 88:7557–7561, Sep. 1991.*
Schofield et al., *FEBS Letters* 244 (2):361–364, Feb. 1989.*
Grenningloh et al, *EMBO J.* 9(3):771–776, Sep. 1990.*
Nakanishi, *Science* 258:597–603, Oct. 23, 1982.*
Sugihara et al *Biochem. Biophyl. Res. Comm.* 185 (3):826–832, Jun. 30, 1992.*
Barnett et al., "Rapid Generation of DNA Fragments by PCR Amplification of Crude, Synthetic, Oligonucleotides", Nucleic Acids Research, vol. 18, No. 18, No. 10, p. 3094 (1990).
Moriyoshi et al., "Molecular Cloning and Characterization of the Rate NMDA Receptor," Nature, vol. 354, pp. 31–36 (Nov. 1991).
Meguro et al., "Functional Characterization of a Heteromeric NMDA Receptor Channels Expressed from Cloned cDNAs," Nature, vol. 357, pp. 70–74 (May 1992).
Yamazaki et al., "Cloning, Expression and Modulation of a Mouse NMDA Receptor Subunit," FEBS Letters, vol. 300, No. 1, pp. 39–45 (Mar. 1992).
Sakimura et al., "Primary Structure and Expression of the $_y$2 Subunit of the Glutamate Receptor Channel Selective for Kainate," Neuron, vol. 8, pp. 267–274 (Feb. 1992).
Monyer et al., "Heteromeric NMDA Receptors: Molecular and Functional Distinction of Subtypes," Science, vol. 256, pp. 1217 (May 1992).
Anantharan et al., "Combinatorial RNA Splicing Alters the Surface Charge on the NMDA Receptor," FEBS Letters, vol. 305, No. 1, pp. 27–30 (Jun. 1992).

Sugihara et al., "Structures and Properties of Seven Isoforms of the NMDA Receptor Generated by Alternative Splicing," Biochemical and Biophysical Research Communications, vol. 185, No. 3, pp. 826–832 (Jun. 1992).
Kutsuwada et al., "Molecular Diversity of the NMDA Receptor Channel," Nature, vol. 358, pp. 36–41 (Jul. 1992).
Oksenberg et al., "A Single Amino–Acid Difference Confers Major Pharmacological Variation between Human and Rodent 5–HT$_{1B}$ Receptors," Nature, vol. 360, pp. 161–163 (Nov. 1992).
Durand et al., "Cloning of an Apparent Splice Variant of the Rat N–methyl–D–aspartate Receptor NMDAR1 with Altered Sensitivity to Polyamines and Activators of Protein Kinase C," Proc. Natl. Acad. Sci. USA, vol. 89, pp. 9359–9363 (Oct. 1992).
Nakanishi et al., Alternative Splicing Generates Functionally Distinct N–Methyl–D Asparate Receptors., Proc. Natl. Acad. Sci. USA, vol. 89, Sep. 1992, pp. 8552–8556.
Hall et al., "Receptor Subtypes or Species Homologues: Relevance to Discovery", Elsevier Science Publishers, Ltd., 1993, pp. 1–10.
Hollmann et al., "Zinc Potentiates Agonist–Induced Currents at Certain Splice Variants of the NMDA Receptor", Neuron, vol. 10, May 1993, pp. 943–954.
Hollmann et al., "Cloning by Functional Expression of a Member of the Glutamate Receptor Family", Nature, vol. 342, Dec. 1989, pp. 643–648.
Ikeda et al., "Cloning and Expression of the $\epsilon$4 Subunit of the NMDA Receptor Channel", Federation of European Biochemical Societies, vol. 313, No. 1, Nov. 1992, pp. 34–38.
Ishii et al., "Molecular Characterization of the Family of the N–Methyl–Asparate Receptor Subunits*", The Journal of Biological Chemistry, vol. 268, No. 4, Feb. 1993, pp. 2836–2843.
Kusiak et al., "A Splice Variant of the N–Methyl–D–Aspartate (NMDAR1) Receptor", Molecular Brain Research, 20, 1993, pp. 64–70.

* cited by examiner

Primary Examiner—John Ulm
(74) Attorney, Agent, or Firm—Foley & Lardner

(57) ABSTRACT

Neurotransmission by excitatory amino acids (EAAs) such as glutamate is mediated via membrane-bound surface receptors. This neurotransmission has been found to be modulated by certain modulatory proteins. DNA coding for a family of such modulatory proteins has now been isolated and the modulatory proteins have been characterized. Herein described are recombinant cell lines which produce these modulatory proteins as heterologous membrane-bound products. Also described are related aspects of the invention, which are of commercial significance, including the use of cell lines which express the modulatory proteins either homomerically, or hotoromorically in a complex with an NMDA receptor, as a tool for discovery of compounds which affect the function of the modulatory proteins.

3 Claims, 41 Drawing Sheets

FIG. 1A

Figure 2B:
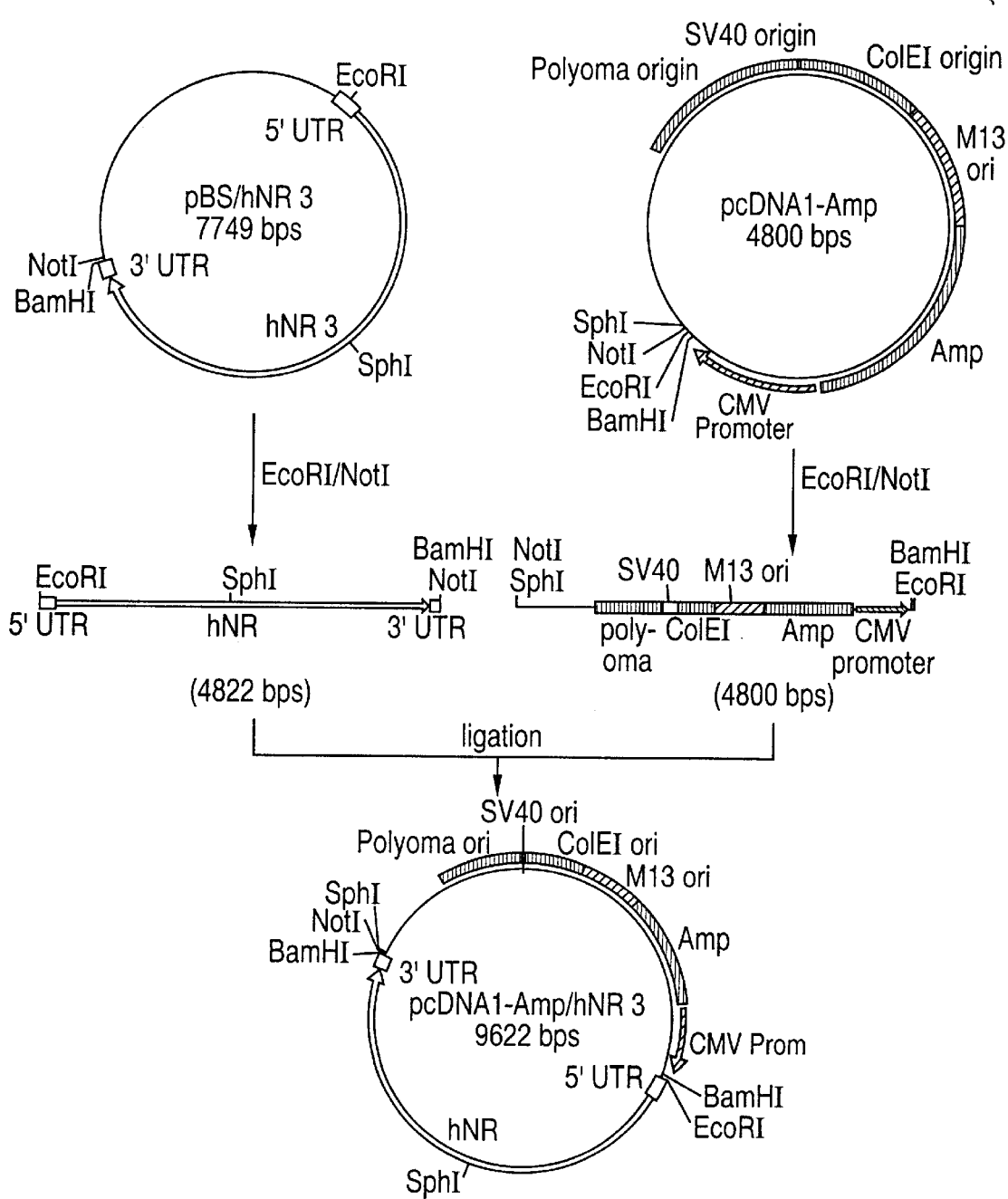

```
     Eco RI
       ↓
       GAATTCCTTTGAATTTGCATCTCTTCAAGACACAAGATTAAAACAAAATTTACGCTAAAT
  1    ----------+---------+---------+---------+---------+---------+   60
       CTTAAGGAAACTTAAACGTAGAGAAGTTCTGTGTTCTAATTTTGTTTTAAATGCGATTTA

TGGATTTTAAATTATCTTCCGTTCATTTATCCTTCGTCTTTCTTATGTGGATATGCAAGC
 61    ----------+---------+---------+---------+---------+---------+  120
       ACCTAAAATTTAATAGAAGGCAAGTAAATAGGAAGCAGAAAGAATACACCTATACGTTCG

GAGAAGAAGGGACTGGACATTCCCAACATGCTCACTCCCTTAATCTGTCCGTCTAGAGGT
121    ----------+---------+---------+---------+---------+---------+  180
       CTCTTCTTCCCTGACCTGTAAGGGTTGTACGAGTGAGGGAATTAGACAGGCAGATCTCCA

1                                           M  K  P  R  A  E  C  C    8
       TTGGCTTCTACAAACCAAGGGAGTCGACGAGTTGAAGATGAAGCCCAGAGCGGAGTGCTG
181    ----------+---------+---------+---------+---------+---------+  240
       AACCGAAGATGTTTGGTTCCCTCAGCTGCTCAACTTCTACTTCGGGTCTCGCCTCACGAC

9     S  P  K  F  W  L  V  L  A  V  L  A  V  S  G  S  R  A  R  S    28
       TTCTCCCAAGTTCTGGTTGGTGTTGGCCGTCCTGGCCGTGTCAGGCAGCAGAGCTCGTTC
241    ----------+---------+---------+---------+---------+---------+  300
       AAGAGGGTTCAAGACCAACCACAACCGGCAGGACCGGCACAGTCCGTCGTCTCGAGCAAG

29     Q  K  S  P  P  S  I  G  I  A  V  I  L  V  G  T  S  D  E  V    48
       TCAGAAGAGCCCCCCCAGCATTGGCATTGCTGTCATCCTCGTGGGCACTTCCGACGAGGT
301    ----------+---------+---------+---------+---------+---------+  360
       AGTCTTCTCGGGGGGGTCGTAACCGTAACGACAGTAGGAGCACCCGTGAAGGCTGCTCCA
```

FIG. 1B

```
 49  A  I  K  D  A  H  E  K  D  D  F  H  H  L  S  V  V  P  R  V   68
     GGCCATCAAGGATGCCCACGAGAAAGATGATTTCCACCATCTCTCCGTGGTACCCCGGGT
361  ----------+----------+----------+----------+----------+----------+ 420
     CCGGTAGTTCCTACGGGTGCTCTTTCTACTAAAGGTGGTAGAGAGGCACCATGGGGCCCA

69  E  L  V  A  M  N  E  T  D  P  K  S  I  I  T  R  I  C  D  L   88
     GGAACTGGTAGCCATGAATGAGACCGACCCAAAGAGCATCATCACCCGCATCTGTGATCT
421  ----------+----------+----------+----------+----------+----------+ 480
     CCTTGACCATCGGTACTTACTCTGGCTGGGTTTCTCGTAGTAGTGGGCGTAGACACTAGA

89  M  S  D  R  K  I  Q  G  V  V  F  A  D  D  T  D  Q  E  A  I  108
     CATGTCTGACCGGAAGATCCAGGGGGTGGTGTTTGCTGATGACACAGACCAGGAAGCCAT
481  ----------+----------+----------+----------+----------+----------+ 540
     GTACAGACTGGCCTTCTAGGTCCCCCACCACAAACGACTACTGTGTCTGGTCCTTCGGTA

109  A  Q  I  L  D  F  I  S  A  Q  T  L  T  P  I  L  G  I  H  G  128
     CGCCCAGATCCTCGATTTCATTTCAGCACAGACTCTCACCCCGATCCTGGGCATCCACGG
541  ----------+----------+----------+----------+----------+----------+ 600
     GCGGGTCTAGGAGCTAAAGTAAAGTCGTGTCTGAGAGTGGGGCTAGGACCCGTAGGTGCC

129  G  S  S  M  I  M  A  D  K  D  E  S  S  M  F  F  Q  F  G  P  148
     GGGCTCCTCTATGATAATGGCAGATAAGGATGAATCCTCCATGTTCTTCCAGTTTGGCCC
601  ----------+----------+----------+----------+----------+----------+ 660
     CCCGAGGAGATACTATTACCGTCTATTCCTACTTAGGAGGTACAAGAAGGTCAAACCGGG

149  S  I  E  Q  Q  A  S  V  M  L  N  I  M  E  E  Y  D  W  Y  I  168
     ATCAATTGAACAGCAAGCTTCCGTAATGCTCAACATCATGGAAGAATATGACTGGTACAT
661  ----------+----------+----------+----------+----------+----------+ 720
     TAGTTAACTTGTCGTTCGAAGGCATTACGAGTTGTAGTACCTTCTTATACTGACCATGTA
```

FIG. IC

```
169  F  S  I  V  T  T  Y  F  P  G  Y  Q  D  F  V  N  K  I  R  S   188
     CTTTTCTATCGTCACCACCTATTTCCCTGGCTACCAGGACTTTGTAAACAAGATCCGCAG
721  ----------+----------+----------+----------+----------+----------+   780
     GAAAAGATAGCAGTGGTGGATAAAGGGACCGATGGTCCTGAAACATTTGTTCTAGGCGTC

189  T  I  E  N  S  F  V  G  W  E  L  E  E  V  L  L  L  D  M  S   208
     CACCATTGAGAATAGCTTTGTGGGCTGGGAGCTAGAGGAGGTCCTCCTACTGGACATGTC
781  ----------+----------+----------+----------+----------+----------+   840
     GTGGTAACTCTTATCGAAACACCCGACCCTCGATCTCCTCCAGGAGGATGACCTGTACAG

209  L  D  D  G  D  S  K  I  Q  N  Q  L  K  K  L  Q  S  P  I  I   228
     CCTGGACGATGGAGATTCTAAGATCCAGAATCAGCTCAAGAAACTTCAAAGCCCCATCAT
841  ----------+----------+----------+----------+----------+----------+   900
     GGACCTGCTACCTCTAAGATTCTAGGTCTTAGTCGAGTTCTTTGAAGTTTCGGGGTAGTA

229  L  L  Y  C  T  K  E  E  A  T  Y  I  F  E  V  A  N  S  V  G   248
     TCTTCTTTACTGTACCAAGGAAGAAGCCACCTACATCTTTGAAGTGGCCAACTCAGTAGG
901  ----------+----------+----------+----------+----------+----------+   960
     AGAAGAAATGACATGGTTCCTTCTTCGGTGGATGTAGAAACTTCACCGGTTGAGTCATCC

249  L  T  G  Y  G  Y  T  W  I  V  P  S  L  V  A  G  D  T  D  T   268
     GCTGACTGGCTATGGCTACACGTGGATCGTGCCCAGTCTGGTGGCAGGGGATACAGACAC
961  ----------+----------+----------+----------+----------+----------+   1020
     CGACTGACCGATACCGATGTGCACCTAGCACGGGTCAGACCACCGTCCCCTATGTCTGTG

269  V  P  A  E  F  P  T  G  L  I  S  V  S  Y  D  E  W  D  Y  G   288
     AGTGCCTGCGGAGTTCCCCACTGGGCTCATCTCTGTATCATATGATGAATGGGACTATGG
1021 ----------+----------+----------+----------+----------+----------+   1080
     TCACGGACGCCTCAAGGGGTGACCCGAGTAGAGACATAGTATACTACTTACCCTGATACC
```

FIG. 1D

```
289  L  P  A  R  V  R  D  G  I  A  I  I  T  T  A  A  S  D  M  L  308
     CCTCCCCGCCAGAGTGAGAGATGGAATTGCCATAATCACCACTGCTGCTTCTGACATGCT
1081 ----------+---------+---------+---------+---------+---------+ 1140
     GGAGGGGCGGTCTCACTCTCTACCTTAACGGTATTAGTGGTGACGACGAAGACTGTACGA

309  S  E  H  S  F  I  P  E  P  K  S  S  C  Y  N  T  H  E  K  R  328
     GTCTGAGCACAGCTTCATCCCTGAGCCCAAAAGCAGTTGTTACAACACCCACGAGAAGAG
1141 ----------+---------+---------+---------+---------+---------+ 1200
     CAGACTCGTGTCGAAGTAGGGACTCGGGTTTTCGTCAACAATGTTGTGGGTGCTCTTCTC

329  I  Y  Q  S  N  M  L  N  R  Y  L  I  N  V  T  F  E  G  R  N  348
     AATCTACCAGTCCAATATGCTAAATAGGTATCTGATCAATGTCACTTTTGAGGGGAGGAA
1201 ----------+---------+---------+---------+---------+---------+ 1260
     TTAGATGGTCAGGTTATACGATTTATCCATAGACTAGTTACAGTGAAAACTCCCCTCCTT

349  L  S  F  S  E  D  G  Y  Q  M  H  P  K  L  V  I  I  L  L  N  368
     TTTGTCCTTCAGTGAAGATGGCTACCAGATGCACCCGAAACTGGTGATAATTCTTCTGAA
1261 ----------+---------+---------+---------+---------+---------+ 1320
     AAACAGGAAGTCACTTCTACCGATGGTCTACGTGGGCTTTGACCACTATTAAGAAGACTT

369  K  E  R  K  W  E  R  V  G  K  W  K  D  K  S  L  Q  M  K  Y  388
     CAAGGAGAGGAAGTGGGAAAGGGTGGGGAAGTGGAAAGACAAGTCCCTGCAGATGAAGTA
1321 ----------+---------+---------+---------+---------+---------+ 1380
     GTTCCTCTCCTTCACCCTTTCCCACCCCTTCACCTTTCTGTTCAGGGACGTCTACTTCAT

389  Y  V  W  P  R  M  C  P  E  T  E  E  Q  E  D  D  H  L  S  I  408
     CTATGTGTGGCCCCGAATGTGTCCAGAGACTGAAGAGCAGGAGGATGACCATCTGAGCAT
1381 ----------+---------+---------+---------+---------+---------+ 1440
     GATACACACCGGGGCTTACACAGGTCTCTGACTTCTCGTCCTCCTACTGGTAGACTCGTA
```

FIG. IE

```
409  V  T  L  E  E  A  P  F  V  I  V  E  S  V  D  P  L  S  G  T  428
     TGTGACCCTGGAGGAGGCACCATTTGTCATTGTGGAAAGTGTGGACCCTCTGAGTGGAAC
1441 ----------+----------+----------+----------+----------+---------+ 1500
     ACACTGGGACCTCCTCCGTGGTAAACAGTAACACCTTTCACACCTGGGAGACTCACCTTG

429  C  M  R  N  T  V  P  C  Q  K  R  I  V  T  E  N  K  T  D  E  448
     CTGCATGAGGAACACAGTCCCCTGCCAAAAACGCATAGTCACTGAGAATAAAACAGACGA
1501 ----------+----------+----------+----------+----------+---------+ 1560
     GACGTACTCCTTGTGTCAGGGGACGGTTTTTGCGTATCAGTGACTCTTATTTTGTCTGCT

449  E  P  G  Y  I  K  K  C  C  K  G  F  C  I  D  I  L  K  K  I  468
     GGAGCCGGGTTACATCAAAAAATGCTGCAAGGGGTTCTGTATTGACATCCTTAAGAAAAT
1561 ----------+----------+----------+----------+----------+---------+ 1620
     CCTCGGCCCAATGTAGTTTTTTACGACGTTCCCCAAGACATAACTGTAGGAATTCTTTTA

469  S  K  S  V  K  F  T  Y  D  L  Y  L  V  T  N  G  K  H  G  K  488
     TTCTAAATCTGTGAAGTTCACCTATGACCTTTACCTGGTTACCAATGGCAAGCATGGGAA
1621 ----------+----------+----------+----------+----------+---------+ 1680
     AAGATTTAGACACTTCAAGTGGATACTGGAAATGGACCAATGGTTACCGTTCGTACCCTT

489  K  I  N  G  T  W  N  G  M  I  G  E  V  V  M  K  R  A  Y  M  508
     GAAAATCAATGGAACCTGGAATGGTATGATTGGAGAGGTGGTCATGAAGAGGGCCTACAT
1681 ----------+----------+----------+----------+----------+---------+ 1740
     CTTTTAGTTACCTTGGACCTTACCATACTAACCTCTCCACCAGTACTTCTCCCGGATGTA

509  A  V  G  S  L  T  I  N  E  E  R  S  E  V  V  D  F  S  V  P  528
     GGCAGTGGGCTCACTCACCATCAATGAGGAACGATCGGAGGTGGTCGACTTCTCTGTGCC
1741 ----------+----------+----------+----------+----------+---------+ 1800
     CCGTCACCCGAGTGAGTGGTAGTTACTCCTTGCTAGCCTCCACCAGCTGAAGAGACACGG
```

FIG. 1F

```
529   F  I  E  T  G  I  S  V  M  V  S  R  S  N  G  T  V  S  P  S   548
      CTTCATAGAGACAGGCATCAGTGTCATGGTGTCACGCAGCAATGGGACTGTCTCACCTTC
1801  ----------+---------+---------+---------+---------+---------+  1860
      GAAGTATCTCTGTCCGTAGTCACAGTACCACAGTGCGTCGTTACCCTGACAGAGTGGAAG

549   A  F  L  E  P  F  S  A  D  V  W  V  M  M  F  V  M  L  L  I   568
      TGCCTTCTTAGAGCCATTCAGCGCTGACGTATGGGTGATGATGTTTGTGATGCTGCTCAT
1861  ----------+---------+---------+---------+---------+---------+  1920
      ACGGAAGAATCTCGGTAAGTCGCGACTGCATACCCACTACTACAAACACTACGACGAGTA

569   V  S  A  V  A  V  F  V  F  E  Y  F  S  P  V  G  Y  N  R  C   588
      CGTCTCAGCCGTGGCTGTCTTTGTCTTTGAGTACTTCAGCCCTGTGGGTTATAACAGGTG
1921  ----------+---------+---------+---------+---------+---------+  1980
      GCAGAGTCGGCACCGACAGAAACAGAAACTCATGAAGTCGGGACACCCAATATTGTCCAC

589   L  A  D  G  R  E  P  G  G  P  S  F  T  I  G  K  A  I  W  L   608
      CCTCGCTGATGGCAGAGAGCCTGGTGGACCCTCTTTCACCATCGGCAAAGCTATTTGGTT
1981  ----------+---------+---------+---------+---------+---------+  2040
      GGAGCGACTACCGTCTCTCGGACCACCTGGGAGAAAGTGGTAGCCGTTTCGATAAACCAA

609   L  W  G  L  V  F  N  N  S  V  P  V  Q  N  P  K  G  T  T  S   628
      GCTCTGGGGTCTGGTGTTTAACAACTCCGTACCTGTGCAGAACCCAAAGGGGACCACCTC
2041  ----------+---------+---------+---------+---------+---------+  2100
      CGAGACCCCAGACCACAAATTGTTGAGGCATGGACACGTCTTGGGTTTCCCCTGGTGGAG

629   K  I  M  V  S  V  W  A  F  F  A  V  I  F  L  A  S  Y  T  A   648
      CAAGATCATGGTGTCAGTGTGGGCCTTCTTTGCTGTCATCTTCCTGGCCAGCTACACTGC
2101  ----------+---------+---------+---------+---------+---------+  2160
      GTTCTAGTACCACAGTCACACCCGGAAGAAACGACAGTAGAAGGACCGGTCGATGTGACG
```

FIG. IG

```
649   N  L  A  A  F  M  I  Q  E  E  Y  V  D  Q  V  S  G  L  S  D     668
      CAACTTAGCTGCCTTCATGATCCAAGAGGAATATGTGGACCAGGTTTCTGGCCTGAGCGA
2161  ----------+---------+---------+---------+---------+---------+  2220
      GTTGAATCGACGGAAGTACTAGGTTCTCCTTATACACCTGGTCCAAAGACCGGACTCGCT

669   K  K  F  Q  R  P  N  D  F  S  P  P  F  R  F  G  T  V  P  N     688
      CAAAAAGTTCCAGAGACCTAATGACTTCTCACCCCCTTTCCGCTTTGGGACCGTGCCCAA
2221  ----------+---------+---------+---------+---------+---------+  2280
      GTTTTTCAAGGTCTCTGGATTACTGAAGAGTGGGGGAAAGGCGAAACCCTGGCACGGGTT

Sph I
689   G  S  T  E  R  N  I  R  N  N  Y  A  E  M  H  A  Y  M  G  K     708
      CGGCAGCACAGAGAGAAATATTCGCAATAACTATGCAGAAATGCATGCCTACATGGGAAA
2281  ----------+---------+---------+---------+---------+---------+  2340
      GCCGTCGTGTCTCTCTTTATAAGCGTTATTGATACGTCTTTACGTACGGATGTACCCTTT

709   F  N  Q  R  G  V  D  D  A  L  L  S  L  K  T  G  K  L  D  A     728
      GTTCAACCAGAGGGGTGTAGATGATGCATTGCTCTCCCTGAAAACAGGGAAACTGGATGC
2341  ----------+---------+---------+---------+---------+---------+  2400
      CAAGTTGGTCTCCCCACATCTACTACGTAACGAGAGGGACTTTTGTCCCTTTGACCTACG

729   F  I  Y  D  A  A  V  L  N  Y  M  A  G  R  D  E  G  C  K  L     748
      CTTCATCTATGATGCAGCAGTGCTGAACTATATGGCAGGCAGAGATGAAGGCTGCAAGCT
2401  ----------+---------+---------+---------+---------+---------+  2460
      GAAGTAGATACTACGTCGTCACGACTTGATATACCGTCCGTCTCTACTTCCGACGTTCGA

749   V  T  I  G  S  G  K  V  F  A  S  T  G  Y  G  I  A  I  Q  K     768
      GGTGACCATTGGCAGTGGGAAGGTCTTTGCTTCCACTGGCTATGGCATTGCCATCCAAAA
2461  ----------+---------+---------+---------+---------+---------+  2520
      CCACTGGTAACCGTCACCCTTCCAGAAACGAAGGTGACCGATACCGTAACGGTAGGTTTT
```

FIG. 1H

```
769   D  S  G  W  K  R  Q  V  D  L  A  I  L  Q  L  F  G  D  G  E    788
      AGATTCTGGGTGGAAGCGCCAGGTGGACCTTGCTATCCTGCAGCTCTTTGGAGATGGGGA
2521  ----------+----------+----------+----------+----------+----------+  2580
      TCTAAGACCCACCTTCGCGGTCCACCTGGAACGATAGGACGTCGAGAAACCTCTACCCCT

789   M  E  E  L  E  A  L  W  L  T  G  I  C  H  N  E  K  N  E  V    808
      GATGGAAGAACTGGAAGCTCTCTGGCTCACTGGCATTTGTCACAATGAGAAGAATGAGGT
2581  ----------+----------+----------+----------+----------+----------+  2640
      CTACCTTCTTGACCTTCGAGAGACCGAGTGACCGTAAACAGTGTTACTCTTCTTACTCCA

809   M  S  S  Q  L  D  I  D  N  M  A  G  V  F  Y  M  L  G  A  A    828
      CATGAGCAGCCAGCTGGACATTGACAACATGGCAGGGGTCTTCTACATGTTGGGGGCGGC
2641  ----------+----------+----------+----------+----------+----------+  2700
      GTACTCGTCGGTCGACCTGTAACTGTTGTACCGTCCCCAGAAGATGTACAACCCCCGCCG

829   M  A  L  S  L  I  T  F  I  C  E  H  L  F  Y  W  Q  F  R  H    848
      CATGGCTCTCAGCCTCATCACCTTCATCTGCGAACACCTTTTCTATTGGCAGTTCCGACA
2701  ----------+----------+----------+----------+----------+----------+  2760
      GTACCGAGAGTCGGAGTAGTGGAAGTAGACGCTTGTGGAAAAGATAACCGTCAAGGCTGT

849   C  F  M  G  V  C  S  G  K  P  G  M  V  F  S  I  S  R  G  I    868
      TTGCTTTATGGGTGTCTGTTCTGGCAAGCCTGGCATGGTCTTCTCCATCAGCAGAGGTAT
2761  ----------+----------+----------+----------+----------+----------+  2820
      AACGAAATACCCACAGACAAGACCGTTCGGACCGTACCAGAAGAGGTAGTCGTCTCCATA

869   Y  S  C  I  H  G  V  A  I  E  E  R  Q  S  V  M  N  S  P  T    888
      CTACAGCTGCATCCATGGGGTGGCGATCGAGGAGCGCCAGTCTGTAATGAACTCCCCCAC
2821  ----------+----------+----------+----------+----------+----------+  2880
      GATGTCGACGTAGGTACCCCACCGCTAGCTCCTCGCGGTCAGACATTACTTGAGGGGGTG
```

FIG. 11

```
889  A  T  M  N  N  T  H  S  N  I  L  R  L  L  R  T  A  K  N  M   908
     TGCAACCATGAACAACACACACTCCAACATCCTGCGCCTGCTGCGCACGGCCAAGAACAT
2881 ----------+---------+---------+---------+---------+---------+ 2940
     GCGTTGGTACTTGTTGTGTGTGAGGTTGTAGGACGCGGACGACGCGTGCCGGTTCTTGTA

909  A  N  L  S  G  V  N  G  S  P  Q  R  P  L  D  F  I  R  R  E   928
     GGCTAACCTGTCTGGTGTGAATGGCTCACCGCAGAGGCCCCTGGACTTCATCCGACGGGA
2941 ----------+---------+---------+---------+---------+---------+ 3000
     CCGATTGGACAGACCACACTTACCGAGTGGCGTCTCCGGGGACCTGAAGTAGGCTGCCCT

929  S  S  V  Y  D  I  S  E  H  R  R  S  F  T  H  S  D  C  K  S   948
     GTCATCCGTCTATGACATCTCAGAGCACCGCCGCAGCTTCACGCATTCTGACTGCAAATC
3001 ----------+---------+---------+---------+---------+---------+ 3060
     CAGTAGGCAGATACTGTAGAGTCTCGTGGCGGCGTCGAAGTGCGTAAGACTGACGTTTAG

949  Y  N  N  P  P  C  E  E  N  L  F  S  D  Y  I  S  E  V  E  R   968
     CTACAACAACCCGCCCTGTGAGGAGAACCTCTTCAGTGACTACATCAGTGAGGTAGAGAG
3061 ----------+---------+---------+---------+---------+---------+ 3120
     GATGTTGTTGGGCGGGACACTCCTCTTGGAGAAGTCACTGATGTAGTCACTCCATCTCTC

969  T  F  G  N  L  Q  L  K  D  S  N  V  Y  Q  D  H  Y  H  H  H   988
     AACGTTCGGGAACCTGCAGCTGAAGGACAGCAACGTGTACCAAGATCACTACCACCATCA
3121 ----------+---------+---------+---------+---------+---------+ 3180
     TTGCAAGCCCTTGGACGTCGACTTCCTGTCGTTGCACATGGTTCTAGTGATGGTGGTAGT

989  H  R  P  H  S  I  G  S  A  S  S  I  D  G  L  Y  D  C  D  N   1008
     CCACCGGCCCCATAGTATTGGCAGTGCCAGCTCCATCGATGGGCTCTACGACTGTGACAA
3181 ----------+---------+---------+---------+---------+---------+ 3240
     GGTGGCCGGGGTATCATAACCGTCACGGTCGAGGTAGCTACCCGAGATGCTGACACTGTT
```

FIG. IJ

```
1009   P  P  F  T  T  Q  S  R  S  I  S  K  K  P  L  D  I  G  L  P    1028
       CCCACCCTTCACCACCCAGTCCAGGTCCATCAGCAAGAAGCCCCTGGACATCGGCCTCCC
3241   ----------+----------+----------+----------+----------+---------+  3300
       GGGTGGGAAGTGGTGGGTCAGGTCCAGGTAGTCGTTCTTCGGGGACCTGTAGCCGGAGGG

1029   S  S  K  H  S  Q  L  S  D  L  Y  G  K  F  S  F  K  S  D  R    1048
       CTCCTCCAAGCACAGCCAGCTCAGTGACCTGTACGGCAAATTCTCCTTCAAGAGCGACCG
3301   ----------+----------+----------+----------+----------+---------+  3360
       GAGGAGGTTCGTGTCGGTCGAGTCACTGGACATGCCGTTTAAGAGGAAGTTCTCGCTGGC

1049   Y  S  G  H  D  D  L  I  R  S  D  V  S  D  I  S  T  H  T  V    1068
       CTACAGTGGCCACGACGACTTGATCCGCTCCGATGTCTCTGACATCTCAACCCACACCGT
3361   ----------+----------+----------+----------+----------+---------+  3420
       GATGTCACCGGTGCTGCTGAACTAGGCGAGGCTACAGAGACTGTAGAGTTGGGTGTGGCA

1069   T  Y  G  N  I  E  G  N  A  A  K  R  R  K  Q  Q  Y  K  D  S    1088
       CACCTATGGAACATCGAGGGCAATGCCGCCAAGAGGCGTAAGCAGCAATATAAGGACAG
3421   ----------+----------+----------+----------+----------+---------+  3480
       GTGGATACCCTTGTAGCTCCCGTTACGGCGGTTCTCCGCATTCGTCGTTATATTCCTGTC

1089   L  K  K  R  P  A  S  A  K  S  R  R  E  F  D  E  I  E  L  A    1108
       CCTGAAGAAGCGGCCTGCCTCGGCCAAGTCCCGCAGGGAGTTTGACGAGATCGAGCTGGC
3481   ----------+----------+----------+----------+----------+---------+  3540
       GGACTTCTTCGCCGGACGGAGCCGGTTCAGGGCGTCCCTCAAACTGCTCTAGCTCGACCG

1109   Y  R  R  R  P  P  R  S  P  D  H  K  R  Y  F  R  D  K  E  G    1128
       CTACCGTCGCCGACCGCCCCGCTCCCCTGACCACAAGCGCTACTTCAGGGACAAGGAAGG
3541   ----------+----------+----------+----------+----------+---------+  3600
       GATGGCAGCGGCTGGCGGGGCGAGGGGACTGGTGTTCGCGATGAAGTCCCTGTTCCTTCC
```

FIG. IK

```
1129  L  R  D  F  Y  L  D  Q  F  R  T  K  E  N  S  P  H  W  E  H   1148
      GCTACGGGACTTCTACCTGGACCAGTTCCGAACAAAGGAGAACTCACCCCACTGGGAGCA
3601  ---------+---------+---------+---------+---------+---------+  3660
      CGATGCCCTGAAGATGGACCTGGTCAAGGCTTGTTTCCTCTTGAGTGGGGTGACCCTCGT

1149  V  D  L  T  D  I  Y  K  E  R  S  D  D  F  K  R  D  S  V  S   1168
      CGTAGACCTGACCGACATCTACAAGGAGCGGAGTGATGACTTTAAGCGCGACTCCGTCAG
3661  ---------+---------+---------+---------+---------+---------+  3720
      GCATCTGGACTGGCTGTAGATGTTCCTCGCCTCACTACTGAAATTCGCGCTGAGGCAGTC

1169  G  G  G  P  C  T  N  R  S  H  I  K  H  G  T  G  D  K  H  G   1188
      CGGAGGAGGGCCCTGTACCAACAGGTCTCACATCAAGCACGGGACGGGCGACAAACACGG
3721  ---------+---------+---------+---------+---------+---------+  3780
      GCCTCCTCCCGGGACATGGTTGTCCAGAGTGTAGTTCGTGCCCTGCCCGCTGTTTGTGCC

1189  V  V  S  G  V  P  A  P  W  E  K  N  L  T  N  V  E  W  E  D   1208
      CGTGGTCAGCGGGGTACCTGCACCTTGGGAGAAGAACCTGACCAACGTGGAGTGGGAGGA
3781  ---------+---------+---------+---------+---------+---------+  3840
      GCACCAGTCGCCCCATGGACGTGGAACCCTCTTCTTGGACTGGTTGCACCTCACCCTCCT

1209  R  S  G  G  N  F  C  R  S  C  P  S  K  L  H  N  Y  S  T  T   1228
      CCGGTCCGGGGGCAACTTCTGCCGCAGCTGTCCCTCCAAGCTGCACAACTACTCCACGAC
3841  ---------+---------+---------+---------+---------+---------+  3900
      GGCCAGGCCCCCGTTGAAGACGGCGTCGACAGGGAGGTTCGACGTGTTGATGAGGTGCTG

1229  V  T  G  Q  N  S  G  R  Q  A  C  I  R  C  E  A  C  K  K  A   1248
      GGTGACGGGTCAGAACTCGGGCAGGCAGGCGTGCATCCGGTGTGAGGCTTGCAAGAAAGC
3901  ---------+---------+---------+---------+---------+---------+  3960
      CCACTGCCCAGTCTTGAGCCCGTCCGTCCGCACGTAGGCCACACTCCGAACGTTCTTTCG
```

FIG. IL

```
1249  G  N  L  Y  D  I  S  E  D  N  S  L  Q  E  L  D  Q  P  A  A   1268
      AGGCAACCTGTATGACATCAGTGAGGACAACTCCCTGCAGGAACTGGACCAGCCGGCTGC
3961  ----------+----------+----------+----------+----------+----------+  4020
      TCCGTTGGACATACTGTAGTCACTCCTGTTGAGGGACGTCCTTGACCTGGTCGGCCGACG

1269  P  V  A  V  T  S  N  A  S  T  T  K  Y  P  Q  S  P  T  N  S   1288
      CCCAGTGGCGGTGACGTCAAACGCCTCCACCACTAAGTACCCTCAGAGCCCGACTAATTC
4021  ----------+----------+----------+----------+----------+----------+  4080
      GGGTCACCGCCACTGCAGTTTGCGGAGGTGGTGATTCATGGGAGTCTCGGGCTGATTAAG

1289  K  A  Q  K  K  N  R  N  K  L  R  R  Q  H  S  Y  D  T  F  V   1308
      CAAGGCCCAGAAGAAGAACCGGAACAAACTGCGCCGGCAGCACTCCTACGACACCTTCGT
4081  ----------+----------+----------+----------+----------+----------+  4140
      GTTCCGGGTCTTCTTCTTGGCCTTGTTTGACGCGGCCGTCGTGAGGATGCTGTGGAAGCA

1309  D  L  Q  K  E  E  A  A  L  A  P  R  S  V  S  L  K  D  K  G   1328
      GGACCTGCAGAAGGAAGAAGCCGCCCTGGCCCCGCGCAGCGTAAGCCTGAAAGACAAGGG
4141  ----------+----------+----------+----------+----------+----------+  4200
      CCTGGACGTCTTCCTTCTTCGGCGGGACCGGGGCGCGTCGCATTCGGACTTTCTGTTCCC

1329  R  F  M  D  G  S  P  Y  A  H  M  F  E  M  S  A  G  E  S  T   1348
      CCGATTCATGGATGGGAGCCCCTACGCCCACATGTTTGAGATGTCAGCTGGCGAGAGCAC
4201  ----------+----------+----------+----------+----------+----------+  4260
      GGCTAAGTACCTACCCTCGGGGATGCGGGTGTACAAACTCTACAGTCGACCGCTCTCGTG

1349  F  A  N  N  K  S  S  V  P  T  A  G  H  H  H  H  N  P  G   1368
      CTTTGCCAACAACAAGTCCTCAGTGCCCACTGCCGGACATCACCACCACAACAACCCCGG
4261  ----------+----------+----------+----------+----------+----------+  4320
      GAAACGGTTGTTGTTCAGGAGTCACGGGTGACGGCCTGTAGTGGTGGTGTTGTTGGGGCC
```

FIG. 1M

```
1369  G  G  Y  M  L  S  K  S  L  Y  P  D  R  V  T  Q  N  P  F  I   1388
      CGGCGGGTACATGCTCAGCAAGTCGCTCTACCCTGACCGGGTCACGCAAAACCCTTTCAT
4321  ---------+---------+---------+---------+---------+---------+   4380
      GCCGCCCATGTACGAGTCGTTCAGCGAGATGGGACTGGCCCAGTGCGTTTTGGGAAAGTA

1389  P  T  F  G  D  D  Q  C  L  L  H  G  S  K  S  Y  F  F  R  Q   1408
      CCCCACTTTTGGGGACGACCAGTGCTTGCTCCATGGCAGCAAATCCTACTTCTTCAGGCA
4381  ---------+---------+---------+---------+---------+---------+   4440
      GGGGTGAAAACCCCTGCTGGTCACGAACGAGGTACCGTCGTTTAGGATGAAGAAGTCCGT

1409  P  T  V  A  G  A  S  K  A  R  P  D  F  R  A  L  V  T  N  K   1428
      GCCCACGGTGGCGGGGGCGTCGAAAGCCAGGCCGGACTTCCGGGCCCTTGTCACCAACAA
4441  ---------+---------+---------+---------+---------+---------+   4500
      CGGGTGCCACCGCCCCCGCAGCTTTCGGTCCGGCCTGAAGGCCCGGGAACAGTGGTTGTT

1429  P  V  V  S  A  L  H  G  A  V  P  A  R  F  Q  K  D  I  C  I   1448
      GCCGGTGGTCTCGGCCCTTCATGGGGCCGTGCCAGCCCGTTTCCAGAAGGACATCTGTAT
4501  ---------+---------+---------+---------+---------+---------+   4560
      CGGCCACCAGAGCCGGGAAGTACCCCGGCACGGTCGGGCAAAGGTCTTCCTGTAGACATA

1449  G  N  Q  S  N  P  C  V  P  N  N  K  N  P  R  A  F  N  G  S   1468
      AGGGAACCAGTCCAACCCCTGTGTGCCTAACAACAAAAACCCCAGGGCTTTCAATGGCTC
4561  ---------+---------+---------+---------+---------+---------+   4620
      TCCCTTGGTCAGGTTGGGGACACACGGATTGTTGTTTTTGGGGTCCCGAAAGTTACCGAG

1469  S  N  G  H  V  Y  E  K  L  S  S  I  E  S  D  V  (SEQ ID NO:2)  1484
      CAGCAATGGGCATGTTTATGAGAAACTTTCTAGTATTGAGTCTGATGTCTGAGTGAGGGA
4621  ---------+---------+---------+---------+---------+---------+   4680
      GTCGTTACCCGTACAAATACTCTTTGAAAGATCATAACTCAGACTACAGACTCACTCCCT
```

FIG. 1N

```
       ACAGAGAGGTTAAGGTGGGTACGGGAGGGTAAGGCTGTGGGTCGCGTGATGCGCATGTCA
4681   ----------+----------+----------+----------+----------+----------+   4740
       TGTCTCTCCAATTCCACCCATGCCCTCCCATTCCGACACCCAGCGCACTACGCGTACAGT

CGGAGGGTGACGGGGGTGAACTTGGTTCCCATTTGCTCCTTTCTTGTTTTAATTTATTTA
4741   ----------+----------+----------+----------+----------+----------+   4800
       GCCTCCCACTGCCCCCACTTGAACCAAGGGTAAACGAGGAAAGAACAAAATTAAATAAAT

Bam HI
         ↓
       TGGGGATCCTGGAGTTCTGGTTCCTACTGGGGGCAACCCTGGTGACCAGCACCATCTCTC
4801   ----------+----------+----------+----------+----------+----------+   4860
       ACCCCTAGGACCTCAAGACCAAGGATGACCCCCGTTGGGACCACTGGTCGTGGTAGAGAG

CTCCTTTTCACAGTTCTCTCCTTCTTCCCCCCGCTGTCAGCCATTCCTGTTCCCATGAGA
4861   ----------+----------+----------+----------+----------+----------+   4920
       GAGGAAAAGTGTCAAGAGAGGAAGAAGGGGGGCGACAGTCGGTAAGGACAAGGGTACTCT

Sph I
                                                         ↓
       TGATGCCATGGGTCTCAGCAGGGGAGGGTAGAGCGGAGAAAGGAAGGGCAGCATGCGGGC
4921   ----------+----------+----------+----------+----------+----------+   4980
       ACTACGGTACCCAGAGTCGTCCCCTCCCATCTCGCCTCTTTCCTTCCCGTCGTACGCCCG

TTCCTCCTGGTGTGGAAGAGCTCCTTGATATCCTCTTTGAGTGAAGCTGGGAGAACCAAA
4981   ----------+----------+----------+----------+----------+----------+   5040
       AAGGAGGACCACACCTTCTCGAGGAACTATAGGAGAAACTCACTTCGACCCTCTTGGTTT
```

FIG. IP

```
      CTTGACTCTTTCTATTGTTTCTTTCAATATCCCCAAGCAGTGTGATTGTTTGGCTTATAT
5461  ---------+---------+---------+---------+---------+---------+  5520
      GAACTGAGAAAGATAACAAAGAAAGTTATAGGGGTTCGTCACACTAACAAACCGAATATA

ACAGACAGAGATGGCCATGTATTACCTGAATTTTGGCTGTGTCTCCCTTCATCCTTCTGG
5521  ---------+---------+---------+---------+---------+---------+  5580
      TGTCTGTCTCTACCGGTACATAATGGACTTAAAACCGACACAGAGGGAAGTAGGAAGACC

AATAAGGAGAATGAAAATTCTTGATAAAGAAGATTCTGTGGTCTAAACAAAAAAAGGCGG
5581  ---------+---------+---------+---------+---------+---------+  5640
      TTATTCCTCTTACTTTTAAGAACTATTTCTTCTAAGACACCAGATTTGTTTTTTTCCGCC

TGAGCAATCCTGCAAGAGCAAGGTACATAAACAAGTCCTCAGTGGTTGGCAACTGTTTCA
5641  ---------+---------+---------+---------+---------+---------+  5700
      ACTCGTTAGGACGTTCTCGTTCCATGTATTTGTTCAGGAGTCACCAACCGTTGACAAAGT

ACCTGTTTGAACCAAGAACCTTCCAGGAAGGCTAAAGGGAAACCGAATTTCACAGCCATG
5701  ---------+---------+---------+---------+---------+---------+  5760
      TGGACAAACTTGGTTCTTGGAAGGTCCTTCCGATTTCCCTTTGGCTTAAAGTGTCGGTAC

ATTCTTTTGCCCACACTTGGGAGCAAAAGATTCTACAAAGCTCTTTTGAGCATTTAGACT
5761  ---------+---------+---------+---------+---------+---------+  5820
      TAAGAAAACGGGTGTGAACCCTCGTTTTCTAAGATGTTTCGAGAAAACTCGTAAATCTGA

CTCGACTGGCCAAGGTTTGGGGAAGAACGAAGCCACCTTTGAAGAAGTAAGGAGTCGTGT
5821  ---------+---------+---------+---------+---------+---------+  5880
      GAGCTGACCGGTTCCAAACCCCTTCTTGCTTCGGTGGAAACTTCTTCATTCCTCAGCACA

ATGGTAGGGTAAGTGAGAGAGGGGGATGTTTCCAATGCTTTGATCCCTTCTTACTTAACC
5881  ---------+---------+---------+---------+---------+---------+  5940
      TACCATCCCATTCACTCTCTCCCCCTACAAAGGTTACGAAACTAGGGAAGAATGAATTGG
```

FIG. 1Q

```
                                        Eco RI
                                          ↓
       TGAAGCTAGACGAGCAGGCTTCTTCCCCCCAAAACTGAATTCC   (SEQ ID NO:1)
5941   ---------+---------+---------+---------+---   5983
       ACTTCGATCTGCTCGTCCGAAGAAGGGGGGTTTTGACTTAAGG
```

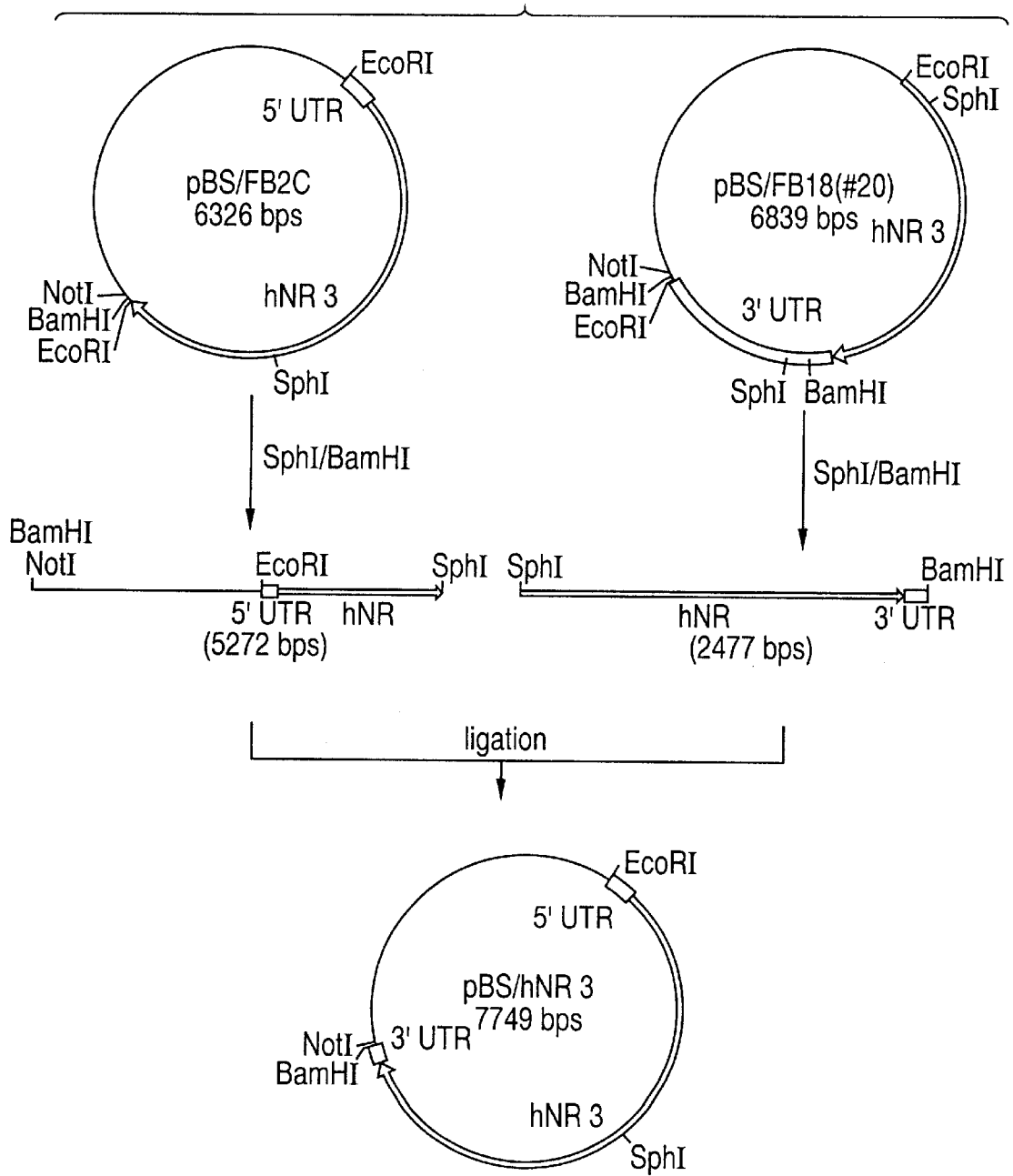

FIG. 3

NR3-1

```
389   Y  V  W  P  R  M  C  P  E  T  E  E  Q  E  D  D  H  L  S  I   408
                                                      *
1381 CTATGTGTGGCCCCGAATGTGTCCAGAGACTGAAGAGCAGGAGGATGACCATCTGAGCAT 1440
     ||||||||||||||||||||||||||||||||||||||||||||||||||||||||||||
1381 CTATGTGTGGCCCCGAATGTGTCCAGAGACTGAAGAGCAGGAGGATGACCATCTGAACAT 1440
                                                      *
389   Y  V  W  P  R  M  C  P  E  T  E  E  Q  E  D  D  H  L  N  I   408
```

NR3-2

FIG. 4A

```
  1  A  F  Y  R  H  L  L  N  V  T  W  E  G  R  D  F  S  F  S  P        20
     GCCTTCTACAGGCACCTACTGAATGTCACCTGGGAGGGCCGAGACTTCTCCTTCAGCCCT
  1  ----------+---------+---------+---------+---------+---------+     60
     CGGAAGATGTCCGTGGATGACTTACAGTGGACCCTCCCGGCTCTGAAGAGGAAGTCGGGA

21  G  G  Y  L  V  Q  P  T  M  V  V  I  A  L  N  R  H  R  L  W        40
     GGTGGGTACCTGGTCCAGCCCACCATGGTGGTGATCGCCCTCAACCGGCACCGCCTCTGG
 61  ----------+---------+---------+---------+---------+---------+    120
     CCACCCATGGACCAGGTCGGGTGGTACCACCACTAGCGGGAGTTGGCCGTGGCGGAGACC

41  E  M  V  G  R  W  E  H  G  V  L  Y  M  K  Y  P  V  W  P  R        60
     GAGATGGTGGGGCGCTGGGAGCATGGCGTCCTATACATGAAGTACCCCGTGTGGCCTCGC
121  ----------+---------+---------+---------+---------+---------+    180
     CTCTACCACCCCGCGACCCTCGTACCGCAGGATATGTACTTCATGGGGCACACCGGAGCG

61  Y  S  A  S  L  Q  P  V  V  D  S  R  H  L  T  V  A  T  L  E        80
     TACAGTGCCTCTCTGCAGCCTGTGGTGGACAGTCGGCACCTGACGGTGGCCACGCTGGAA
181  ----------+---------+---------+---------+---------+---------+    240
     ATGTCACGGAGAGACGTCGGACACCACCTGTCAGCCGTGGACTGCCACCGGTGCGACCTT

81  E  R  P  F  V  I  V  E  S  P  D  P  G  T  G  G  C  V  P  N       100
     GAGCGGCCCTTTGTCATCGTGGAGAGCCCTGACCCTGGCACAGGAGGCTGTGTCCCCAAC
241  ----------+---------+---------+---------+---------+---------+    300
     CTCGCCGGGAAACAGTAGCACCTCTCGGGACTGGGACCGTGTCCTCCGACACAGGGGTTG

101  T  V  P  C  R  R  Q  S  N  H  T  F  S  S  G  D  V  A  P  Y       120
     ACCGTGCCCTGCCGCAGGCAGAGCAACCACACCTTCAGCAGCGGGGACGTGGCCCCCTAC
301  ----------+---------+---------+---------+---------+---------+    360
     TGGCACGGGACGGCGTCCGTCTCGTTGGTGTGGAAGTCGTCGCCCCTGCACCGGGGGATG
```

FIG. 4B

```
121  T  K  L  C  C  K  G  F  C  I  D  I  L  K  K  L  A  R  V  V       140
     ACCAAGCTCTGCTGTAAGGGATTCTGCATCGACATCCTCAAGAAGCTGGCCAGAGTGGTC
361  ---------+---------+---------+---------+---------+---------+    420
     TGGTTCGAGACGACATTCCCTAAGACGTAGCTGTAGGAGTTCTTCGACCGGTCTCACCAG

141  K  F  S  Y  D  L  Y  L  V  T  N  G  K  H  G  K  R  V  R  G       160
     AAATTCTCCTACGACCTGTACCTGGTGACCAACGGCAAGCATGGCAAGCGGGTGCGCGGC
421  ---------+---------+---------+---------+---------+---------+    480
     TTTAAGAGGATGCTGGACATGGACCACTGGTTGCCGTTCGTACCGTTCGCCCACGCGCCG

161  V  W  N  G  M  I  G  E  V  Y  Y  K  R  A  D  M  A  I  G  S       180
     GTATGGAACGGCATGATTGGGGAGGTGTACTACAAGCGGGCAGACATGGCCATCGGCTCC
481  ---------+---------+---------+---------+---------+---------+    540
     CATACCTTGCCGTACTAACCCCTCCACATGATGTTCGCCCGTCTGTACCGGTAGCCGAGG

181  L  T  I  N  E  E  R  S  E  I  V  D  F  S  V  P  F  V  E  T       200
     CTCACCATCAATGAGGAACGCTCCGAGATCGTAGACTTCTCTGTACCCTTTGTGGAGACG
541  ---------+---------+---------+---------+---------+---------+    600
     GAGTGGTAGTTACTCCTTGCGAGGCTCTAGCATCTGAAGAGACATGGGAAACACCTCTGC

201  G  I  S  V  M  V  A  R  S  N  G  T  V  S  P  S  A  F  L  E       220
     GGCATCAGTGTGATGGTGGCTCGCAGCAATGGCACCGTCTCCCCCTCGGCCTTCTTGGAG
601  ---------+---------+---------+---------+---------+---------+    660
     CCGTAGTCACACTACCACCGAGCGTCGTTACCGTGGCAGAGGGGGAGCCGGAAGAACCTC

221  P  Y  S  P  A  V  W  V  M  M  F  V  M  C  L  T  V  V  A  I       240
     CCATATAGCCCTGCAGTGTGGGTGATGATGTTTGTCATGTGCCTCACTGTGGTGGCCATC
661  ---------+---------+---------+---------+---------+---------+    720
     GGTATATCGGGACGTCACACCCACTACTACAAACAGTACACGGAGTGACACCACCGGTAG

241  T  V  F  M  F  E  Y  F  S  P  V  S  Y  N  Q  N  L  T  R  G       260
```

FIG. 4C

```
     ACCGTCTTCATGTTCGAGTACTTCAGCCCTGTCAGCTACAACCAGAACCTCACCAGAGGC
721  ------+---------+---------+---------+---------+---------+  780
     TGGCAGAAGTACAAGCTCATGAAGTCGGGACAGTCGATGTTGGTCTTGGAGTGGTCTCCG

261  K  K  S  G  G  P  A  F  T  I  G  K  S  V  W  L  L  W  A  L   280
     AAGAAGTCCGGGGGCCCAGCTTTCACTATCGGCAAGTCCGTGTGGCTGCTGTGGGCGCTG
781  ------+---------+---------+---------+---------+---------+  840
     TTCTTCAGGCCCCCGGGTCGAAAGTGATAGCCGTTCAGGCACACCGACGACACCCGCGAC

281  V  F  N  N  S  V  P  I  E  N  P  R  G  T  T  S  K  I  M  V   300
     GTCTTCAACAACTCAGTGCCCATCGAGAACCCGCGGGGCACCACCAGCAAGATCATGGTT
841  ------+---------+---------+---------+---------+---------+  900
     CAGAAGTTGTTGAGTCACGGGTAGCTCTTGGGCGCCCCGTGGTGGTCGTTCTAGTACCAA

301  L  V  W  A  F  F  A  V  I  F  L  A  S  Y  T  A  N  L  A  A   320
     CTGGTCTGGGCCTTCTTTGCTGTCATCTTCCTCGCCAGCTACACGGCCAACCTggccgcc
901  ------+---------+---------+---------+---------+---------+  960
     GACCAGACCCGGAAGAAACGACAGTAGAAGGAGCGGTCGATGTGCCGGTTGGAccggcgg 321  F  M  I  Q  E  Q  Y  I  D  T  V  S  G  L  S  D  K  K  F  Q   340
     ttcatgatccaagagcaatacatcgacactgtgtcgggcctcagtgacaagaagtttcag
961  ------+---------+---------+---------+---------+---------+  1020
     aagtactaggttctcgttatgtagctgtgacacagcccggagtcactgttcttcaaagtc
```

FIG. 4D

```
341  R  P  Q  D  Q  Y  P  P  F  R  F  G  T  V  P  N  G  S  T  E   360
     cggcctcaagatcagtacccacctttccgcttcggcacggtGcccaacggcagcacggaG
1021 ---------+---------+---------+---------+---------+---------+ 1080
     gccggagttctagtcatgggtggaaaggcgaagccgtgccaCgggttgccgtcgtgcctC 361  R  N  I  R  S  N  Y  R  D  M  H  T  H  M  V  K  F  N  Q  R   380
     cggaacatccgcagtaaCTACCGTGACATGCACACCCACATGGTCAAGTTCAACCAGCGC
1081 ---------+---------+---------+---------+---------+---------+ 1140
     gccttgtaggcgtcattGATGGCACTGTACGTGTGGGTGTACCAGTTCAAGTTGGTCGCG 381  S  V  E  D  A  L  T  S  L  K  M  G  K  L  D  A  F  I  Y  D   400
     TCGGTGGAGGACGCGCTCACCAGCCTCAAGATGggggaagctggatgccttcatctatgat
1141 ---------+---------+---------+---------+---------+---------+ 1200
     AGCCACCTCCTGCGCGAGTGGTCGGAGTTCTAccccttcgacctacggaagtagatacta 401  A  A  V  L  N  Y  M  A  G  K  D  E  G  C  K  L  V  T  I  G   420
     gctgctgtcctcaactacatggcaggcaaggacgagggctgcaagctggtcaccattggg
1201 ---------+---------+---------+---------+---------+---------+ 1260
     cgacgacaggagttgatgtaccgtccgttcctgctcccgacgttcgaccagtggtaaccc 421  S  G  K  V  F  A  T  T  G  Y  G  I  A  M  Q  K  D  S  H  W   440
     tctggcaaggtctttgctaccactggctacggcatcgccatgcagaaggactcccactgg
1261 ---------+---------+---------+---------+---------+---------+ 1320
     agaccgttccagaaacgatggtgaccgatgccgtagcggtacgtcttcctgagggtgacc 441  K       441        (SEQ ID NO:8)
     aag                (SEQ ID NO:7)
1321 ---     1323
     ttc
```

FIG. 5

```
                                TCTGGGTGATGATGTTTGTGATGCTGCTC
                        1832  --------+---------+--------+   1860

ATTGTTTCTGCCATAGCTGTTTTTTGTCTTTGAATACTTCAGCCCTGTTGGATACAACAGA
1861   ---------+---------+---------+---------+---------+---------+   1920

AACTTAGCCAAAGGGAAAGCACCCCATGGGCCTTCTTTTACAATTGGAAAAGCTATATGG
1921   ---------+---------+---------+---------+---------+---------+   1980

CTTCTTTGGGGCCTGGTGTTCAATAACTCCGTGCCTGTCCAGAATCCTAAAGGGACCACC
1981   ---------+---------+---------+---------+---------+---------+   2040

AGCAAGATCATGGTATCTGTATGGGCCTTCTTCGCTGTCATATTCCTGGCTAGCTACACA
2041   ---------+---------+---------+---------+---------+---------+   2100

GCCAATCTGGCTGCCTTCATGATCCAAGAGGAATTTGTGGACCAAGTGACCGGCCTCAGT
2101   ---------+---------+---------+---------+---------+---------+   2160

GACAAAAAGTTTCAGAGACCTCATGACTATTCCCCACCTTTTCGATTTGGGACAGTGCCT
2161   ---------+---------+---------+---------+---------+---------+   2220

AATGGAAGCACGGAGAGAAACATTCGGAATAACTATCCCTACATGCATCAGTACATGACC
2221   ---------+---------+---------+---------+---------+---------+   2280

AAATTTAATCAGAAAGGAGTAGAGGACGCCTTGGTCAGCCTGAAAACGGGGAAGCTGGAC
2281   ---------+---------+---------+---------+---------+---------+   2340

GCTTTCATCTACGATGCCGCA    (SEQ ID NO:9)
2341   ---------+--------+-  2361
```

FIG. 6A

Eco RI

```
GAATTCCGGTAAGGCTCTGGAAAAGGGGGCGCTGGGAGCGCATTGCGAGGGGGCTGGAGA
----------+----------+----------+----------+----------+----------+ 60
CTTAAGGCCATTCCGAGACCTTTTCCCCCGCGACCCTCGCGTAACGCTCCCCCGACCTCT

GGGAGAGAGGAGCGGAAGCTGAGGGTGTGAAACGGCTGGCCCCGAACACACCTCGCGGCG
----------+----------+----------+----------+----------+----------+ 120
CCCTCTCTCCTCGCCTTCGACTCCCACACTTTGCCGACCGGGGCTTGTGTGGAGCGCCGC

CTCCAGTGATTCCTGGTGTCCGACCTCAGCCCCAGTCAGTGCGGGTCCAGTTTCCAGGCT
----------+----------+----------+----------+----------+----------+ 180
GAGGTCACTAAGGACCACAGGCTGGAGTCGGGGTCAGTCACGCCCAGGTCAAAGGTCCGA

CTCGCGGAAGGCCTGGCTGAGCACATGCGGCAGCCACGGTCGCCCTCCCTATTCCTCTTA
----------+----------+----------+----------+----------+----------+ 240
GAGCGCCTTCCGGACCGACTCGTGTACGCCGTCGGTGCCAGCGGGAGGGATAAGGAGAAT

GCCCGAGGAGGGGGGTCCCAAGTTACATGGCCACGCAGATGGGGCCTCTCCCTCATTTCT
----------+----------+----------+----------+----------+----------+ 300
CGGGCTCCTCCCCCCAGGGTTCAATGTACCGGTGCGTCTACCCCGGAGAGGGAGTAAAGA

GAACCTTGTGGGGAGGGGAACCTTGAAGGGAGCGCCCCCCAGAGCCATGGCTTAGGGCCT
----------+----------+----------+----------+----------+----------+ 360
CTTGGAACACCCCTCCCCTTGGAACTTCCCTCGCGGGGGGTCTCGGTACCGAATCCCGGA

CCCCCACCCCTCTGGAGCTCCAGTCTGCAAGAGTCAGGAGCCGAAATATCGCTGACTGTG
----------+----------+----------+----------+----------+----------+ 420
GGGGGTGGGGAGACCTCGAGGTCAGACGTTCTCAGTCCTCGGCTTTATAGCGACTGACAC
```

FIG. 6B

```
GGTGACGACTCTTGCGCGCACACACACATACAAGCGGGCACGACGCGTTCGGTCCTATTA
----------+----------+----------+----------+----------+----------+ 480
CCACTGCTGAGAACGCGCGTGTGTGTATGTTCGCCCGTGCTGCGCAAGCCAGGATAAT

AAAGGCACGCAAGGGTGCGGCTGCACGCGGTGACACGGACCCCTCTAACGTTTCCAAACT
----------+----------+----------+----------+----------+----------+ 540
TTTCCGTGCGTTCCCACGCCGACGTGCGCCACTGTGCCTGGGGAGATTGCAAAGGTTTGA

GAGCTCCCTGCAGGTCCCCGACAGCACAGGCCCCTGTCCCAGGACCCCTCCAGGCACGCG
----------+----------+----------+----------+----------+----------+ 600
CTCGAGGGACGTCCAGGGGCTGTCGTGTCCGGGGACAGGGTCCTGGGGAGGTCCGTGCGC

CTCACACGCACACGCGCGCTCCCCGGCTCACGCGCGCTCCGACACACACGCTCACGCGAA
----------+----------+----------+----------+----------+----------+ 660
GAGTGTGCGTGTGCGCGCGAGGGGCCGAGTGCGCGCGAGGCTGTGTGTGCGAGTGCGCTT

CGCAGGCGCACGCTCTGGCGCGGGAGGCGCCCCTTCGCCTCCGTGTTGGGAAGCGGGGGC
----------+----------+----------+----------+----------+----------+ 720
GCGTCCGCGTGCGAGACCGCGCCCTCCGCGGGGAAGCGGAGGCACAACCCTTCGCCCCCG

GGCGGGAGGGGCAGGAGACGTTGGCCCCGCTCGCGTTTCTGCAGCTGCTGCAGTCGCCGC
----------+----------+----------+----------+----------+----------+ 780
CCGCCCTCCCCGTCCTCTGCAACCGGGGCGAGCGCAAAGACGTCGACGACGTCAGCGGCG

AGCGTCCGGACCGGAACCAGCGCCGTCCGCGGAGCCGCCGCCGCCGCCGCCCGGGCCCTTT
----------+----------+----------+----------+----------+----------+ 840
TCGCAGGCCTGGCCTTGGTCGCGGCAGGCGCCTCGGCGGCGGCGGCGGCCCGGGAAA

CCAAGCCGGGCGCTCGGAGCTGTGCCCGGCCCCGCTTCAGCACCGCGGACAGCTCCGGCC
----------+----------+----------+----------+----------+----------+ 900
GGTTCGGCCCGCGAGCCTCGACACGGGCCGGGGCGAAGTCGTGGCGCCTGTCGAGGCCGG
```

FIG. 6C

```
    GCGTGGGGCTGAGCCGAGCCCCCGCGCACGCTTCAGCCCCCTTCCCTCGGCCGACGTCCC
    ----------+----------+----------+----------+----------+----------+ 960
    CGCACCCCGACTCGGCTCGGGGGCGCGTGCGAAGTCGGGGGAAGGGAGCCGGCTGCAGGG

GGGACCGCCGCTCCGGGGGAGACGTGGCGTCCGCAGCCCGCGGGGCCGGGCGAGCGCAGG
    ----------+----------+----------+----------+----------+----------+1020
    CCCTGGCGGCGAGGCCCCCTCTGCACCGCAGGCGTCGGGCGCCCCGGCCCGCTCGCGTCC

ACGGCCCGGAAGCCCCGCGGGGGATGCGCCGAGGGCCCGCGTTCGCGCCGCGCAGAGCCA
    ----------+----------+----------+----------+----------+----------+1080
    TGCCGGGCCTTCGGGGCGCCCCCTACGCGGCTCCCGGGCGCAAGCGCGGCGCGTCTCGGT

|---------------signal-peptide----------------
                   M   S   T   M   R   L   L   T   L   A   L   L   F   S   -4
    GGCCCGCGGCCCGAGCCCATGAGCACCATGCGCCTGCTGACGCTCGCCCTGCTGTTCTCC
    ----------+----------+----------+----------+----------+----------+1140
    CCGGGCGCCGGGCTCGGGTACTCGTGGTACGCGGACGACTGCGAGCGGGACGACAAGAGG -----------|
     C   S   V   A   R   A   A   C   D   P   K   I   V   N   I   G   A   V   L   S   16
    TGCTCCGTCGCCCGTGCCGCGTGCGACCCCAAGATCGTCAACATTGGCGCGGTGCTGAGC
    ----------+----------+----------+----------+----------+----------+1200
    ACGAGGCAGCGGGCACGGCGCACGCTGGGGTTCTAGCAGTTGTAACCGCGCCACGACTCG T   R   K   H   E   Q   M   F   R   E   A   V   N   Q   A   N   K   R   H   G   36
    ACGCGGAAGCACGAGCAGATGTTCCGCGAGGCCGTGAACCAGGCCAACAAGCGGCACGGC
    ----------+----------+----------+----------+----------+----------+1260
    TGCGCCTTCGTGCTCGTCTACAAGGCGCTCCGGCACTTGGTCCGGTTGTTCGCCGTGCCG
```

FIG. 6D

```
          S   W   K   I   Q   L   N   A   T   S   V   T   H   K   P   N   A   I   Q   M    56
        TCCTGGAAGATTCAGCTCAATGCCACCTCCGTCACGCACAAGCCCAACGCCATCCAGATG
        ----------+---------+---------+---------+---------+---------+1320
        AGGACCTTCTAAGTCGAGTTACGGTGGAGGCAGTGCGTGTTCGGGTTGCGGTAGGTCTAC

A   L   S   V   C   E   D   L   I   S   S   Q   V   Y   A   I   L   V   S   H    76
        GCTCTGTCGGTGTGCGAGGACCTCATCTCCAGCCAGGTCTACGCCATCCTAGTTAGCCAT
        ----------+---------+---------+---------+---------+---------+1380
        CGAGACAGCCACACGCTCCTGGAGTAGAGGTCGGTCCAGATGCGGTAGGATCAATCGGTA

P   P   T   P   N   D   H   F   T   P   T   P   V   S   Y   T   A   G   F   Y    96
        CCACCTACCCCCAACGACCACTTCACTCCCACCCCTGTCTCCTACACAGCCGGCTTCTAC
        ----------+---------+---------+---------+---------+---------+1440
        GGTGGATGGGGGTTGCTGGTGAAGTGAGGGTGGGGACAGAGGATGTGTCGGCCGAAGATG

R   I   P   V   L   G   L   T   T   R   M   S   I   Y   S   D   K   S   I   H   116
        CGCATACCCGTGCTGGGGCTGACCACCCGCATGTCCATCTACTCGGACAAGAGCATCCAC
        ----------+---------+---------+---------+---------+---------+1500
        GCGTATGGGCACGACCCCGACTGGTGGGCGTACAGGTAGATGAGCCTGTTCTCGTAGGTG

L   S   F   L   R   T   V   P   P   Y   S   H   Q   S   S   V   W   F   E   M   136
        CTGAGCTTCCTGCGCACCGTGCCGCCCTACTCCCACCAGTCCAGCGTGTGGTTTGAGATG
        ----------+---------+---------+---------+---------+---------+1560
        GACTCGAAGGACGCGTGGCACGGCGGGATGAGGGTGGTCAGGTCGCACACCAAACTCTAC

M   R   V   Y   S   W   N   H   I   I   L   L   V   S   D   D   H   E   G   R   156
        ATGCGTGTCTACAGCTGGAACCACATCATCCTGCTGGTCAGCGACGACCACGAGGGCCGG
        ----------+---------+---------+---------+---------+---------+1620
        TACGCACAGATGTCGACCTTGGTGTAGTAGGACGACCAGTCGCTGCTGGTGCTCCCGGCC
```

FIG. 6E

```
A  A  Q  K  R  L  E  T  L  L  E  E  R  E  S  K  A  E  K  V  176
GCGGCTCAGAAACGCCTGGAGACGCTGCTGGAGGAGCGTGAGTCCAAGGCAGAGAAGGTG
----------+----------+----------+----------+----------+----------+1680
CGCCGAGTCTTTGCGGACCTCTGCGACGACCTCCTCGCACTCAGGTTCCGTCTCTTCCAC

L  Q  F  D  P  G  T  K  N  V  T  A  L  L  M  E  A  K  E  L  196
CTGCAGTTTGACCCAGGGACCAAGAACGTGACGGCCCTGCTGATGGAGGCGAAAGAGCTG
----------+----------+----------+----------+----------+----------+1740
GACGTCAAACTGGGTCCCTGGTTCTTGCACTGCCGGGACGACTACCTCCGCTTTCTCGAC

E  A  R  V  I  I  L  S  A  S  E  D  D  A  A  T  V  Y  R  A  216
GAGGCCCGGGTCATCATCCTTTCTGCCAGCGAGGACGATGCTGCCACTGTATACCGCGCA
----------+----------+----------+----------+----------+----------+1800
CTCCGGGCCCAGTAGTAGGAAAGACGGTCGCTCCTGCTACGACGGTGACATATGGCGCGT

Bgl II
A  A  M  L  N  M  T  G  S  G  Y  V  W  L  V  G  E  R  E  I  236
GCCGCGATGCTGAACATGACGGGCTCCGGGTACGTGTGGCTGGTCGGCGAGCGCGAGATC
----------+----------+----------+----------+----------+----------+1860
CGGCGCTACGACTTGTACTGCCCGAGGCCCATGCACACCGACCAGCCGCTCGCGCTCTAG

S  G  N  A  L  R  Y  A  P  D  G  I  L  G  L  Q  L  I  N  G  256
TCGGGGAACGCCCTGCGCTACGCCCCAGACGGCATCCTCGGGCTGCAGCTCATCAACGGC
----------+----------+----------+----------+----------+----------+1920
AGCCCCTTGCGGGACGCGATGCGGGGTCTGCCGTAGGAGCCCGACGTCGAGTAGTTGCCG

K  N  E  S  A  H  I  S  D  A  V  G  V  V  A  Q  A  V  H  E  276
AAGAACGAGTCGGCCCACATCAGCGACGCCGTGGGCGTGGTGGCCCAGGCCGTGCACGAG
----------+----------+----------+----------+----------+----------+1980
TTCTTGCTCAGCCGGGTGTAGTCGCTGCGGCACCCGCACCACCGGGTCCGGCACGTGCTC
```

FIG. 6F

```
         L   L   E   K   E   N   I   T   D   P   P   R   G   C   V   G   N   T   N   I   296
     CTCCTCGAGAAGGAGAACATCACCGACCCGCCGCGGGGCTGCGTGGGCAACACCAACATC
     ----------+---------+---------+---------+---------+---------+2040
     GAGGAGCTCTTCCTCTTGTAGTGGCTGGGCGGCGCCCCGACGCACCCGTTGTGGTTGTAG

W   K   T   G   P   L   F   K   R   V   L   M   S   S   K   Y   A   D   G   V   316
     TGGAAGACCGGGCCGCTCTTCAAGAGAGTGCTGATGTCTTCCAAGTATGCGGATGGGGTG
     ----------+---------+---------+---------+---------+---------+2100
     ACCTTCTGGCCCGGCGAGAAGTTCTCTCACGACTACAGAAGGTTCATACGCCTACCCCAC

T   G   R   V   E   F   N   E   D   G   D   R   K   F   A   N   Y   S   I   M   336
     ACTGGTCGCGTGGAGTTCAATGAGGATGGGGACCGGAAGTTCGCCAACTACAGCATCATG
     ----------+---------+---------+---------+---------+---------+2160
     TGACCAGCGCACCTCAAGTTACTCCTACCCCTGGCCTTCAAGCGGTTGATGTCGTAGTAC

N   L   Q   N   R   K   L   V   Q   V   G   I   Y   N   G   T   H   V   I   P   356
     AACCTGCAGAACCGCAAGCTGGTGCAAGTGGGCATCTACAATGGCACCCACGTCATCCCT
     ----------+---------+---------+---------+---------+---------+2220
     TTGGACGTCTTGGCGTTCGACCACGTTCACCCGTAGATGTTACCGTGGGTGCAGTAGGGA

N   D   R   K   I   I   W   P   G   G   E   T   E   K   P   R   G   Y   Q   M   376
     AATGACAGGAAGATCATCTGGCCAGGCGGAGAGACAGAGAAGCCTCGAGGGTACCAGATG
     ----------+---------+---------+---------+---------+---------+2280
     TTACTGTCCTTCTAGTAGACCGGTCCGCCTCTCTGTCTCTTCGGAGCTCCCATGGTCTAC

S   T   R   L   K   I   V   T   I   H   Q   E   P   F   V   Y   V   K   P   T   396
     TCCACCAGACTGAAGATTGTGACGATCCACCAGGAGCCCTTCGTGTACGTCAAGCCCACG
     ----------+---------+---------+---------+---------+---------+2340
     AGGTGGTCTGACTTCTAACACTGCTAGGTGGTCCTCGGGAAGCACATGCAGTTCGGGTGC
```

FIG. 6G

```
     L  S  D  G  T  C  K  E  E  F  T  V  N  G  D  P  V  K  K  V  416
     CTGAGTGATGGGACATGCAAGGAGGAGTTCACAGTCAACGGCGACCCAGTCAAGAAGGTG
     ----------+---------+---------+---------+---------+---------+2400
     GACTCACTACCCTGTACGTTCCTCCTCAAGTGTCAGTTGCCGCTGGGTCAGTTCTTCCAC

I  C  T  G  P  N  D  T  S  P  G  S  P  R  H  T  V  P  Q  C  436
     ATCTGCACCGGGCCCAACGACACGTCGCCGGGCAGCCCCCGCCACACGGTGCCTCAGTGT
     ----------+---------+---------+---------+---------+---------+2460
     TAGACGTGGCCCGGGTTGCTGTGCAGCGGCCCGTCGGGGGCGGTGTGCCACGGAGTCACA

C  Y  G  F  C  I  D  L  L  I  K  L  A  R  T  M  N  F  T  Y  456
     TGCTACGGCTTTTGCATCGACCTGCTCATCAAGCTGGCACGGACCATGAACTTCACCTAC
     ----------+---------+---------+---------+---------+---------+2520
     ACGATGCCGAAAACGTAGCTGGACGAGTAGTTCGACCGTGCCTGGTACTTGAAGTGGATG

E  V  H  L  V  A  D  G  K  F  G  T  Q  E  R  V  N  N  S  N  476
     GAGGTGCACCTGGTGGCAGATGGCAAGTTCGGCACACAGGAGCGGGTGAACAACAGCAAC
     ----------+---------+---------+---------+---------+---------+2580
     CTCCACGTGGACCACCGTCTACCGTTCAAGCCGTGTGTCCTCGCCCACTTGTTGTCGTTG

K  K  E  W  N  G  M  M  G  E  L  L  S  G  Q  A  D  M  I  V  496
     AAGAAGGAGTGGAATGGGATGATGGGCGAGCTGCTCAGCGGGCAGGCAGACATGATCGTG
     ----------+---------+---------+---------+---------+---------+2640
     TTCTTCCTCACCTTACCCTACTACCCGCTCGACGAGTCGCCCGTCCGTCTGTACTAGCAC

A  P  L  T  I  N  N  E  R  A  Q  Y  I  E  F  S  K  P  F  K  516
     GCGCCGCTAACCATAAACAACGAGCGCGCGCAGTACATCGAGTTTTCCAAGCCCTTCAAG
     ----------+---------+---------+---------+---------+---------+2700
     CGCGGCGATTGGTATTTGTTGCTCGCGCGCGTCATGTAGCTCAAAAGGTTCGGGAAGTTC
```

FIG. 6H

```
        Y  Q  G  L  T  I  L  V  K  K  E  I  P  R  S  T  L  D  S  F   536
     TACCAGGGCCTGACTATTCTGGTCAAGAAGGAGATTCCCCGGAGCACGCTGGACTCGTTC
     ----------+----------+----------+----------+----------+----------+2760
     ATGGTCCCGGACTGATAAGACCAGTTCTTCCTCTAAGGGGCCTCGTGCGACCTGAGCAAG

|-----------------TM-1-------------------
        M  Q  P  F  Q  S  T  L  W  L  L  V  G  L  S  V  H  V  V  A   556
     ATGCAGCCGTTCCAGAGCACACTGTGGCTGCTGGTGGGGCTGTCGGTGCACGTGGTGGCC
     ----------+----------+----------+----------+----------+----------+2820
     TACGTCGGCAAGGTCTCGTGTGACACCGACGACCACCCCGACAGCCACGTGCACCACCGG

-----------------|
        V  M  L  Y  L  L  D  R  F  S  P  F  G  R  F  K  V  N  S  E   576
     GTGATGCTGTACCTGCTGGACCGCTTCAGCCCCTTCGGCCGGTTCAAGGTGAACAGCGAG
     ----------+----------+----------+----------+----------+----------+2880
     CACTACGACATGGACGACCTGGCGAAGTCGGGGAAGCCGGCCAAGTTCCACTTGTCGCTC

|------------------TM-2--------------------
        E  E  E  E  D  A  L  T  L  S  S  A  M  W  F  S  W  G  V  L   596
     GAGGAGGAGGAGGACGCACTGACCCTGTCCTCGGCCATGTGGTTCTCCTGGGGCGTCCTG
     ----------+----------+----------+----------+----------+----------+2940
     CTCCTCCTCCTCCTGCGTGACTGGGACAGGAGCCGGTACACCAAGAGGACCCCGCAGGAC

-----------------|                              |------------
        L  N  S  G  I  G  E  G  A  P  R  S  F  S  A  R  I  L  G  M   616
     CTCAACTCCGGCATCGGGGAAGGCGCCCCCAGAAGCTTCTCAGCGCGCATCCTGGGCATG
     ----------+----------+----------+----------+----------+----------+3000
     GAGTTGAGGCCGTAGCCCCTTCCGCGGGGGTCTTCGAAGAGTCGCGCGTAGGACCCGTAC
```

FIG. 61

```
--------TM-3--------------------------------|
  V   W   A   G   F   A   M   I   I   V   A   S   Y   T   A   N   L   A   A   F  636
GTGTGGGCCGGCTTTGCCATGATCATCGTGGCCTCCTACACCGCCAACCTGGCGGCCTTC
----------+---------+---------+---------+---------+---------+3060
CACACCCGGCCGAAACGGTACTAGTAGCACCGGAGGATGTGGCGGTTGGACCGCCGGAAG

L   V   L   D   R   P   E   E   R   I   T   G   I   N   D   P   R   L   R   N  656
CTGGTGCTGGACCGGCCGGAGGAGCGCATCACGGGCATCAACGACCCTCGGCTGAGGAAC
----------+---------+---------+---------+---------+---------+3120
GACCACGACCTGGCCGGCCTCCTCGCGTAGTGCCCGTAGTTGCTGGGAGCCGACTCCTTG

P   S   D   K   F   I   Y   A   T   V   K   Q   S   S   V   D   I   Y   F   R  676
CCCTCGGACAAGTTTATCTACGCCACGGTGAAGCAGAGCTCCGTGGATATCTACTTCCGG
----------+---------+---------+---------+---------+---------+3180
GGGAGCCTGTTCAAATAGATGCGGTGCCACTTCGTCTCGAGGCACCTATAGATGAAGGCC

R   Q   V   E   L   S   T   M   Y   R   H   M   E   K   H   N   Y   E   S   A  696
CGCCAGGTGGAGCTGAGCACCATGTACCGGCATATGGAGAAGCACAACTACGAGAGTGCG
----------+---------+---------+---------+---------+---------+3240
GCGGTCCACCTCGACTCGTGGTACATGGCCGTATACCTCTTCGTGTTGATGCTCTCACGC

A   E   A   I   Q   A   V   R   D   N   K   L   H   A   F   I   W   D   S   A  716
GCGGAGGCCATCCAGGCCGTGAGAGACAACAAGCTGCATGCCTTCATCTGGGACTCGGCG
----------+---------+---------+---------+---------+---------+3300
CGCCTCCGGTAGGTCCGGCACTCTCTGTTGTTCGACGTACGGAAGTAGACCCTGAGCCGC

V   L   E   F   E   A   S   Q   K   C   D   L   V   T   T   G   E   L   F   F  736
GTGCTGGAGTTCGAGGCCTCGCAGAAGTGCGACCTGGTGACGACTGGAGAGCTGTTTTTC
----------+---------+---------+---------+---------+---------+3360
CACGACCTCAAGCTCCGGAGCGTCTTCACGCTGGACCACTGCTGACCTCTCGACAAAAAG
```

FIG. 6J

```
        R   S   G   F   G   I   G   M   R   K   D   S   P   W   K   Q   N   V   S   L   756
     CGCTCGGGCTTCGGCATAGGCATGCGCAAAGACAGCCCCTGGAAGCAGAACGTCTCCCTG
     ----------+----------+----------+----------+----------+----------+3420
     GCGAGCCCGAAGCCGTATCCGTACGCGTTTCTGTCGGGGACCTTCGTCTTGCAGAGGGAC

S   I   L   K   S   H   E   N   G   F   M   E   D   L   D   K   T   W   V   R   776
     TCCATCCTCAAGTCCCACGAGAATGGCTTCATGGAAGACCTGGACAAGACGTGGGTTCGG
     ----------+----------+----------+----------+----------+----------+3480
     AGGTAGGAGTTCAGGGTGCTCTTACCGAAGTACCTTCTGGACCTGTTCTGCACCCAAGCC

|------
        Y   Q   E   C   D   S   R   S   N   A   P   A   T   L   T   F   E   N   M   A   796
     TATCAGGAATGTGACTCGCGCAGCAACGCCCCTGCGACCCTTACTTTTGAGAACATGGCC
     ----------+----------+----------+----------+----------+----------+3540
     ATAGTCCTTACACTGAGCGCGTCGTTGCGGGGACGCTGGGAATGAAAACTCTTGTACCGG

-----------------TM-4----------------------------------|
        G   V   F   M   L   V   A   G   G   I   V   A   G   I   F   L   I   F   I   E   816
     GGGGTCTTCATGCTGGTAGCTGGGGGCATCGTGGCCGGGATCTTCCTGATTTTCATCGAG
     ----------+----------+----------+----------+----------+----------+3600
     CCCCAGAAGTACGACCATCGACCCCCGTAGCACCGGCCCTAGAAGGACTAAAAGTAGCTC

I   A   Y   K   R   H   K   D   A   R   R   K   Q   M   Q   L   A   F   A   A   836
     ATTGCCTACAAGCGGCACAAGGATGCTCGCCGGAAGCAGATGCAGCTGGCCTTTGCCGCC
     ----------+----------+----------+----------+----------+----------+3660
     TAACGGATGTTCGCCGTGTTCCTACGAGCGGCCTTCGTCTACGTCGACCGGAAACGGCGG

V   N   V   W   R   K   N   L   Q   Q   Y   H   P   T   D   I   T   G   P   L   856
     GTTAACGTGTGGCGGAAGAACCTGCAGCAGTACCATCCCACTGATATCACGGGCCCGCTC
     ----------+----------+----------+----------+----------+----------+3720
     CAATTGCACACCGCCTTCTTGGACGTCGTCATGGTAGGGTGACTATAGTGCCCGGGCGAG
```

FIG. 6K

```
         N   L   S   D   P   S   V   S   T   V   V  (SEQ ID NO:11)              867
       AACCTCTCAGATCCCTCGGTCAGCACCGTGGTGTGAGGCCCCCGGAGGCGCCCACCTGCC
       ----------+----------+----------+----------+----------+----------+3780
       TTGGAGAGTCTAGGGAGCCAGTCGTGGCACCACACTCCGGGGGCCTCCGCGGGTGGACGG

CAGTTAGCCCGGCCAAGGACACTGATGGGTCCTGCTGCTCGGGAAGGCCTGAGGGAAGCC
       ----------+----------+----------+----------+----------+----------+3840
       GTCAATCGGGCCGGTTCCTGTGACTACCCAGGACGACGAGCCCTTCCGGACTCCCTTCGG

CACCCGCCCCAGAGACTGCCCACCCTGGGCCTCCCGTCCGTCCGCCCGCCCACCCCGCTG
       ----------+----------+----------+----------+----------+----------+3900
       GTGGGCGGGGTCTCTGACGGGTGGGACCCGGAGGGCAGGCAGGCGGGCGGGTGGGGCGAC

CCTGGCGGGCAGCCCCTGCTGGACCAAGGTGCGGACCGGAGCGGCTGAGGACGGGGCAGA
       ----------+----------+----------+----------+----------+----------+3960
       GGACCGCCCGTCGGGGACGACCTGGTTCCACGCCTGGCCTCGCCGACTCCTGCCCCGTCT

GCTGAGTCGGCTGGGCAGGGCGCAGGGCGCTCCGGCAGAGGCAGGGCCCTGGGGTCTCTG
       ----------+----------+----------+----------+----------+----------+4020
       CGACTCAGCCGACCCGTCCCGCGTCCCGCGAGGCCGTCTCCGTCCCGGGACCCCAGAGAC

AGCAGTGGGGAGCGGGGGCTAACTGGCCCCAGGCGAAGGGGCTTGGAGCAGAGACGGCAG
       ----------+----------+----------+----------+----------+----------+4080
       TCGTCACCCCTCGCCCCCGATTGACCGGGGTCCGCTTCCCCGAACCTCGTCTCTGCCGTC

CCCCATCCTTCCCGCAGCACCAGCCTGAGCCACAGTGGGGCCCATGGCCCCAGCTGGCTG
       ----------+----------+----------+----------+----------+----------+4140
       GGGGTAGGAAGGGCGTCGTGGTCGGACTCGGTGTCACCCCGGGTACCGGGGTCGACCGAC

GGTCGCCCCTCCTCGGGCGCCTGCGCTCCTCTGCAGCCTGAGCTCCACCCTCCCCTCTTC
       ----------+----------+----------+----------+----------+----------+4200
       CCAGCGGGGAGGAGCCCGCGGACGCGAGGAGACGTCGGACTCGAGGTGGGAGGGGAGAAG
```

FIG. 6L

```
TTGCGGCACCGCCCACCCACACCCCGTCTGCCCCTTGACCCCACACGCCGGGGCTGGCCC
----------+----------+----------+----------+----------+----------+4260
AACGCCGTGGCGGGTGGGTGTGGGGCAGACGGGGAACTGGGGTGTGCGGCCCCGACCGGG

TGCCCTCCCCCACGGCCGTCCCTGACTTCCCAGCTGGCAGCGCCTCCCGCCGCCTCGGGC
----------+----------+----------+----------+----------+----------+4320
ACGGGAGGGGGTGCCGGCAGGGACTGAAGGGTCGACCGTCGCGGAGGGCGGCGGAGCCCG

CGCCTCCTCCAGACTCGAGAGGGCTGAGCCCCTCCTCTCCTCGTCCGGCCTGCAGCCCAG
----------+----------+----------+----------+----------+----------+4380
GCGGAGGAGGTCTGAGCTCTCCCGACTCGGGGAGGAGAGGAGCAGGCCGGACGTCGGGTC

AACGGGCCTCCCCGGGGGTCCCCGGACGCTGGCTCGGGACTGTCTTCAACCCTGCCCTGC
----------+----------+----------+----------+----------+----------+4440
TTGCCCGGAGGGGCCCCCAGGGGCCTGCGACCGAGCCCTGACAGAAGTTGGGACGGGACG

ACCTTGGGCACGGGAGAGCGCCACCCGCCCGCCCCCGCCCTCGCTCCGGGTGCGTGACCG
----------+----------+----------+----------+----------+----------+4500
TGGAACCCGTGCCCTCTCGCGGTGGGCGGGCGGGGCGGGAGCGAGGCCCACGCACTGGC

GCCCGCCACCTTGTACAGAACCAGCACTCCCAGGGCCCGAGCGCGTGCCTTCCCCGTGCG
----------+----------+----------+----------+----------+----------+4560
CGGGCGGTGGAACATGTCTTGGTCGTGAGGGTCCCGGGCTCGCGCACGGAAGGGGCACGC

GCCCGTGCGCAGCCGCGCTCTGCCCCTCCGTCCCCAGGGTGCAGGCGCGCACCGCCCAAC
----------+----------+----------+----------+----------+----------+4620
CGGGCACGCGTCGGCGCGAGACGGGGAGGCAGGGGTCCCACGTCCGCGCGTGGCGGGTTG
```

Eco RI

```
CCCCACCTCCCCGGTGTATGCAGTGGTGATGCCGGAATTC            (SEQ ID NO:10)
----------+----------+----------+---------4659
GGGGTGGAGGGCCACATACGTCACCACTACGGCCTTAAG
```

FIG. 7A

```
3675 GAAGAACCTGCAG............................................ 3687  1
     |||||||||||||
     |||||||||||||
3675 GAAGAACCTGCAG............................................ 3687  2
     |||||||||||||
     |||||||||||||
3675 GAAGAACCTGCAGGATAGAAAGAGTGGTAGAGCAGAGCCTGACCCTAAAAAGAAAGCCAC +47  3A
     ||||||||||||||||||||||||||||||||||||||||||||||||||||||||||||
     ||||||||||||||||||||||||||||||||||||||||||||||||||||||||||||
3675 GAAGAACCTGCAGGATAGAAAGAGTGGTAGAGCAGAGCCTGACCCTAAAAAGAAAGCCAC +47  3C

............................................................  1
     ............................................................  2
     ATTTAGGGCTATCACCTCCACCCTGGCTTCCAGCTTCAAGAGGCGTAGGTCCTCCAAAGA +107 3A
     ||||||||||||||||||||||||||||||||||||||||||||||||||||||||||||
     ||||||||||||||||||||||||||||||||||||||||||||||||||||||||||||
     ATTTAGGGCTATCACCTCCACCCTGGCTTCCAGCTTCAAGAGGCGTAGGTCCTCCAAAGA +107 3C

............................................................  1
     ....AGCACCGGGGGTGGACGCGGCGCTTTGCAAAACCAAAAAGACACAGTGCTGCCGCG +56   2
         ||||||||||||||||||||||||||||||||||||||||||||||||||||||||
         ||||||||||||||||||||||||||||||||||||||||||||||||||||||||
     CACGAGCACCGGGGGTGGACGCGGCGCTTTGCAAAACCAAAAAGACACAGTGCTGCCGCG +167 3A
     ||||||||||||||||||||||||||||||||||||||||||||||||||||||||||||
     ||||||||||||||||||||||||||||||||||||||||||||||||||||||||||||
     CACGAGCACCGGGGGTGGACGCGGCGCTTTGCAAAACCAAAAAGACACAGTGCTGCCGCG +167 3C

............................................................  1
     ACGCGCTATTGAGAGGGAGGAGGGCCAGCTGCAGCTGTGTTCCCGTCATAGGGAGAGCTG +116  2
     ||||||||||||||||||||||||||||||||||||||||||||||||||||||||||||
     ||||||||||||||||||||||||||||||||||||||||||||||||||||||||||||
     ACGCGCTATTGAGAGGGAGGAGGGCCAGCTGCAGCTGTGTTCCCGTCATAGGGAGAGCTG +227 3A
     ||||||||||||||||||||||||||||||||||||||||||||||||||||| |||||||
     ||||||||||||||||||||||||||||||||||||||||||||||||||||| |||||||
     ACGCGCTATTGAGAGGGAGGAGGGCCAGCTGCAGCTGTGTTCCCGTCATACGGAGAGCTG +227 3C
                                                         *     END
```

FIG. 7B

```
                .         .         .         .         .         .
          .........................................................     1
          AGACTCCCCGCCCGCCCTCCTCTGCCCCCTCCCCCGCAGACAGACAGACAGACGGATGGG  +176  2
          ||||||||||||||||||||||||||||||||||||||||||||||||||||||||||||
          ||||||||||||||||||||||||||||||||||||||||||||||||||||||||||||
          AGACTCCCCGCCCGCCCTCCTCTGCCCCCTCCCCCGCAGACAGACAGACAGACGGATGGG  +287  3A
          ||||||||||||||||||||||||||||||||||||||||||||||||||||||||||||
          ||||||||||||||||||||||||||||||||||||||||||||||||||||||||||||
          AGACTCCCCGCCCGCCCTCCTCTGCCCCCTCCCCCGCAGACAGACAGACAGACGGATGGG  +287  3C

.         .         .         .         .         .
          .........................................................     1
          ACAGCGGCCCGGCCCACGCAGAGCCCCGGAGCACCACGGGGTCGGGGGAGGAGCACCCCC  +236  2
          ||||||||||||||||||||||||||||||||||||||||||||||||||||||||||||
          ||||||||||||||||||||||||||||||||||||||||||||||||||||||||||||
          ACAGCGGCCCGGCCCACGCAGAGCCCCGGAGCACCACGGGGTCGGGGGAGGAGCACCCCC  +347  3A
          ||||||||||||||||||||||||||||||||||||||||||||||||||||||||||||
          ||||||||||||||||||||||||||||||||||||||||||||||||||||||||||||
          ACAGCGGCCCGGCCCACGCAGAGCCCCGGAGCACCACGGGGTCGGGGGAGGAGCACCCCC  +347  3C

.         .         .         .         .         .
          .........................................................     1
          AGCCTCCCCCAGGCTGCGCCTGCCCGCCCGCCGGTTGGCCGGCTGGCCGGTCCACCCCGT  +296  2
          ||||||||||||||||||||||||||||||||||||||||||||||||||||||||||||
          ||||||||||||||||||||||||||||||||||||||||||||||||||||||||||||
          AGCCTCCCCCAGGCTGCGCCTGCCCGCCCGCCGGTTGGCCGGCTGGCCGGTCCACCCCGT  +407  3A
          ||||||||||||||||||||||||||||||||||||||||||||||||||||||||||||
          ||||||||||||||||||||||||||||||||||||||||||||||||||||||||||||
          AGCCTCCCCCAGGCTGCGCCTGCCCGCCCGCCGGTTGGCCGGCTGGCCGGTCCACCCCGT  +407  3C

.         .         .         .         .         .
          .........................................................     1
          CCCGGCCCCGCGCGTGCCCCCAGCGTGGGGCTAACGGGCGCCTTGTCTGTGTATTTCTAT  +356  2
          ||||||||||||||||||||||||||||||||||||||||||||||||||||||||||||
          ||||||||||||||||||||||||||||||||||||||||||||||||||||||||||||
          CCCGGCCCCGCGCGTGCCCCCAGCGTGGGGCTAACGGGCGCCTTGTCTGTGTATTTCTAT  +467  3A
          ||||||||||||||||||||||||||||||||||||||||||||||||||||||||||||
          ||||||||||||||||||||||||||||||||||||||||||||||||||||||||||||
          CCCGGCCCCGCGCGTGCCCCCAGCGTGGGGCTAACGGGCGCCTTGTCTGTGTATTTCTAT  +467  3C

.         .
     3688 .......CAGTACCATCCCACT  3702  humNMDAR1-1   (SEQ ID NO:12)
                ||||||||||||||||
     +357 TTTGCAGCAGTACCATCCCACT  4065  humNMDAR1-2   (SEQ ID NO:13)
          ||||||||||||||||||||||
     +468 TTTGCAGCAGTACCATCCCACT  4176  humNMDAR1-3A  (SEQ ID NO:14)
          ||||||||||||||||||||||
     +468 TTTGCAGCAGTACCATCCCACT  4176  humNMDAR1-3C  (SEQ ID NO:15)
```

FIG. 8

NMDAR1-1

```
803 AGGIVAGIFLIFIEIAYKRHKDARRKQMLAFAAVNVWRKNLQ............ 845
    |||||||||||||||||||||||||||||||||||||||||
803 AGGIVAGIFLIFIEIAYKRHKDARRKQMLAFAAVNVWRKNLQDRKSGRAEPDPKKKATF 862
```

NMDAR1-4

NMDAR1-1 (cont'd)

```
846 ................................QYHPTDITGPLNLSDPSVSTVV 867  (SEQ ID NO:16)
                                    |||||||||||||||||||||
863 RAITSTLASSFKRRRSSKDTQYHPTDITGPLNLSDPSVSTVV 904  (SEQ ID NO:17)
```

NMDAR1-4 (cont'd)

FIG. 9

```
                                                              NMDAR1-5/6/7/8
                       <--- 21 aa insert --->
160  KRLETLLEERESKSKKRNYENLDQLSYDNKRGPKAEKVLQFDPGTKN  206   (SEQ ID NO:19)
     |||||||||||||||                  ||||||||||||||||
160  KRLETLLEERESK.....................AEKVLQFDPGTKN  185   (SEQ ID NO:18)
                                                              NMDAR1-1/2/3/4
```

IONOTROPIC HUMAN GLUTAMATE RECEPTOR SUBUNIT NR3

CROSS-REFERENCE TO RELATED APPLICATIONS

This application is a-continuation-in-part of U.S. patent application Ser. No. 07/987,953, filed Dec. 11, 1992 now abandoned.

FIELD OF THE INVENTION

This invention relates to the application of recombinant DNA technology in the field of neurobiology. More particularly, the invention relates to the cloning and expression of DNA coding for proteins which modulate the function of glutamate receptors.

BACKGROUND TO THE INVENTION

In the mammalian central nervous system (CNS), the transmission of nerve impulses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Members of the EAA receptor family can be grouped into three main types based on differential binding to certain glutamate analogs. One type of EAA receptor, which in addition to glutamate also binds the compound NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate (2-carboxy-4-(1-methylethenyl)-3-pyrrolidineacetate). Accordingly, receptors which bind glutamate but not NMDA, and which bind with greater affinity to kainate than to AMPA, are referred to as kainate-type EAA receptors. Similarly, those EAA receptors which bind glutamate but not NMDA, and which bind AMPA with greater affinity than kainate are referred to as AMPA-type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. The development of therapeutics which modulate these processes is being slowed by the lack of any homogeneous source of receptor material with which to discover selectively binding drug molecules, which interact specifically at the interface of an appropriate EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor cDNA, a substrate which is homogeneous for the desired receptor is provided, for drug screening programs.

Non-human cDNAs which appear to encode the NMDA-type of EAA receptor have recently been identified and isolated. A cDNA encoding a subunit polypeptide of an NMDA receptor in rat, designated NR1, has been isolated as described by Moriyoshi et al. in Nature 354: 31, 1991. An extension of this work has revealed seven isoforms of NR1, presumably generated by combinations of alternative RNA splicing in the amino- and carboxy-terminal regions of NR1 (Anantharam et al. FEBS Lett. 305: 27, 1992; Durand et al. Proc. Nati. Acad. Sci. USA 89: 9359, 1992; Nakanishi et al. Proc. Natl. Acad. Sci. USA 89: 8552, 1992; Sugihara et al. Biochem, Biophys. Res. Commun. 185; 826, 1992; Hollmann et al. Neuron 10; 943, 1993; Kusiak and Norton. Mol. Brain. Res. 20: 64, 1993). DNA encoding NR1 and one of its isoforms have also been cloned from mouse brain by Yamazaki et at. as described in FEBS Lett. 300: 39, 1992. Other rat NMDA receptor subunits, designated NR2A, NR2B, NR2C and NR2D, have also been identified (Monyer et al. Science 256: 1217, 1992; Ishii et al. J. Biol. Chem. 268: 2836, 1993), as well as mouse NMDA receptor subunits which have been designated $\epsilon 1$, $\epsilon 2$, $\epsilon 3$ and $\epsilon 4$ (Meguro et al. Nature 357: 70, 1992; Kutsuwada et al. Nature 358: 36, 1992; Ikeda et al. FEBS Lett. 313: 34, 1992).

There has emerged from these molecular cloning advances, a better understanding of the structural features of NMDA receptors and their subunits, as they exist in the non-human brain. According to the current model, each NMDA receptor is heteromeric, consisting of individual membrane-anchored subunits, each comprising transmembrane regions and extracellular domains that dictate ligand-binding properties and contribute to the ion-gating function served by the receptor complex.

In the search for therapeutics useful to treat CNS disorders in humans, it is highly desirable to obtain knowledge of human EAA receptors, and proteins which modulate the activity of these receptors. Such an understanding would provide a means to screen for compounds that selectively interact with this activity, i.e. to stimulate or inhibit receptor activity, thereby providing a means to identify compounds having potential therapeutic utility in humans. Non-human mammalian models are not suitable for this purpose despite significant protein homology due to the fact that minute sequence discrepancies have been found to cause dramatic pharmacological and functional variation between species homologues of the same protein (Oksenberg et al., Nature, 360:161, 1992; Hall et al. Trends Pharmacol. Sci. 14: 376, 1993). It is therefore particularly desirable to provide cloned cDNA encoding human EAA receptor proteins or modulatory proteins thereof, and cell lines expressing these proteins, in order to generate a screening method for a, compounds therapeutically useful in humans. These, accordingly, are objects of the present invention.

SUMMARY OF THE INVENTION

Human cDNAs encoding NMDA receptor modulatory proteins have been identified and characterized, and include proteins referred to herein as the NR3 and NR4 modulatory proteins. Specifically encompassed are parent proteins designated the NR3-1 and NR4-1 proteins, as well as functional sequence-related variants of NR3-1 and NR4-1, and functional fragments of NR3-1 and NR4-1.

In one of its aspects, thus, the present invention provides an isolated polynucleotide, consisting either of DNA or of RNA, which codes for a human NR3 protein, or functional fragments thereof.

In another aspect of the present invention, there is provided a cell that has been genetically engineered to produce a human EAA receptor modulatory protein belonging to the herein-defined NRS family. In related aspects of the present invention, there are provided recombinant DNA constructs and methods useful to obtain substantially homogeneous sources of the human NR3 protein, comprising the steps of culturing the genetically engineered cells, and then recovering the cultured cells.

In another aspect of the present invention, there is provided a method for evaluating interaction between a candidate ligand and a human EAA receptor modulatory protein, which comprises the steps of incubating the candidate ligand with a genetically engineered cell as described above, or with a membrane preparation derived therefrom, and then assessing said interaction by determining the extent of protein/ligand binding, or by determining the ligand-induced electrical current across said cell.

In yet another aspect of the present invention, a cell that has been engineered genetically to produce a human heteromeric NR3/receptor complex comprising an NR3 protein and an NMDA receptor is provided.

In a further aspect of the present invention, there is provided a method for evaluating interaction between a candidate ligand and a human heteromeric NR3/receptor complex comprising an NR3 protein and an NMDA receptor, said method comprising the steps of incubating the candidate ligand with a cell line engineered to produce said receptor complex, or with a membrane preparation derived therefrom, and then assessing the interaction therebetween by determining the extent of protein/ligand binding, or by determining the ligand-induced electrical current across said cell.

Other aspects of the present invention include a human NR3 protein, in a form essentially free from other proteins of human origin, functional and immunogenic fragments of the protein, antibodies which bind to the protein, and oligonucleotides which hybridize to nucleic acid encoding the protein.

Other aspects of the present invention, which encompass various applications of the discoveries herein described, will become apparent from the following detailed description, and from the accompanying drawings in which:

BRIEF REFERENCE TO THE DRAWINGS

FIG. 1 provides the nucleotide sequence (SEQ ID NO: 1) of DNA encoding an NR3 modulatory protein, and the deduced amino acid sequence (SEQ ID NO: 2) thereof;

FIGS. 2A and 2B illustrate, with plasmid maps, the strategy used to construct expression vectors harbouring the DNA sequence illustrated in FIG. 1;

FIG. 3 provides, with reference to FIG. 1, the partial DNA and amino acid sequences (SEQ ID NOs: 5 & 6) of a naturally occurring variant of the modulatory protein illustrated in FIG. 1; (represented here by partial DNA and amino acid sequences SEQ ID NOS 3 and 4).

Figure 10:
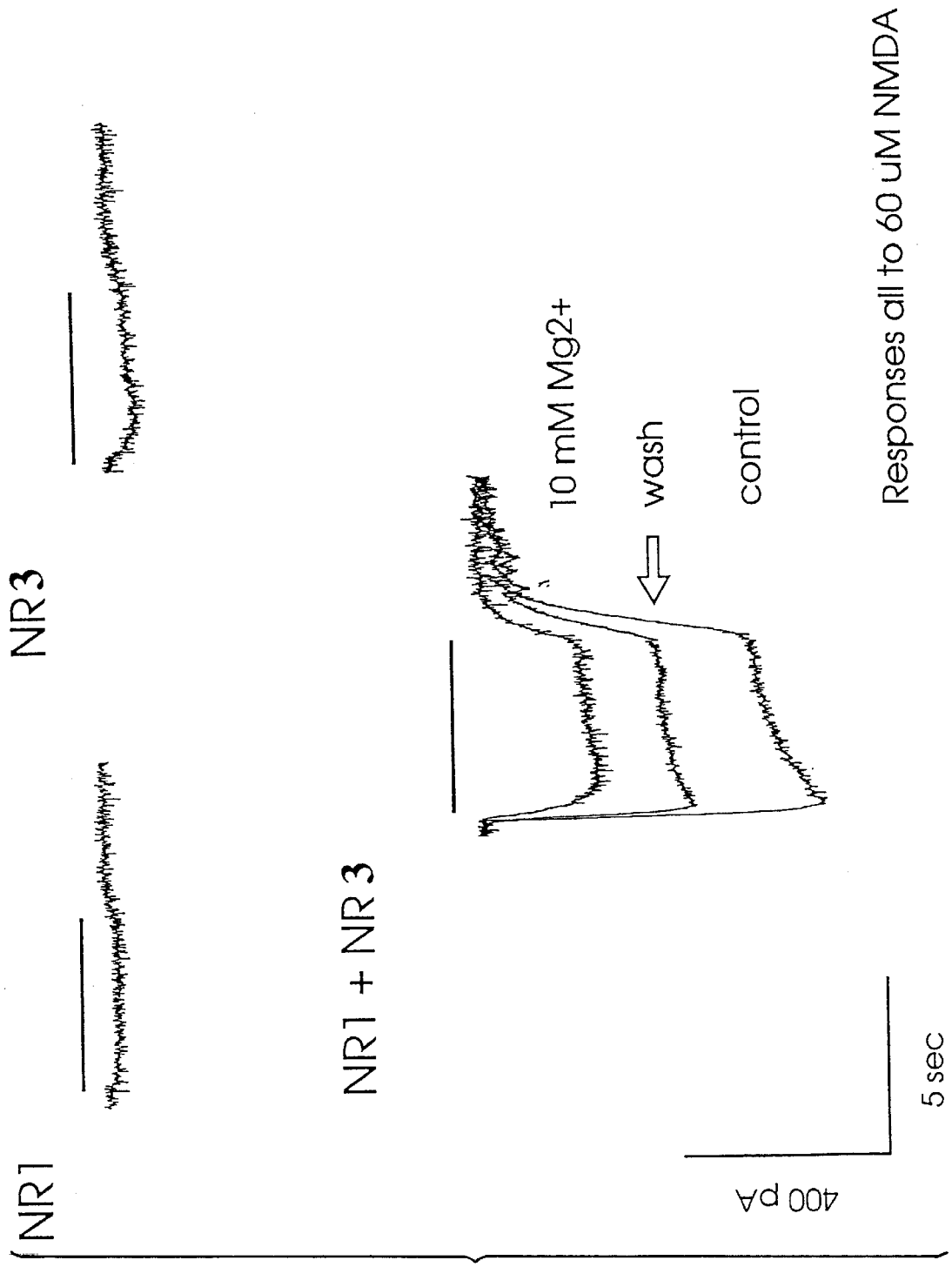

FIG. 4 provides the partial nucleotide sequence (SEQ ID NO: 7) of DNA encoding an NR4 modulatory protein, and the deduced amino acid sequence (SEQ ID NO: 8) thereof;

FIG. 5 provides the nucleotide sequence (SEQ ID NO: 9) of DNA encoding the NR2A-1 probe;

FIG. 6 provides the nucleotide sequence (SEQ ID NO: 10) of DNA encoding the NMDAR1-1 receptor, and the deduced amino acid sequence (SEQ ID NO: 11) thereof;

FIG. 7 provides a comparison of partial nucleotide sequences of NMDAR1-1 (SEQ ID NO:12) with its variants, NMDAR1-2, NMDAR1-3A and NMDAR1-3C (SEQ ID NOs:13, 14 & 15, respectively);

FIG. 8 provides a comparison of the amino acid sequences of NMDAR1-1 (SEQ ID NO: 16) and NMDAR1-4 (SEQ ID NO: 17);

FIG. 9 provides a comparison of the amino acid sequences of NMDAR1-1/2/3/4 (SEQ ID NO: 18) and NMDAR1-5/6/7/8 (SEQ ID NO: 19); and FIG. 10 graphically illustrates electrophysiological properties of a heteromeric complex comprising NR3-1 and NMDAR1-3C.

DETAILED DESCRIPTION OF THE INVENTION AND ITS PREFERRED EMBODIMENTS

The present invention relates to modulatory proteins of excitatory amino acid (EAA) receptors of human origin, and to isolated polynucleotides encoding them. More particularly, the present invention is directed to novel human modulatory proteins, herein designated the NR3 and NR4 EAA receptor modulatory proteins, which modulate the activity of human EAA receptors of the NMDA-type. The NRS and NR4 modulatory proteins comprise the NR3-1 and NR4-1 parent proteins, as well as functional sequence-related variants of the human NR3-1 protein and functional fragments of the NR3-1 protein.

As used herein, the term "modulatory protein" refers to a protein that, when combined with a human EAA receptor, and in particular with a human NMDA receptor, forms a heteromeric receptor complex having electrophysiological properties which are distinct from the electrophysiological properties of a homomeric receptor complex formed from the selected NMDA receptor alone. Thus, the NR3 and NR4 proteins of the present invention have been found to modulate the ion channel activity of NMDA-type receptors, i.e. receptors having a ligand binding profile comprising specific binding affinity for glutamate, NMDA and MK-801 [(+)-5-methyl-10,11-dihydro-5H-dibenzo[a,d]cyclohepten-5,10-imine maleate]. The electrophysiological properties, or ion channel activity, of EAA receptors is typically determined using established electrophysiological assays appropriate for detecting conductance across a cell membrane such as the assay described by Hollmann et al. in Nature 342: 643.

The term "isolated" as it is used herein with respect to NR3-encoding polynucleotides refers to polynucleotides which are free from human DNA which encodes, or partially encodes, CNS proteins other than NR3 proteins and NMDA receptor proteins.

The term "heteromeric receptor complex" is used to refer to a receptor complex comprising a modulatory protein, in accordance with the present invention, and an NMDA receptor. A "heteromeric NR3/receptor complex" refers to a receptor complex comprising an NR3 modulatory protein and an NMDA receptor.

Variants of the NR3-1 and NR4-1 parent modulatory proteins also form modulatory proteins as defined above. Specifically included are functional variants which exhibit a modulatory activity similar to that of the parent protein, and which demonstrate substantial sequence homology to the parent protein. Specifically, variants of NR3-1 will share greater than 98.5% amino acid identity with the NR3-1 protein. Variants of the NR3-1 protein include both naturally occurring variants, an example of which is the NR3-2 protein, illustrated in part in FIG. 3 by nucleic acid and amino acid sequence (SEQ ID NOs: 5 & 6), as well as synthetically derived variants of the human NR3-1 protein.

The term "fragment" is used herein to denote functional segments of an NR3 or NR4 protein.

Variants and fragments of the NR3 and NR4 proteins are said to be "functional" if, on coexpression with an NMDA receptor in a heteromeric receptor complex as defined above, the complex, when assayed electrophysiologically, exhibits ligand-induced ion channel activity having measurable current, i.e. current which is greater than the current in the absence of the ligand or greater than the "baseline" current, and the channel activity possess properties which are characteristic of an NMDA ion channel, for example the channel activity is blocked by $Mg^{++}$ ions and by MK-801.

Each of the naturally occurring members of the human NR3 and NR4 modulatory proteins possess structural features similar to those of EAA receptors, including an extracellular amino-terminal (N-terminal) region, as well as internal hydrophobic domains which serve to anchor the protein within the cell surface membrane. The particular human EAA receptor modulatory protein designated NR3-1 is a protein characterized structurally as a single polypeptide chain that is produced initially in precursor form bearing an N-terminal signal peptide, and is transported to the cell surface in mature form, lacking the signal peptide. The NR3-1 protein, including its signal peptide, consists of 1,484 amino acids arranged in the sequence illustrated, by single letter code, in FIG. 1 (SEQ ID NO: 2). The particular human EAA receptor modulatory protein designated NR4-1 is a protein encoded by the partial nucleotide sequence illustrated in FIG. 4 (SEQ ID NO: 7).

A naturally occurring structurally-related variant of the NR3-1 protein has also been identified and is designated herein, the NR3-2 modulatory protein. This variant protein differs from its NR3-1 parent by a single amino acid as illustrated in FIG. 3. Specifically, the serine residue at position 407 in NR3-1 is an asparagine residue in the NR3-2 variant. This change is reflected as a single nucleotide difference between the nucleic acid encoding the two proteins, namely a codon change from "AGC" in NR3-1 to "AAC" in NR3-2.

The NR3 and NR4 proteins are characterized by their modulatory activity particularly with respect to human NMDA-type receptors, and more particularly with respect to NMDA receptors of the NMDAR1 family, which are described in detail in co-pending U.S. patent application. Ser. No. 07/987,953, the content of which is incorporated herein by reference. The NMDAR1 family of EAA receptors comprises the NMDAR1-1 receptor, the nucleic acid sequence of which is illustrated in FIG. 6 (SEQ ID NO: 10), and variants of the NMDAR1-1 receptor which retain an NMDA-type ligand binding profile and which are structurally related to NMDAR1-1, i.e. share at least 99.6% amino acid identity with the 1-845 amino acid region of the NMDAR1-1 receptor, and preferably share 100% amino acid identity in this region. There are both naturally occurring and synthetically derived variants of the human NMDAR1-1 receptor. Naturally occurring variants include, but are not restricted to, receptor variants designated human NMDAR1-2, NMDAR1-3A and NMDAR1-3C, the partial nucleotide sequences of which are illustrated in FIG. 7 (SEQ ID NOs: 13, 14 & 15, respectively) and compared to the nucleotide sequence of NMDAR1-1 (SEQ ID NO: 12). Another variant, designated NMDAR1-3B, differs in amino acid sequence from the NMDAR1-1 and NMDAR1-3C receptors by a single amino acid at position 470. This amino acid is lysine in NMDAR1-3B and is glutamic acid in NMDAR1-1 and NMDAR1-3C. This change results from a single base pair change in the codon at position 2560 of NMDAR1-1 and NMDAR1-3C from GAG to AAC in the SR variant. An NMDAR1-4 variant differs from the NMDAR1-1 receptor by a peptide insert between amino acids 845 and 846 of NMDAR1-1 as illustrated in FIG. 8. Further variants include NMDAR1-4, NMDAR1-5, NMDAR1-6, NMDAR1-7 and NMDAR1-8, which correspond respectively to the NMDAR1-1, NMDAR1-2, NMDAR1-3 and NMDAR1-4 receptors additionally including a 21 amino acid insert as illustrated in FIG. 9.

One of skill in the art will appreciate that variants of any one of the NMDAR1-1 to NMDAR1-8 receptors which include minor variations from the amino acid sequences thereof, e.g. 1 to 6 amino acid substitutions, deletions or additions, and resulting in receptors retaining the ligand binding profile characteristic of NMDA-type receptors, are also encompassed within the NMDAR1 family of receptors.

Accordingly, the NR3 and NR4 proteins of the present invention are useful in a heteromeric structure to screen for candidate compounds having the ability to alter the activity of the heteromeric receptor complex. In addition, and despite the understanding that the NR3 and NR4 proteins require a heteromeric structure to function in a modulatory sense, cells producing NR3 and NR4 proteins homomerically, independent of association with an NMDA receptor, can be exploited for the purpose of screening candidate ligands for the ability to interact specifically therewith. Those compounds found to interact with an NR3 or an NR4 protein represent potential drug compounds which may have agonist or antagonist properties useful in the treatment of neurological disease conditions.

For use in assessing interaction between an NR3 or an NR4 protein, either in homomeric or heteromeric form, and a candidate compound, it is desirable to construct by application of genetic engineering techniques a cell that produces a human NR3 or NR4 protein in functional form as a heterologous product. The construction of such cell lines is achieved by introducing into a selected host cell a recombinant DNA construct in which DNA coding for a secretable form of the modulatory protein, i.e. a form bearing either its native signal peptide or a functional, heterologous equivalent thereof, is associated with expression controlling elements that are functional in the selected host to drive expression of the modulatory protein-encoding DNA, and thus elaborate the desired NR3 or NR4 protein. Such cells are herein characterized as having the protein-encoding DNA incorporated "expressibly" therein. The protein-encoding DNA is referred to as "heterologous" with respect to the particular cellular host if such DNA is not naturally found in the particular host.

It is most desirable to use a mammalian cell host to produce the present modulatory proteins due to their human origin; however, other suitably engineered eukaryotic and prokaryotic hosts may also be employed to produce NR3 proteins. Accordingly, bacterial hosts such as *E. coli* and *B. subtilis*, fungal hosts such as Assergillus and yeast and insect cell hosts such as *Spodoptera frugiperda*, are examples of non-mammalian hosts that may also be used to produce NR3/NR4 proteins of the present invention.

The particular cell type selected to serve as host for production of the human modulatory proteins can be any of several cell types currently available in the art. Preferably, where the modulatory protein will be expressed in heteromeric form, i.e. in conjunction with an NMDA receptor, the cell type selected will not be one which in its natural state elaborates a surface receptor that has ion channel activity or that elaborates a protein that is capable of modulating receptor activity, so as to confuse the assay results sought from the engineered cell line. Generally, such problems are avoided by selecting as host a non-neuronal cell type. However, neuronal cells may nevertheless serve as expression hosts, provided that any "background" activity is accounted for in the assay results.

According to one embodiment of the present invention, the cell line selected to serve as host for modulatory protein production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available. Any one of these systems can be exploited to drive expression of DNA encoding NR3 or NR4 proteins. These systems, available typically in the form of plasmidic vectors, incorporate expression cassettes, the functional components of which include DNA constituting host-recognizable expression controlling sequences which enable expression of the receptor-encoding DNA when linked 5' thereof. The systems further incorporate DNA sequences which terminate expression when linked 3' of the protein-encoding region. Thus, for expression in a selected mammalian cell host, there is generated a recombinant DNA expression construct in which DNA encoding an NR3 or NR4 protein is linked with expression controlling DNA sequences recognized by the host, including a region 5' of the DNA to drive expression, and a 3' region to terminate expression. The plasmidic vector harbouring the expression construct typically incorporates such other functional components as an origin of replication, usually virally-derived, to permit replication of the plasmid in the expression host, including bacterial hosts such as E. coli. To provide a marker enabling selection of stably transfected recombinant cells, the vector will also incorporate a gene conferring some survival advantage on the transfectants, such as a gene coding for neomycin resistance in which case the transfectants are plated in medium with neomycin.

Included among the various recombinant DNA expression systems that can be used to achieve mammalian cell expression of DNA encoding NR3 or NR4 are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the long terminal repeat (LTR) of retroviruses, insect cell promoters such as those regulated by temperature, and isolated from Drosophila, as well as mammalian gene promoters such as steroid-inducible promoters and those regulated by heavy metals i.e. the metalothionein gene promoter. In order to achieve expression in bacterial hosts, such as E. coli, expression systems that exploit the expression controlling regions of various E. coli and viral genes can be used to drive NR3/NR4 production including the lac gene, the trp gene, and regions of the lambda genome (PL and PR). Expression in yeast can be achieved using the expression-controlling regions of genes such as alcohol dehydrogenase and melibiase, and in Aspergillus, the expression-controlling regions of genes such as alcohol dehydrogenase and glucoamylase may be used. The expression controlling-regions of baculovirus may be used in the case of insect host cells.

For incorporation into the recombinant DNA expression vector, DNA coding for the desired modulatory protein, e.g. an NR3 or NR4 protein, can be obtained by applying selected techniques of gene isolation or gene synthesis. As described in more detail in the examples herein, the present modulatory proteins, including naturally occurring variants thereof, are encoded within the human genome, expressed in human brain tissue, and can therefore be obtained by careful application of conventional gene isolation and cloning techniques. This typically will entail extraction of total messenger RNA from a fresh source of human brain tissue, such as cerebellum, hippocampus or fetal brain tissue, followed by conversion of messenger RNA to cDNA and formation of a library in, for example, a bacterial plasmid, or more typically a bacteriophage. Bacteriophage harbouring fragments of the human DNA are typically grown by plating on a lawn of susceptible E. coli bacteria, such that individual phage plaques or colonies can be isolated. The DNA carried by the phase colony is then typically immobilized on a nitrocellulose or nylon-based hybridization membrane, and then hybridized, under carefully controlled conditions, to a radioactively (or otherwise) labelled nucleotide probe of appropriate sequence to identify the particular phage colony carrying NR3 or NR4-encoding DNA of interest. Typically, the gene or a portion thereof so identified is subcloned into a plasmidic vector for nucleic acid sequence analysis.

Having herein provided the nucleotide sequence of human NR3 modulatory proteins, it will be appreciated that automated techniques of gene synthesis and/or amplification can also be performed to generate DNA coding therefor. Because of the length of NR3-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly using polymerase chain reaction (PCR) technology as generally described by Barnett et al. in Nucl. Acids Res. 18:3094, 1990.

The application of automated gene synthesis techniques provides an opportunity to generate sequence variants of naturally occurring members of the NR3 gene family. It will be appreciated, due to the degeneracy associated with nucleotide triplet codons, that variant polynucleotides coding for the NR3 receptors herein described can be generated by substituting synonymous codons for those represented in the naturally occurring polynucleotide sequences herein identified, such as those identified in FIG. 1 and FIG. 3. For example, as would be known by one of skill in the art, arginine may be encoded by any one of six codons selected from CGA, CGC, CGG, CGU, AGA and AGG, threonine may be encoded by any one of four codons selected from ACA, ACC, ACG and ACU, while lysine is encoded by two codons, AAA and AAG. In addition, polynucleotides coding for synthetic variants of the NR3 receptors can be generated which, for example, incorporate one or more, e.g. 1–10, single amino acid substitutions, deletions or additions. Since it will for the most part be desirable to retain the modulatory activity of the NRS protein for screening purposes, it is desirable to limit amino acid substitutions to those regions which are less critical for modulatory activity as may be elucidated upon domain mapping of the protein. Such substitutions may include, for example, conservative amino acid substitutions such as isoleucine to leucine, or lysine to arginine.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation Of blunt-ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the DNA encoding the desired modulatory protein is incorporated for expression into any suitable expression vector using conventional procedures, and host cells are transfected therewith also using conventional procedures which include, for example, DNA-mediated transformation, electroporation, microinjection, or particle gun transformation. Expression vectors may be selected to provide transfected mammalian cell lines that express the modulatory protein-encoding DNA either transiently or in a stable manner. For transient expression, host cells are typically transfected with an expression vector harbouring an origin of replication functional in a mammalian cell. For stable expression, such replication origins are unnecessary, but the vectors will typically harbour a gene coding for a product that confers on the transfectants a survival advantage, to enable their selection. Genes coding for such selectable markers include, but are not limited to, the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR(−) cells into DHFR(+) cells, and the tk gene of herpes simplex virus, which makes TK(−) cells phenotypically TK(+) cells. Both transient expression and stable expression can provide transfected cell lines, and membrane preparations derived therefrom, for use in screening assays.

The recombinant techniques described above can be equally applied to EAA receptor production, in particular NMDA receptor production, as set out in the specific examples described herein and using, for example, the DNA sequences provided in FIGS. 6 and 7, in the preparation of cells which heteromerically produce a modulatory protein and an NMDA receptor. In this case, once the appropriate modulatory protein-encoding and NMDA receptor-encoding expression vectors have been prepared, the cells selected for expression are transfected with a mixture of the expression vectors in the conventional manner.

For use in screening assays, cells transiently expressing the NR3/NR4-encoding DNA, and the NMDA receptor-encoding DNA, can be stored frozen for later use, but because the rapid rate of plasmid replication will lead ultimately to cell death, usually in a few days, the transfected cells should be used as soon as possible. Such assays may be performed either with intact cells, or with membrane preparations derived from such cells. The membrane preparations typically provide a more convenient substrate for the ligand screening experiments, and are therefore preferred as substrates. To prepare membrane preparations for screening purposes, i.e. ligand binding experiments, frozen intact cells are homogenized while in cold water suspension and a membrane pellet is collected after centrifugation. The pellet is re-suspended and re-centrifuged to remove endogenous ligands that would otherwise compete for binding in the assays. The membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human modulatory protein of the invention, or a heteromeric receptor complex comprising a modulatory protein and an NMDA receptor, is evaluated typically using a predetermined amount of cell-derived membrane (measured for example by protein determination), generally from about 25 ug to 100 ug. Competitive binding assays will be useful to evaluate the affinity of a candidate ligand for a heteromeric complex relative to glutamate. This competitive binding assay can be performed by incubating a membrane preparation with radiolabelled glutamate, for example [$^3$H]-glutamate, in the presence of unlabelled candidate ligand added at varying concentrations. Following incubation, either displaced or bound radiolabelled glutamate can be recovered and measured to determine the relative binding affinities of the candidate ligand and glutamate for the particular receptor used as substrate. In this way, the affinities of various compounds for the heteromeric complex can be measured. As will be appreciated by one of skill in the art, binding assays such as radioimmunoassays and ELISA can also be used to determine binding affinity of a candidate ligand. Such competitive binding assays cannot be used in the case of an NR3 or NR4 protein which is expressed homomerically, in a state that does not naturally bind those ligands bound by EAA receptors. Thus, the binding affinity of candidate ligands for the NR3 or NR4 proteins can be determined using a conventional non-competitive type binding assay. Those ligands determined to have an appropriate affinity for the homomeric modulatory protein, i.e. a binding affinity in the micromolar range, and more preferably in the nanomolar range, can then be selected to determine if their binding is specific, and further, if their binding affects the pharmacological and functional characteristics of a heteromeric modulatory protein/receptor complex.

The NR3 and NR4 proteins of the present invention are functional in a modulatory context, forming heteromeric receptor complexes, comprising a human modulatory protein and an EAA receptor, which exhibit electrophysiological properties that are distinct from those exhibited by either of the modulatory protein or the NMDA receptor components of the complex alone. The modulatory proteins are therefore useful, in the established manner, for screening candidate ligands for their ability to modulate the ion channel activity of such receptor heteromeric complexes. The present invention thus further provides, as a ligand screening technique, a method of detecting interaction between a candidate ligand and a human modultory protein/receptor heteromeric complex, comprising the steps of incubating the candidate ligand with a cell that produces a human modulatory protein/receptor heteromeric complex, or with a membrane preparation derived therefrom, and then measuring the ligand-induced electrical current across said cell or membrane.

As an alternative to using cells that express the modulatory protein, either homomerically or as a heteromeric receptor complex, ligand characterization may also be performed using cells (for example Xenopus oocytes), that yield functional membrane-bound protein following introduction of messenger RNA coding for the NR3 or NR4 protein, in the case of homomeric expression, or coding for a heteromeric complex, in the case of heteromeric expression. Thus, NR3 or NR4 DNA is typically subcloned into a plasmidic vector such that the introduced DNA may be easily transcribed into RNA via an adjacent RNA transcription promoter supplied by the plasmidic vector, for example the T3 or T7 bacteriophage promoters. RNA is then transcribed from the inserted gene In vitro, and isolated and purified therefrom for injection into Xenopus oocytes. In the case of a heteromeric complex, the RNA of the NMDA receptor forming the complex is prepared in the same manner for injection into Xenopus oocytes simultaneously with RNA encoding the modulatory protein. Following the injection of nanoliter volumes of an RNA solution, the oocytes are left to incubate for up to several days, and are then tested for the ability to respond to a particular ligand molecule supplied in a bathing solution. In the heteromeric case, due to the fact that an active membrane channel is formed through which ions may selectively pass, the response of a particular ligand molecule in the bathing solution may typically be measured as an electrical current utilizing microelectrodes inserted into the cell or placed on either side of a cell-derived membrane preparation using the "patch-clamp" technique.

In addition to using DNA encoding the modulatory protein to construct cell lines useful for ligand screening, expression of the DNA can, according to another aspect of the invention, be performed to produce fragments of the protein in soluble form, for structure investigation, to raise antibodies and for other experimental uses. It is therefore desirable in the first instance to facilitate the characterization of particular regions of NR3 or NR4 in quantity and in isolated form, i.e. free from the remainder of the full-length protein. One region of particular interest with regard to the modulatory function of the NR3 and NR4 proteins is the extracellular N-terminal region. To prepare a fragment of the N-terminal region, full-length DNA encoding the modulatory protein may be modified by site-directed mutagenesis, to introduce a translational stop codon into the extracellular N-terminal region, immediately 5' of the first transmembrane domain (TM1). Since there will no longer be produced any transmembrane domain(s) to "anchor" the protein into the membrane, expression of the modified cDNA will result in the secretion, in soluble form, of only the extracellular N-terminal domain. Standard ligandbinding assays may then be performed to ascertain the degree of binding of a candidate compound to the extracellular domain so produced. Alternatively, a translational stop codon may be introduced downstream of the first transmembrane domain to yield a fragment which retains the ability to anchor into the cell membrane. In this way, a heteromeric channel comprising the N-terminal NR3/NR4 fragment can be formed and used to determine the extent of modulatory activity possessed by the fragment. It may of course be necessary, using site-directed mutagenesis, to produce different versions of this extracellular region, or indeed any other extracellular region of the protein, in order to map the modulatory domain with precision.

Alternatively, it may be desirable to produce other regions of the modulatory protein, for example all or part of the carboxy-terminus thereof. In this case, site-directed mutagenesis and/or PCR-based amplification techniques may readily be used to provide a defined fragment of the cDNA encoding the domain of interest. Once obtained, such DNA fragments can be expressed in the usual manner, either homomerically to determine if the fragment has ligand-binding activity, or heteromerically to determine the extent to which the fragment retains modulatory activity. Conventional peptide synthetic techniques may also be used to make the desired C-terminal fragments or other fragments, e.g. a desired N-terminal fragment as noted above.

It will be appreciated that the production of such fragments may be accomplished in a variety of host cells. Mammalian cells such as CHO cells may be used for this purpose, the expression typically being driven by an expression promoter capable of high-level expression, for example, the CMV promoter. Alternately, non-mammalian cells, such as insect Sf9 (*Spodoltera frugiperda*) cells may be used, with the expression typically being driven by expression promoters of the baculovirus, for example the strong, late polyhedrin protein promoter. Filamentous fungal expression systems may also be used to secrete large quantities of selected domains of the modulatory protein. *Aspergillus nidulans* for example, with the expression being driven by the alcA promoter, would constitute such an acceptable fungal expression system. In addition to such expression hosts, it will be further appreciated that any prokaryotic or other eukaryotic expression system capable of expressing heterologous genes or gene fragments, whether intracellularly or extracellularly, would be similarly acceptable.

For use particularly in detecting the presence and/or location of an NR3 or NR4 protein, for example in brain tissue, the present invention also provides, in another of its aspects, antibodies to these proteins. Such antibodies will also have use as diagnostic agents, e.g. to determine if localized amounts or different forms of NR3 or NR4 in selected tissue types are indicative of a disease condition, and as therapeutic agents, by regulating the modulatory activity of an NR3 or NR4 protein on an NMDA receptor ion channel, to prevent disease conditions associated with overactive NMDA receptor ion channels. Preferably, for use therapeutically, the NR3 and NR4 antibodies employed are monoclonal antibodies.

To raise NR3 antibodies, for example, there may be used as immunogen either the intact, soluble NR3 protein or an immunogenic fragment thereof, produced in a microbial or mammalian cell host as described above or by standard peptide synthesis techniques. Regions of the NR3 protein particularly suitable for use as immunogenic fragments include those corresponding in sequence to an extracellular region of the receptor, or a portion of the extracellular region, such as peptides consisting of residues 27–557, or fragments thereof.

The raising of antibodies to the desired NR3 or NR4 protein or immunogenic fragment can be achieved, for polyclonal antibody production, using immunization protocols of conventional design, and any of a variety of mammalian hosts, such as sheep, goats and rabbits. For monoclonal antibody production, immunocytes such as splenocytes can be recovered from the immunized animal and fused, using hybridoma technology, to myeloma cells. The fusion cell products, i.e. hybridoma cells, are then screened by culturing in a selection medium, and cells producing the desired antibody are recovered for continuous growth, and antibody recovery. Recovered antibody can then be coupled covalently to a reporter molecule, i.e. a detectable label, such as a radiolabel, enzyme label, luminescent label or the like, optionally using linker technology established for this purpose.

In detectably labelled form, e.g. radiolabelled form, olignucleotides, including both DNA or RNA, coding for the human NR3 or NR4 modulatory protein and selected regions thereof, may also be used, in accordance with another aspect of the present invention, as hybridization probes for example to identify sequence-related genes resident in the human or other mammalian genomes (or cDNA libraries) or to locate DNA encoding an NR3 or NR4 protein in a specimen, such as brain tissue. This can be done using either the intact coding region, or a fragment thereof, having radiolabelled nucleotides, for example, $^{32}$P-labelled nucleotides, incorporated therein. To identify the NR3-encoding DNA in a specimen, it is desirable to use either the full length cDNA coding therefor, or a fragment which is unique thereto. With reference to FIG. 1 and the nucleotide numbering appearing thereon, such nucleotide fragments include those comprising at least about 17 nucleic acids which correspond in sequence to an extracellular region of NR3 DNA, e.g. the N-terminus thereof. Examples of suitable nucleotide fragments are the regions spanning nucleotides 8–1888 and 2732–5976 of NR3-1. Such sequences, and the intact gene itself, may also be used of course to clone NR3-related human genes, particularly cDNA equivalents thereof, by standard hybridization techniques.

Embodiments of the present invention are described in detail in the following specific Examples which should not be construed as limiting.

EXAMPLE 1

Isolation of DNA Coding for Human NR3-1

A human NR2A DNA probe corresponding to a portion of nucleotide sequence of NR2A-1, namely the nucleotide regions 1832–2361 (SEQ ID NO:9) as shown in FIG. 5, was generated by PCR-based amplification of recombinant bacteriophage lambda DNA isolated from an Eco RI-based bacteriophage lambda library of human hippocampus cDNA (obtained from Stratagene Cloning Systems, La Jolla, Calif.). The following degenerate oligonucleotide primers were used in the PCR amplification:

1) 5' GGGGTTTAGATCTGGGT-A/C/G/T-ATGATGTT-C/T-GT-A/C/G/T-ATG 3' (SEQ ID NO:20); and
2) 5' GGGGIIIAGATCTGC-A/C/G/T-GC-A/G-TC-A/G-TA-A/G/T-AT-A/G-AA-A/G/CIT-GC 3' (SEQ ID NO:21)

The primers were used at a final concentration of 2 pmol/µl each, in a 50 µl reaction volume (10 mM Tris-HCl, pH 9.0; 50 mM KCl; 1.5 mM MgCl$_2$) containing 100 ng of recombinant human hippocampus cDNA/bacteriophage lambda DNA, 5 units of *Thermus aauaticus* DNA polymerase (Promega, Madison, Wis.) and 0.2 mM of each deoxyribonucleotide. Thirty-five cycles of amplification proceeded, with denaturation at 95° C. for 1 min., annealing at 50° C. for 1 min., and primer extension at 72° C. for 1 min., followed by a final cycle at 72° C. for 5 min. The 554 bp PCR product was purified from an agarose gel and subcloned into the plasmid vector pT7Blue-T (Novagen, Madison, Wis.) for DNA sequencing.

A human NR4 DNA probe corresponding to a portion of nucleotide sequence of NR4, namely the nucleotide regions 679–1263 as shown in FIG. 4, was also generated as described above.

The 554 bp human NR2A and NR4 probes were radiolabelled with [α-$^{32}$P]dCTP using the Amersham Megaprime DNA labelling system (Arlington Heights, Ill.) to a specific activity of 1.0×10$^9$ cpm/µg. The labelled probes were used to screen approximately 1×10$^6$ plaques of the EcoRI-based human hippocampus cDNA/bacteriophage lambda Zap II library identified above and approximately 800,000 plaques of an Eco RI-based human fetal brain cDNA/bacteriophage lambda Zap II library (obtained from Stratagene). Fifteen positive plaques were identified on replica filters under the following hybridization conditions: 6×SSPE, 50% formamide, 0.5% SDS, 100 µg/ml denatured salmon sperm DNA at 42° C. with 1.85×10$^6$ cpm probe per ml hybridization fluid. The filters were washed twice with 2×SSPE, 050% SDS at 25° C. for 5 min., followed by a 15 min. wash at 42° C. The filters were exposed to X-ray film (Kodak, Rochester, N.Y.) overnight. The plaques were purified and excised as phagemids according to the supplier's specifications, to generate an insert-carrying Bluescript-SK variant of the phagemid vector.

DNA sequence analysis of the largest NR3 overlapping clones (isolated as pBS/FB2C and pBS/FB18) revealed a putative ATG initiation codon together with about 210 nucleotides of 5' untranslated (UTR) information and 4,452 nucleotides of amino acid coding information. This analysis also revealed a termination codon as well as 1,307 nucleotides of 3' untranslated information. The entire DNA sequence of the NR3-1 cDNA is provided in FIG. 1.

Partial DNA sequence analysis of the largest NR4 overlapping clones (isolated as pBS/H5A and pBS/H34A) indicated 1,785 nucleotides of amino acid coding information. The DNA sequence of the partial NR4-1 cDNA is provided in FIG. 4.

EXAMPLE 2

Isolation of DNA Coding for the Human NMDAR1-1 Receptor

A human NMDAR1 probe corresponding to a portion of nucleotide sequence of NMDAR1-1, namely the nucleotide regions 2605–3213 as shown in FIG. 6, was generated by PCR-based amplification of recombinant bacteriophage lambda DNA isolated from an Eco RI-based bacteriophage lambda library of human hippocampus cDNA (obtained from Stratagene Cloning Systems, La Jolla, Calif.). The following degenerate oligonucleotide primers were used in the PCR amplification:

1) 5' GGGGTTTGGATCCAA-A/G-GA-A/G-TGGAA-C/T-GGNATGATG 3' (SEQ ID NO:22); and
2) 5' GGGGTTTAAGCTT-C/T-TC-G/A-TA-G/A-TT-G/A-TG-C/T-TT-C/T-TCCAT 3' (SEQ ID NO:23)

The primers were used at a final concentration of 5 pmol/µl each, in a 50 µl reaction volume (10 mM Tris-HCl, pH 9.0; 50 mM KCl; 1.5 mM MgCl$_2$) containing 100 ng of recombinant human hippocampus cDNA/bacteriophage lambda DNA, 5 units of *Thermus aquaticus* DNA polymerase (Promega, Madison, Wis.) and 0.2 mM of each deoxyribonucleotide. Thirty-five cycles of amplification proceeded, with denaturation at 94° C. for 1 min., annealing at 51° C. for 1 min., and primer extension at 72° C. for 1 min., followed by a final cycle at 72° C. for 5 min. The 674 bp PCR product was purified from an agarose gel and subcloned into the plasmid vector pTZBlue-T (Novagen, Madison, Wis.) for DNA sequencing.

The 674 bp human NMDAR1 probe was radiolabelled with [α-$^{32}$P]dCTP using the Amersham Megaprime DNA labelling system (Arlington Heights, Ill.) to a specific activity of 1.0–2.4×10$^9$ cpm/ug. The labelled probe was used to screen approximately 400,000 plaques of an Eco RI-based human hippocampus cDNA/bacteriophage lambda Zap II library. Thirty-five positive plaques were identified on replica filters under the following hybridiztion conditions: 6×SSC, 50% formamide, 0.5% SDS, 100 ug/ml denatured salmon sperm DNA at 42° C. with 1.85×10$^6$ cpm probe per ml hybridization fluid. The filters were washed with 2×SSC, 0.5% SDS at 25° C. for 5 min., followed by 15 min. washes at 37° C. and at 42° C. The filters were exposed to X-ray film (Kodak, Rochester, NY) overnight. Twenty-eight plaques were purified and excised as phagemids according to the supplier's specifications, to generate an insert-carrying Bluescript-SK variant of the phagemid vector.

DNA sequence analysis of the clone NMDAR1-3C revealed 2,814 nucleotides of amino acid coding information (938 amino acids). The entire DNA sequence of the EcoRI-EcoRI NMDAR1-3C cDNA insert is provided herein by reference to the sequence of NMDAR1-1 set out in FIG. 6 and by reference to the sequence differences between NMDAR1-1 and NMDAR1-3C outlined in FIG. 7. The NMDAR1-3C cDNA was subcloned into the pcDNA1-Amp mammalian expression vector (to form pcDNA1-Amp/hNR1-3C) using standard techniques such as those described below in Example 3 for the subcloning of the NR2A clone into the pcDNA1-Amp vector.

It will be appreciated that the protocol described above can be used to isolate any of the NMDAR1 receptors in accordance with the present invention.

EXAMPLE 3

Construction of Genetically Engineered Cells Producing a Heteromeric Complex of Human NR3-1 and NMDAR1-3C For transient expression in mammalian cells, cDNA coding for human NR3-1 was incorporated into the mammalian expression vector pcDNA1-Amp (Invitrogen Corporation, San Diego, Calif.). This is a multifunctional 5 kbp plasmid vector designed for cDNA expression in eukaryotic systems, and cDNA analysis in prokaryotes. Incorporated on the vector are the CMV immediate early gene promoter and enhancer sequences, SV40 transcription termination and RNA processing signals, SV40 and polyoma virus origins of replication, M13 and ColE1 origins, Sp6 and T7 RNA promoters, and a gene conferring ampicillin resistance. A polylinker is located appropriately downstream of the CMV and T7 promoters.

The strategy depicted in FIG. 2 was employed to facilitate incorporation of the NR3-1 cDNA into the expression vector. The FB2C 5' 5.3 kbp BamHI/SphI fragment was released from pBS/FB2C and ligated with the 2.5 kbp BamHI/SphI fragment of pBS/FB18(#20). Restriction-endonuclease digestion was performed to confirm proper insert orientation. The resulting plasmid was termed pBS/hNR3. The 4.8 kbp EcoRI/NotI fragment of pBS/hNR3 was incorporated at the EcoRI/NotI site in the pcDNA1-Amp polylinker. Restriction-endonuclease digestion and DNA sequence analysis was performed to confirm proper insert orientation. The resulting plasmid, designated pcDNA1-Amp/hNR3, was then introduced for transient expression into a selected mammalian cell host, in this case human embryonic kidney cells of the HEK293 lineage (available from the American Type Culture Collection, Rockville, Md.; ATCC CRL 1573).

The 7.8 kbp plasmid designated pBS/hNR3 carrying the NR3-1 DNA as a 4.8 kbp insert in a 3 kbp pBS plasmid background, was deposited, under the terms of the Budapest Treaty, with the American Type Culture Collection in Rockville, Md., USA on Jun. 3, 1994 under accession number ATCC 75799.

For transient expression, HEK293 cells were transfected with approximately 0.4 μg DNA (as pcDNA1-Amp/hNR3 or pcDNA1-Amp/hNR1-3C) per 10$^5$ HEK293 cells, by lipofectamine-mediated DNA transfection according to the manufacturer's (Life Technologies Inc., Gaithersburg, Md.) specifications. In coexpression experiments, i.e. for heteromeric expression of NR3-1 and NMDAR1-3C, the HEK293 cells were similarly transfected with 0.8 μg of a DNA mixture containing pcDNA1-Amp/hNR3 and pcDNA1-Amp/hNR1-3C. Briefly, HEK293 cells were plated at a density of 10$^5$ cells/dish and then grown for 24 hours in 10% FBS-supplemented MEM medium (Life Technologies Inc., Gaithersburg, Md.). The medium was then removed and cells were washed in OPTI-MEM I medium (Life Technologies Inc.) lacking FBS, prior to transfection. A transfection solution (100 μl) containing 2–4 μl of lipofectamine and DNA was then applied to the cells. After incubation for 4 hours at 37° C., cells were washed as previously described and then allowed to grow for 48 hours in 10% FBS-supplemented MEM medium containing 50 μM DL-AP5 (2-amino-5-phosphonopentanoic acid) and 50 μM 7-chlorokyneurinic acid prior to electrophysiological recording.

In a like manner, stably transfected cell lines can also be prepared using various cell types as host: HEK293, CHO K1 or CHO Pro5. To construct these cell lines, cDNA coding for NR3-1 is incorporated into the mammalian expression vector pRc/CMV (Invitrogen Corp., San Diego, Calif.) which enables stable expression. Insertion of the cDNA places it under the expression control of the CMV promoter and upstream of the polyadenylation site and terminator of the bovine growth hormone gene, and into a vector background comprising the neomycin resistance gene (driven by the SV40 early promoter) as selectable marker. To introduce plasmids constructed as described above, the host cells are first seeded at a density of 5×10$^5$ cells/dish in 10% FBS-supplemented MEM medium. After growth for 24 hours, fresh medium is added to the plates and three hours later, the cells are transfected using the lipofectin-mediated DNA transfection procedure according to the manufacturers specifications. Cells resistant to neomycin are selected in 10% FBS-supplemented MEM medium containing G418 (1 mg/ml). Individual colonies of G418-resistant cells are isolated about 2–3 weeks later, clonally selected and then propagated for assay purposes.

EXAMPLE 4

Electrophysiological Characterization

Standard whole-cell voltage-clamp (Axopatch 1B, Axon Instruments, Foster City, Calif.) techniques were used to record 60 μM NMDA-evoked currents in HEK293 cells transiently transfected as described in Example 3 and expressing hNR3-1 heteromerically with the NMDAR1-3C receptor. The cells were rinsed prior to recording with a solution of 130 mM NaCl, 5.4 mM KCl, 1.8 mM CaCl$_2$, 10 μM glycine, 5 mM HEPES, pH 7.2 (300 mOsm.). Single electrode, voltage-clamp recordings were carried out using thin-walled borosilicate glass electrodes (WPI-TW150-F4, WPI Inc., Sarasota, Fla.) filled with an intracellular solution of 140 mM CsCl, 1 mM MgCl$_2$, 10 mM EGTA, 10 mM HEPES, pH 7.2 (adjusted with 1 M CsOH). NMDA application using a computer controlled array of perfusion barrels allowed for fast application and continuous perfusion with control or 1 mM Mg$^{2+}$-containing solutions (lag<50 milliseconds).

The results of the electrophysiological characterization are depicted in FIG. 10. Points at which NMDA was applied are indicated with black bars above the recordings. No NMDA-induced depolarizations were observed in HEK293 cells transiently transfected with NMDAR1-3C alone, or with NR3 alone. NMDA-induced depolarizations were, however, observed in HEK293 cells transiently transfected with both NR3-1 and NMDAR1-3C. As illustrated, these latter currents were blocked by 1 mM $MgCl_2$, a result which is characteristic of NMDA-gated ion channels.

This electrophysiological characterization indicates that the NR3/NMDA receptor heteromeric complex functions in an authentic manner, and can therefore be used to reliably predict the functional "signature" of its non-recombinant counterpart from intact human brain. These features make the recombinant receptor especially useful for selecting and characterizing ligand compounds which bind to or otherwise modulate the receptor, and/or for selecting and characterizing compounds which may act by displacing other ligands from the receptor. The isolation of the NR3 protein in a pure form, and its expression with an NMDA receptor as a single, homogenous complex, therefore frees the electrophysiological assay from the lack of precision introduced when complex receptor preparations from human and non-human brains are used to attempt such characterizations.

It will be appreciated that the protocol described above can be used to determine the electrophysiological characteristics of other NR3/NMDA heteromeric receptor complexes, such as for example, the NR3-2/NMDAR1-1 complex.

EXAMPLE 5

Ligand-binding Assays on Heteromeric NR3-1/ NMDAR1-3C Complex

Frozen transfected cells, prepared as described in Example 3 above, are resuspended in ice-cold distilled water, sonicated for 5 seconds, and centrifuged for 10 minutes at 50,000×g. The supernatant is discarded and the membrane pellet is stored frozen at −70° C.

Cell membrane pellets are resuspended in ice cold 50 mM Tris-HCl, pH 7.55, and centrifuged again at 50,000×g for 10 minutes in order to remove endogenous glutamate that would otherwise compete for binding. The pellets are resuspended in ice cold 50 mM Tris-HCl, pH 7.55, and used for the binding experiments described below. Protein concentrations are determined using the Pierce reagent with BSA as an internal standard.

Binding assays are performed using a 25–100 µg protein equivalent of the cell membrane preparation, and a selected radiolabeled ligand. In particular, for MK-801-binding assays, incubation mixtures consist of 20 nM (+)-[3-$^3$H] MK-801 (30 Ci/mmole), 20 µM glycine, and 1 mM L-glutamate in cold incubation buffer (50 mM Tris-HCl, pH 7.55) at a final volume of 250 µl. Non-specific binding is determined in the presence of 1 mM (+)MK-801. For glutamate binding assays, incubation mixtures consist of 30 nM [3,4-$^3$H]-L-glutamate (47.3 Ci/mmole) in cold incubation buffer at a final volume of 250 µl. Non-specific binding is determined in the presence of 1 mM L-glutamate and displacement is determined in the presence of 1 mM NMDA, 1 mM kainate, or 1 mM AMPA. The reaction mixtures are incubated on ice for 60 minutes in plastic mini-vials. Bound and free ligand are separated by centrifugation for 30 minutes at 50,000×g. The pellets are washed three times in 4 ml of the cold incubation buffer, and then 4 ml of Beckman Ready-Protein Plus scintillation cocktail was added for liquid scintillation counting.

It will be appreciated that the protocol described above can be used to determine the pharmacological characteristics of other NR3/NMDA heteromeric receptor complexes, such as for example, the NR3-1/NMDAR1-1 complex.

EXAMPLE 6

Ligand-binding Assay for the Homomeric Expression of NR3-1

Frozen transfected cells, prepared as described in Example 3 above and expressing NR3-1 in the absence of an NMDA receptor, are resuspended in ice-cold distilled water, sonicated for 5 seconds, and centrifuged for 10 minutes at 50,000×g. The supernatant is discarded and the membrane pellet is stored frozen at −70° C.

Cell membrane pellets are resuspended in ice cold 50 mM Tris-HCl, pH 7.55, and centrifuged again at 50,000×g for 10 minutes in order to remove endogenous ligands that might otherwise compete for binding. The pellets are resuspended in ice cold 50 mM Tris-HCl, pH 7.55, and used for the binding experiments described below. Protein concentrations are determined using the Pierce reagent with BSA as an internal standard.

Binding assays are performed using a 25–100 µg protein equivalent of the cell membrane preparation, and a selected radiolabeled ligand in cold incubation buffer (50 mM Tris-HCl, pH 7.55) at a final volume of 250 µl. Non-specific binding is determined in the presence of the unlabeled ligand. The reaction mixtures are incubated on ice for 60 minutes in plastic minivials. Bound and free ligand are separated by centrifugation for 30 minutes at 50,000×g. The pellets are washed three times in 4 ml of the cold incubation buffer, and then 4 ml of Beckman Ready-Protein Plus scintillation cocktail are added for liquid scintillation counting.

Having determined that the selected ligand binds specifically to NR3-1, i.e. that unlabelled ligand competes for binding with the labelled form of that ligand, and that the binding is saturable, the ligand is then tested for its ability to affect the heteromeric expression of NR3-1, i.e. when coexpressed with an NMDA receptor as described above. Appropriate experiments for this purpose include the ligand binding experiment described in Example 5, and the electrophysiological characterization described in Example 4.

EXAMPLE 7

Isolation and Cloning of the NR3-2 Variant

The procedures described in Examples 1 and 3 for isolating and cloning the NR3-1 protein are applied equally for the isolation and cloning of NR3-2 and other naturally occuring variants of NR3-1, particularly in view of the high sequence homology between the NR3-1 receptor and the NR3-2 variant.

Moreover, the electrophysiological and ligand-binding assays described in Examples 4, 5 and 6, respectively, are used in the manner described to determine the electrophysiological and ligand binding characteristics of NR3-2 and other NR3-1 variants.

We claim:

1. A method of assaying a candidate ligand for interaction with a human NR3 protein selected from the group consisting of:

NR3-1 having the amino acid sequence of SEQ ID NO:2; and

NR3-2 having the amino acid sequence of SEQ ID NO:2 with the exception that the serine residue at position 407 is an asparagine residue, which comprises the steps of incubating the candidate ligand under appropriate conditions with a cell having incorporated expressibly therein a heterologous polynucleotide encoding said NR3 protein, or with a membrane preparation derived therefrom, and then determining the extent of binding between the human NR3 protein and the candidate ligand.

2. A method of assaying a candidate ligand for interaction with a human heteromeric receptor complex comprising human NR3 protein and human NMDA protein, wherein said NR3 protein is selected from the group consisting of:

NR3-1 having the amino acid sequence of SEQ ID NO:2; and

NR3-2 having the amino acid sequence of SEQ ID NO:2 with the exception that the serine residue at position 407 is an asparagine residue, said method comprising the steps of incubating the candidate ligand under appropriate conditions with a cell that has been engineered genetically to produce said heteromeric receptor complex, said cell having incorporated expressible therein a heterologous polynucleotide encoding said NR3 protein and a heterologous polynucleotide encoding said NMDA protein, or with a membrane preparation derived therefrom, and then determining the extent of binding between the complex and the candidate ligand, or determining ligand-induced electrical current across said cell or membrane.

3. A method as defined in claim 2, wherein said human NMDA protein is selected from the group consisting of:

a) NMDAR1-1 having the amino acid sequence of SEQ ID NO:11;

b) NMDAR1-2 having the amino acid sequence of SEQ ID NO:11 wherein amino acids 841–850 of SEQ ID NO:11 are replaced by the amino acids encoded by SEQ ID NO:13;

c) NMDAR1-3A having the amino acid sequence of SEQ ID NO:11 wherein amino acids 841–850 of SEQ ID NO:11 are replaced by the amino acids encoded by SEQ ID NO:14;

d) NMDAR1-3C having the amino acid sequence of SEQ ID NO:11 wherein amino acids 841–850 of SEQ ID NO:11 are replaced by the amino acids encoded by SEQ ID NO:15;

e) NMDAR1-3B having the amino acid sequence of NMDAR1-3C wherein residue 470 is a lysine residue;

f) NMDAR1-4 having the amino acid sequence of SEQ ID NO:11 wherein the sequence from position 803 is replaced with the amino acid sequence of SEQ ID NO:17;

g) NMDAR1-5 having the amino acid sequence of NMDAR1-1 wherein the amino acids of 160–185 are replaced with the amino acid sequence of SEQ ID NO:18;

h) NMDAR1-6 having the amino acid sequence of NMDAR1-2 wherein the amino acids of 160–185 are replaced with the amino acid sequence of SEQ ID NO:18;

i) NMDAR1-7 having the amino acid sequence of NMDAR1-3 wherein the amino acids of 160–185 are replaced with the amino acid sequence of SEQ ID NO:18; and j) NMDAR1-8 having the amino acid sequence of NMDAR1-4 wherein the amino acids of 160–185 are replaced with the amino acid sequence of SEQ ID NO:18.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 5983 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 218..4669

(xi) SEQUENCE DESCRIPTION: SEQ ID NO:1:

```
GAATTCCTTT GAATTTGCAT CTCTTCAAGA CACAAGATTA AAACAAAATT TACGCTAAAT        60

TGGATTTTAA ATTATCTTCC GTTCATTTAT CCTTCGTCTT TCTTATGTGG ATATGCAAGC       120

GAGAAGAAGG GACTGGACAT TCCCAACATG CTCACTCCCT TAATCTGTCC GTCTAGAGGT       180

TTGGCTTCTA CAAACCAAGG GAGTCGACGA GTTGAAG ATG AAG CCC AGA GCG GAG        235
                                         Met Lys Pro Arg Ala Glu
                                           1               5

TGC TGT TCT CCC AAG TTC TGG TTG GTG TTG GCC GTC CTG GCC GTG TCA        283
Cys Cys Ser Pro Lys Phe Trp Leu Val Leu Ala Val Leu Ala Val Ser
            10                  15                  20

GGC AGC AGA GCT CGT TCT CAG AAG AGC CCC CCC AGC ATT GGC ATT GCT        331
Gly Ser Arg Ala Arg Ser Gln Lys Ser Pro Pro Ser Ile Gly Ile Ala
        25                  30                  35

GTC ATC CTC GTG GGC ACT TCC GAC GAG GTG GCC ATC AAG GAT GCC CAC        379
Val Ile Leu Val Gly Thr Ser Asp Glu Val Ala Ile Lys Asp Ala His
    40                  45                  50

GAG AAA GAT GAT TTC CAC CAT CTC TCC GTG GTA CCC CGG GTG GAA CTG        427
Glu Lys Asp Asp Phe His His Leu Ser Val Val Pro Arg Val Glu Leu
 55                  60                  65                  70

GTA GCC ATG AAT GAG ACC GAC CCA AAG AGC ATC ATC ACC CGC ATC TGT        475
Val Ala Met Asn Glu Thr Asp Pro Lys Ser Ile Ile Thr Arg Ile Cys
                75                  80                  85

GAT CTC ATG TCT GAC CGG AAG ATC CAG GGG GTG GTG TTT GCT GAT GAC        523
Asp Leu Met Ser Asp Arg Lys Ile Gln Gly Val Val Phe Ala Asp Asp
            90                  95                 100

ACA GAC CAG GAA GCC ATC GCC CAG ATC CTC GAT TTC ATT TCA GCA CAG        571
Thr Asp Gln Glu Ala Ile Ala Gln Ile Leu Asp Phe Ile Ser Ala Gln
        105                 110                 115

ACT CTC ACC CCG ATC CTG GGC ATC CAC GGG GGC TCC TCT ATG ATA ATG        619
Thr Leu Thr Pro Ile Leu Gly Ile His Gly Gly Ser Ser Met Ile Met
    120                 125                 130

GCA GAT AAG GAT GAA TCC TCC ATG TTC TTC CAG TTT GGC CCA TCA ATT        667
Ala Asp Lys Asp Glu Ser Ser Met Phe Phe Gln Phe Gly Pro Ser Ile
135                 140                 145                 150

GAA CAG CAA GCT TCC GTA ATG CTC AAC ATC ATG GAA GAA TAT GAC TGG        715
Glu Gln Gln Ala Ser Val Met Leu Asn Ile Met Glu Glu Tyr Asp Trp
                155                 160                 165

TAC ATC TTT TCT ATC GTC ACC ACC TAT TTC CCT GGC TAC CAG GAC TTT        763
Tyr Ile Phe Ser Ile Val Thr Thr Tyr Phe Pro Gly Tyr Gln Asp Phe
            170                 175                 180

GTA AAC AAG ATC CGC AGC ACC ATT GAG AAT AGC TTT GTG GGC TGG GAG        811
Val Asn Lys Ile Arg Ser Thr Ile Glu Asn Ser Phe Val Gly Trp Glu
        185                 190                 195
```

-continued

```
CTA GAG GAG GTC CTC CTA CTG GAC ATG TCC CTG GAC GAT GGA GAT TCT       859
Leu Glu Glu Val Leu Leu Leu Asp Met Ser Leu Asp Asp Gly Asp Ser
    200                 205                 210

AAG ATC CAG AAT CAG CTC AAG AAA CTT CAA AGC CCC ATC ATT CTT CTT       907
Lys Ile Gln Asn Gln Leu Lys Lys Leu Gln Ser Pro Ile Ile Leu Leu
215                 220                 225                 230

TAC TGT ACC AAG GAA GAA GCC ACC TAC ATC TTT GAA GTG GCC AAC TCA       955
Tyr Cys Thr Lys Glu Glu Ala Thr Tyr Ile Phe Glu Val Ala Asn Ser
                235                 240                 245

GTA GGG CTG ACT GGC TAT GGC TAC ACG TGG ATC GTG CCC AGT CTG GTG      1003
Val Gly Leu Thr Gly Tyr Gly Tyr Thr Trp Ile Val Pro Ser Leu Val
            250                 255                 260

GCA GGG GAT ACA GAC ACA GTG CCT GCG GAG TTC CCC ACT GGG CTC ATC      1051
Ala Gly Asp Thr Asp Thr Val Pro Ala Glu Phe Pro Thr Gly Leu Ile
        265                 270                 275

TCT GTA TCA TAT GAT GAA TGG GAC TAT GGC CTC CCC GCC AGA GTG AGA      1099
Ser Val Ser Tyr Asp Glu Trp Asp Tyr Gly Leu Pro Ala Arg Val Arg
    280                 285                 290

GAT GGA ATT GCC ATA ATC ACC ACT GCT GCT TCT GAC ATG CTG TCT GAG      1147
Asp Gly Ile Ala Ile Ile Thr Thr Ala Ala Ser Asp Met Leu Ser Glu
295                 300                 305                 310

CAC AGC TTC ATC CCT GAG CCC AAA AGC AGT TGT TAC AAC ACC CAC GAG      1195
His Ser Phe Ile Pro Glu Pro Lys Ser Ser Cys Tyr Asn Thr His Glu
                315                 320                 325

AAG AGA ATC TAC CAG TCC AAT ATG CTA AAT AGG TAT CTG ATC AAT GTC      1243
Lys Arg Ile Tyr Gln Ser Asn Met Leu Asn Arg Tyr Leu Ile Asn Val
            330                 335                 340

ACT TTT GAG GGG AGG AAT TTG TCC TTC AGT GAA GAT GGC TAC CAG ATG      1291
Thr Phe Glu Gly Arg Asn Leu Ser Phe Ser Glu Asp Gly Tyr Gln Met
        345                 350                 355

CAC CCG AAA CTG GTG ATA ATT CTT CTG AAC AAG GAG AGG AAG TGG GAA      1339
His Pro Lys Leu Val Ile Ile Leu Leu Asn Lys Glu Arg Lys Trp Glu
    360                 365                 370

AGG GTG GGG AAG TGG AAA GAC AAG TCC CTG CAG ATG AAG TAC TAT GTG      1387
Arg Val Gly Lys Trp Lys Asp Lys Ser Leu Gln Met Lys Tyr Tyr Val
375                 380                 385                 390

TGG CCC CGA ATG TGT CCA GAG ACT GAA GAG CAG GAG GAT GAC CAT CTG      1435
Trp Pro Arg Met Cys Pro Glu Thr Glu Glu Gln Glu Asp Asp His Leu
                395                 400                 405

AGC ATT GTG ACC CTG GAG GAG GCA CCA TTT GTC ATT GTG GAA AGT GTG      1483
Ser Ile Val Thr Leu Glu Glu Ala Pro Phe Val Ile Val Glu Ser Val
            410                 415                 420

GAC CCT CTG AGT GGA ACC TGC ATG AGG AAC ACA GTC CCC TGC CAA AAA      1531
Asp Pro Leu Ser Gly Thr Cys Met Arg Asn Thr Val Pro Cys Gln Lys
        425                 430                 435

CGC ATA GTC ACT GAG AAT AAA ACA GAC GAG GAG CCG GGT TAC ATC AAA      1579
Arg Ile Val Thr Glu Asn Lys Thr Asp Glu Glu Pro Gly Tyr Ile Lys
    440                 445                 450

AAA TGC TGC AAG GGG TTC TGT ATT GAC ATC CTT AAG AAA ATT TCT AAA      1627
Lys Cys Cys Lys Gly Phe Cys Ile Asp Ile Leu Lys Lys Ile Ser Lys
455                 460                 465                 470

TCT GTG AAG TTC ACC TAT GAC CTT TAC CTG GTT ACC AAT GGC AAG CAT      1675
Ser Val Lys Phe Thr Tyr Asp Leu Tyr Leu Val Thr Asn Gly Lys His
                475                 480                 485

GGG AAG AAA ATC AAT GGA ACC TGG AAT GGT ATG ATT GGA GAG GTG GTC      1723
Gly Lys Lys Ile Asn Gly Thr Trp Asn Gly Met Ile Gly Glu Val Val
            490                 495                 500

ATG AAG AGG GCC TAC ATG GCA GTG GGC TCA CTC ACC ATC AAT GAG GAA      1771
Met Lys Arg Ala Tyr Met Ala Val Gly Ser Leu Thr Ile Asn Glu Glu
```

-continued

|  |  |  |  |  |
|---|---|---|---|---|
| | 505 | 510 | 515 | |
| CGA TCG GAG GTG GTC GAC TTC TCT GTG CCC TTC ATA GAG ACA GGC ATC<br>Arg Ser Glu Val Val Asp Phe Ser Val Pro Phe Ile Glu Thr Gly Ile<br>520                          525                      530 | 1819 |
| AGT GTC ATG GTG TCA CGC AGC AAT GGG ACT GTC TCA CCT TCT GCC TTC<br>Ser Val Met Val Ser Arg Ser Asn Gly Thr Val Ser Pro Ser Ala Phe<br>535                          540                      545                      550 | 1867 |
| TTA GAG CCA TTC AGC GCT GAC GTA TGG GTG ATG ATG TTT GTG ATG CTG<br>Leu Glu Pro Phe Ser Ala Asp Val Trp Val Met Met Phe Val Met Leu<br>                        555                      560                      565 | 1915 |
| CTC ATC GTC TCA GCC GTG GCT GTC TTT GTC TTT GAG TAC TTC AGC CCT<br>Leu Ile Val Ser Ala Val Ala Val Phe Val Phe Glu Tyr Phe Ser Pro<br>                        570                      575                      580 | 1963 |
| GTG GGT TAT AAC AGG TGC CTC GCT GAT GGC AGA GAG CCT GGT GGA CCC<br>Val Gly Tyr Asn Arg Cys Leu Ala Asp Gly Arg Glu Pro Gly Gly Pro<br>            585                      590                      595 | 2011 |
| TCT TTC ACC ATC GGC AAA GCT ATT TGG TTG CTC TGG GGT CTG GTG TTT<br>Ser Phe Thr Ile Gly Lys Ala Ile Trp Leu Leu Trp Gly Leu Val Phe<br>600                          605                      610 | 2059 |
| AAC AAC TCC GTA CCT GTG CAG AAC CCA AAG GGG ACC ACC TCC AAG ATC<br>Asn Asn Ser Val Pro Val Gln Asn Pro Lys Gly Thr Thr Ser Lys Ile<br>615                        620                      625                      630 | 2107 |
| ATG GTG TCA GTG TGG GCC TTC TTT GCT GTC ATC TTC CTG GCC AGC TAC<br>Met Val Ser Val Trp Ala Phe Phe Ala Val Ile Phe Leu Ala Ser Tyr<br>                        635                      640                      645 | 2155 |
| ACT GCC AAC TTA GCT GCC TTC ATG ATC CAA GAG GAA TAT GTG GAC CAG<br>Thr Ala Asn Leu Ala Ala Phe Met Ile Gln Glu Glu Tyr Val Asp Gln<br>            650                      655                      660 | 2203 |
| GTT TCT GGC CTG AGC GAC AAA AAG TTC CAG AGA CCT AAT GAC TTC TCA<br>Val Ser Gly Leu Ser Asp Lys Lys Phe Gln Arg Pro Asn Asp Phe Ser<br>            665                      670                      675 | 2251 |
| CCC CCT TTC CGC TTT GGG ACC GTG CCC AAC GGC AGC ACA GAG AGA AAT<br>Pro Pro Phe Arg Phe Gly Thr Val Pro Asn Gly Ser Thr Glu Arg Asn<br>680                          685                      690 | 2299 |
| ATT CGC AAT AAC TAT GCA GAA ATG CAT GCC TAC ATG GGA AAG TTC AAC<br>Ile Arg Asn Asn Tyr Ala Glu Met His Ala Tyr Met Gly Lys Phe Asn<br>695                        700                      705                      710 | 2347 |
| CAG AGG GGT GTA GAT GAT GCA TTG CTC TCC CTG AAA ACA GGG AAA CTG<br>Gln Arg Gly Val Asp Asp Ala Leu Leu Ser Leu Lys Thr Gly Lys Leu<br>                715                      720                      725 | 2395 |
| GAT GCC TTC ATC TAT GAT GCA GCA GTG CTG AAC TAT ATG GCA GGC AGA<br>Asp Ala Phe Ile Tyr Asp Ala Ala Val Leu Asn Tyr Met Ala Gly Arg<br>                730                      735                      740 | 2443 |
| GAT GAA GGC TGC AAG CTG GTG ACC ATT GGC AGT GGG AAG GTC TTT GCT<br>Asp Glu Gly Cys Lys Leu Val Thr Ile Gly Ser Gly Lys Val Phe Ala<br>            745                      750                      755 | 2491 |
| TCC ACT GGC TAT GGC ATT GCC ATC CAA AAA GAT TCT GGG TGG AAG CGC<br>Ser Thr Gly Tyr Gly Ile Ala Ile Gln Lys Asp Ser Gly Trp Lys Arg<br>            760                      765                      770 | 2539 |
| CAG GTG GAC CTT GCT ATC CTG CAG CTC TTT GGA GAT GGG GAG ATG GAA<br>Gln Val Asp Leu Ala Ile Leu Gln Leu Phe Gly Asp Gly Glu Met Glu<br>775                          780                      785                      790 | 2587 |
| GAA CTG GAA GCT CTC TGG CTC ACT GGC ATT TGT CAC AAT GAG AAG AAT<br>Glu Leu Glu Ala Leu Trp Leu Thr Gly Ile Cys His Asn Glu Lys Asn<br>                795                      800                      805 | 2635 |
| GAG GTC ATG AGC AGC CAG CTG GAC ATT GAC AAC ATG GCA GGG GTC TTC<br>Glu Val Met Ser Ser Gln Leu Asp Ile Asp Asn Met Ala Gly Val Phe<br>            810                      815                      820 | 2683 |
| TAC ATG TTG GGG GCG GCC ATG GCT CTC AGC CTC ATC ACC TTC ATC TGC | 2731 |

```
              Tyr Met Leu Gly Ala Ala Met Ala Leu Ser Leu Ile Thr Phe Ile Cys
                      825                 830                 835

GAA CAC CTT TTC TAT TGG CAG TTC CGA CAT TGC TTT ATG GGT GTC TGT           2779
Glu His Leu Phe Tyr Trp Gln Phe Arg His Cys Phe Met Gly Val Cys
        840                 845                 850

TCT GGC AAG CCT GGC ATG GTC TTC TCC ATC AGC AGA GGT ATC TAC AGC           2827
Ser Gly Lys Pro Gly Met Val Phe Ser Ile Ser Arg Gly Ile Tyr Ser
855                 860                 865                 870

TGC ATC CAT GGG GTG GCG ATC GAG GAG CGC CAG TCT GTA ATG AAC TCC           2875
Cys Ile His Gly Val Ala Ile Glu Glu Arg Gln Ser Val Met Asn Ser
                875                 880                 885

CCC ACT GCA ACC ATG AAC AAC ACA CAC TCC AAC ATC CTG CGC CTG CTG           2923
Pro Thr Ala Thr Met Asn Asn Thr His Ser Asn Ile Leu Arg Leu Leu
        890                 895                 900

CGC ACG GCC AAG AAC ATG GCT AAC CTG TCT GGT GTG AAT GGC TCA CCG           2971
Arg Thr Ala Lys Asn Met Ala Asn Leu Ser Gly Val Asn Gly Ser Pro
                905                 910                 915

CAG AGG CCC CTG GAC TTC ATC CGA CGG GAG TCA TCC GTC TAT GAC ATC           3019
Gln Arg Pro Leu Asp Phe Ile Arg Arg Glu Ser Ser Val Tyr Asp Ile
        920                 925                 930

TCA GAG CAC CGC CGC AGC TTC ACG CAT TCT GAC TGC AAA TCC TAC AAC           3067
Ser Glu His Arg Arg Ser Phe Thr His Ser Asp Cys Lys Ser Tyr Asn
935                 940                 945                 950

AAC CCG CCC TGT GAG GAG AAC CTC TTC AGT GAC TAC ATC AGT GAG GTA           3115
Asn Pro Pro Cys Glu Glu Asn Leu Phe Ser Asp Tyr Ile Ser Glu Val
                955                 960                 965

GAG AGA ACG TTC GGG AAC CTG CAG CTG AAG GAC AGC AAC GTG TAC CAA           3163
Glu Arg Thr Phe Gly Asn Leu Gln Leu Lys Asp Ser Asn Val Tyr Gln
        970                 975                 980

GAT CAC TAC CAC CAT CAC CAC CGG CCC CAT AGT ATT GGC AGT GCC AGC           3211
Asp His Tyr His His His His Arg Pro His Ser Ile Gly Ser Ala Ser
                985                 990                 995

TCC ATC GAT GGG CTC TAC GAC TGT GAC AAC CCA CCC TTC ACC ACC CAG           3259
Ser Ile Asp Gly Leu Tyr Asp Cys Asp Asn Pro Pro Phe Thr Thr Gln
        1000                1005                1010

TCC AGG TCC ATC AGC AAG AAG CCC CTG GAC ATC GGC CTC CCC TCC TCC           3307
Ser Arg Ser Ile Ser Lys Lys Pro Leu Asp Ile Gly Leu Pro Ser Ser
1015                1020                1025                1030

AAG CAC AGC CAG CTC AGT GAC CTG TAC GGC AAA TTC TCC TTC AAG AGC           3355
Lys His Ser Gln Leu Ser Asp Leu Tyr Gly Lys Phe Ser Phe Lys Ser
                1035                1040                1045

GAC CGC TAC AGT GGC CAC GAC GAC TTG ATC CGC TCC GAT GTC TCT GAC           3403
Asp Arg Tyr Ser Gly His Asp Asp Leu Ile Arg Ser Asp Val Ser Asp
        1050                1055                1060

ATC TCA ACC CAC ACC GTC ACC TAT GGG AAC ATC GAG GGC AAT GCC GCC           3451
Ile Ser Thr His Thr Val Thr Tyr Gly Asn Ile Glu Gly Asn Ala Ala
                1065                1070                1075

AAG AGG CGT AAG CAG CAA TAT AAG GAC AGC CTG AAG AAG CGG CCT GCC           3499
Lys Arg Arg Lys Gln Gln Tyr Lys Asp Ser Leu Lys Lys Arg Pro Ala
        1080                1085                1090

TCG GCC AAG TCC CGC AGG GAG TTT GAC GAG ATC GAG CTG GCC TAC CGT           3547
Ser Ala Lys Ser Arg Arg Glu Phe Asp Glu Ile Glu Leu Ala Tyr Arg
1095                1100                1105                1110

CGC CGA CCG CCC CGC TCC CCT GAC CAC AAG CGC TAC TTC AGG GAC AAG           3595
Arg Arg Pro Pro Arg Ser Pro Asp His Lys Arg Tyr Phe Arg Asp Lys
                1115                1120                1125

GAA GGG CTA CGG GAC TTC TAC CTG GAC CAG TTC CGA ACA AAG GAG AAC           3643
Glu Gly Leu Arg Asp Phe Tyr Leu Asp Gln Phe Arg Thr Lys Glu Asn
        1130                1135                1140
```

```
TCA CCC CAC TGG GAG CAC GTA GAC CTG ACC GAC ATC TAC AAG GAG CGG    3691
Ser Pro His Trp Glu His Val Asp Leu Thr Asp Ile Tyr Lys Glu Arg
        1145                1150                1155

AGT GAT GAC TTT AAG CGC GAC TCC GTC AGC GGA GGA GGG CCC TGT ACC    3739
Ser Asp Asp Phe Lys Arg Asp Ser Val Ser Gly Gly Gly Pro Cys Thr
    1160                1165                1170

AAC AGG TCT CAC ATC AAG CAC GGG ACG GGC GAC AAA CAC GGC GTG GTC    3787
Asn Arg Ser His Ile Lys His Gly Thr Gly Asp Lys His Gly Val Val
1175                1180                1185                1190

AGC GGG GTA CCT GCA CCT TGG GAG AAG AAC CTG ACC AAC GTG GAG TGG    3835
Ser Gly Val Pro Ala Pro Trp Glu Lys Asn Leu Thr Asn Val Glu Trp
            1195                1200                1205

GAG GAC CGG TCC GGG GGC AAC TTC TGC CGC AGC TGT CCC TCC AAG CTG    3883
Glu Asp Arg Ser Gly Gly Asn Phe Cys Arg Ser Cys Pro Ser Lys Leu
        1210                1215                1220

CAC AAC TAC TCC ACG ACG GTG ACG GGT CAG AAC TCG GGC AGG CAG GCG    3931
His Asn Tyr Ser Thr Thr Val Thr Gly Gln Asn Ser Gly Arg Gln Ala
    1225                1230                1235

TGC ATC CGG TGT GAG GCT TGC AAG AAA GCA GGC AAC CTG TAT GAC ATC    3979
Cys Ile Arg Cys Glu Ala Cys Lys Lys Ala Gly Asn Leu Tyr Asp Ile
1240                1245                1250

AGT GAG GAC AAC TCC CTG CAG GAA CTG GAC CAG CCG GCT GCC CCA GTG    4027
Ser Glu Asp Asn Ser Leu Gln Glu Leu Asp Gln Pro Ala Ala Pro Val
1255                1260                1265                1270

GCG GTG ACG TCA AAC GCC TCC ACC ACT AAG TAC CCT CAG AGC CCG ACT    4075
Ala Val Thr Ser Asn Ala Ser Thr Thr Lys Tyr Pro Gln Ser Pro Thr
            1275                1280                1285

AAT TCC AAG GCC CAG AAG AAG AAC CGG AAC AAA CTG CGC CGG CAG CAC    4123
Asn Ser Lys Ala Gln Lys Lys Asn Arg Asn Lys Leu Arg Arg Gln His
        1290                1295                1300

TCC TAC GAC ACC TTC GTG GAC CTG CAG AAG GAA GAA GCC GCC CTG GCC    4171
Ser Tyr Asp Thr Phe Val Asp Leu Gln Lys Glu Glu Ala Ala Leu Ala
    1305                1310                1315

CCG CGC AGC GTA AGC CTG AAA GAC AAG GGC CGA TTC ATG GAT GGG AGC    4219
Pro Arg Ser Val Ser Leu Lys Asp Lys Gly Arg Phe Met Asp Gly Ser
1320                1325                1330

CCC TAC GCC CAC ATG TTT GAG ATG TCA GCT GGC GAG AGC ACC TTT GCC    4267
Pro Tyr Ala His Met Phe Glu Met Ser Ala Gly Glu Ser Thr Phe Ala
1335                1340                1345                1350

AAC AAC AAG TCC TCA GTG CCC ACT GCC GGA CAT CAC CAC CAC AAC AAC    4315
Asn Asn Lys Ser Ser Val Pro Thr Ala Gly His His His His Asn Asn
            1355                1360                1365

CCC GGC GGC GGG TAC ATG CTC AGC AAG TCG CTC TAC CCT GAC CGG GTC    4363
Pro Gly Gly Gly Tyr Met Leu Ser Lys Ser Leu Tyr Pro Asp Arg Val
        1370                1375                1380

ACG CAA AAC CCT TTC ATC CCC ACT TTT GGG GAC GAC CAG TGC TTG CTC    4411
Thr Gln Asn Pro Phe Ile Pro Thr Phe Gly Asp Asp Gln Cys Leu Leu
    1385                1390                1395

CAT GGC AGC AAA TCC TAC TTC TTC AGG CAG CCC ACG GTG GCG GGG GCG    4459
His Gly Ser Lys Ser Tyr Phe Phe Arg Gln Pro Thr Val Ala Gly Ala
1400                1405                1410

TCG AAA GCC AGG CCG GAC TTC CGG GCC CTT GTC ACC AAC AAG CCG GTG    4507
Ser Lys Ala Arg Pro Asp Phe Arg Ala Leu Val Thr Asn Lys Pro Val
1415                1420                1425                1430

GTC TCG GCC CTT CAT GGG GCC GTG CCA GCC CGT TTC CAG AAG GAC ATC    4555
Val Ser Ala Leu His Gly Ala Val Pro Ala Arg Phe Gln Lys Asp Ile
            1435                1440                1445

TGT ATA GGG AAC CAG TCC AAC CCC TGT GTG CCT AAC AAC AAA AAC CCC    4603
Cys Ile Gly Asn Gln Ser Asn Pro Cys Val Pro Asn Asn Lys Asn Pro
        1450                1455                1460
```

```
AGG GCT TTC AAT GGC TCC AGC AAT GGG CAT GTT TAT GAG AAA CTT TCT    4651
Arg Ala Phe Asn Gly Ser Ser Asn Gly His Val Tyr Glu Lys Leu Ser
            1465                1470                1475

AGT ATT GAG TCT GAT GTC TGAGTGAGGG AACAGAGAGG TTAAGGTGGG           4699
Ser Ile Glu Ser Asp Val
            1480

TACGGGAGGG TAAGGCTGTG GGTCGCGTGA TGCGCATGTC ACGGAGGGTG ACGGGGGTGA  4759

ACTTGGTTCC CATTTGCTCC TTTCTTGTTT TAATTTATTT ATGGGGATCC TGGAGTTCTG  4819

GTTCCTACTG GGGGCAACCC TGGTGACCAG CACCATCTCT CCTCCTTTTC ACAGTTCTCT  4879

CCTTCTTCCC CCCGCTGTCA GCCATTCCTG TTCCCATGAG ATGATGCCAT GGGTCTCAGC  4939

AGGGGAGGGT AGAGCGGAGA AAGGAAGGGC AGCATGCGGG CTTCCTCCTG GTGTGGAAGA  4999

GCTCCTTGAT ATCCTCTTTG AGTGAAGCTG GGAGAACCAA AAAGAGGCTA TGTGAGCACA  5059

AAGGTAGCTT TTCCCAAACT GATCTTTTCA TTTAGGTGAG GAAGCAAAAG CATCTATGTG  5119

AGACCATTTA GCACACTGCT TGTGAAAGGA AAGAGGCTCT GGCTAAATTC ATGCTGCTTA  5179

GATGACATCT GTCTAGGAAT CATGTGCCAA GCAGAGGTTG GGAGGCCATT TGTGTTTATA  5239

TATAAGCCAA AAAATGCTTG CTTCAACCCC ATGAGACTCG ATAGTGGTGG TGAACAGAAC  5299

AAAAGGTCAT TGGTGGCAGA GTGGATTCTT GAACAAACTG GAAAGTACGT TATGATAGTG  5359

TCCCACGGTG CCTTGGGGAC AAGAGCAGGT GGATTGTGCG TGCATGTGTG TTCATGCACA  5419

CTTGCACCCA TGTGTAGTCA GGTGCCTCAA GAGAAGGCAA CCTTGACTCT TTCTATTGTT  5479

TCTTTCAATA TCCCCAAGCA GTGTGATTGT TTGGCTTATA TACAGACAGA GATGGCCATG  5539

TATTACCTGA ATTTTGGCTG TGTCTCCCTT CATCCTTCTG GAATAAGGAG AATGAAAATT  5599

CTTGATAAAG AAGATTCTGT GGTCTAAACA AAAAAAGGCG GTGAGCAATC CTGCAAGAGC  5659

AAGGTACATA AACAAGTCCT CAGTGGTTGG CAACTGTTTC AACCTGTTTG AACCAAGAAC  5719

CTTCCAGGAA GGCTAAAGGG AAACCGAATT TCACAGCCAT GATTCTTTTG CCCACACTTG  5779

GGAGCAAAAG ATTCTACAAA GCTCTTTTGA GCATTTAGAC TCTCGACTGG CCAAGGTTTG  5839

GGGAAGAACG AAGCCACCTT TGAAGAAGTA AGGAGTCGTG TATGGTAGGG TAAGTGAGAG  5899

AGGGGGATGT TTCCAATGCT TTGATCCCTT CTTACTTAAC CTGAAGCTAG ACGAGCAGGC  5959

TTCTTCCCCC CAAAACTGAA TTCC                                        5983

(2) INFORMATION FOR SEQ ID NO:2:

(i) SEQUENCE CHARACTERISTICS:
        (A) LENGTH: 1484 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Pro Arg Ala Glu Cys Cys Ser Pro Lys Phe Trp Leu Val Leu
 1               5                  10                  15

Ala Val Leu Ala Val Ser Gly Ser Arg Ala Arg Ser Gln Lys Ser Pro
             20                  25                  30

Pro Ser Ile Gly Ile Ala Val Ile Leu Val Gly Thr Ser Asp Glu Val
         35                  40                  45

Ala Ile Lys Asp Ala His Glu Lys Asp Asp Phe His His Leu Ser Val
     50                  55                  60

Val Pro Arg Val Glu Leu Val Ala Met Asn Glu Thr Asp Pro Lys Ser
65                  70                  75                  80
```

-continued

```
Ile Ile Thr Arg Ile Cys Asp Leu Met Ser Asp Arg Lys Ile Gln Gly
                85                  90                  95
Val Val Phe Ala Asp Asp Thr Asp Gln Glu Ala Ile Ala Gln Ile Leu
            100                 105                 110
Asp Phe Ile Ser Ala Gln Thr Leu Thr Pro Ile Leu Gly Ile His Gly
            115                 120                 125
Gly Ser Ser Met Ile Met Ala Asp Lys Asp Glu Ser Ser Met Phe Phe
    130                 135                 140
Gln Phe Gly Pro Ser Ile Glu Gln Gln Ala Ser Val Met Leu Asn Ile
145                 150                 155                 160
Met Glu Glu Tyr Asp Trp Tyr Ile Phe Ser Ile Val Thr Thr Tyr Phe
                165                 170                 175
Pro Gly Tyr Gln Asp Phe Val Asn Lys Ile Arg Ser Thr Ile Glu Asn
                180                 185                 190
Ser Phe Val Gly Trp Glu Leu Glu Glu Val Leu Leu Leu Asp Met Ser
            195                 200                 205
Leu Asp Asp Gly Asp Ser Lys Ile Gln Asn Gln Leu Lys Lys Leu Gln
            210                 215                 220
Ser Pro Ile Ile Leu Leu Tyr Cys Thr Lys Glu Glu Ala Thr Tyr Ile
225                 230                 235                 240
Phe Glu Val Ala Asn Ser Val Gly Leu Thr Gly Tyr Gly Tyr Thr Trp
                245                 250                 255
Ile Val Pro Ser Leu Val Ala Gly Asp Thr Asp Thr Val Pro Ala Glu
                260                 265                 270
Phe Pro Thr Gly Leu Ile Ser Val Ser Tyr Asp Glu Trp Asp Tyr Gly
            275                 280                 285
Leu Pro Ala Arg Val Arg Asp Gly Ile Ala Ile Thr Thr Ala Ala
    290                 295                 300
Ser Asp Met Leu Ser Glu His Ser Phe Ile Pro Glu Pro Lys Ser Ser
305                 310                 315                 320
Cys Tyr Asn Thr His Glu Lys Arg Ile Tyr Gln Ser Asn Met Leu Asn
                325                 330                 335
Arg Tyr Leu Ile Asn Val Thr Phe Glu Gly Arg Asn Leu Ser Phe Ser
            340                 345                 350
Glu Asp Gly Tyr Gln Met His Pro Lys Leu Val Ile Ile Leu Leu Asn
            355                 360                 365
Lys Glu Arg Lys Trp Glu Arg Val Gly Lys Trp Lys Asp Lys Ser Leu
            370                 375                 380
Gln Met Lys Tyr Tyr Val Trp Pro Arg Met Cys Pro Glu Thr Glu Glu
385                 390                 395                 400
Gln Glu Asp Asp His Leu Ser Ile Val Thr Leu Glu Glu Ala Pro Phe
                405                 410                 415
Val Ile Val Glu Ser Val Asp Pro Leu Ser Gly Thr Cys Met Arg Asn
            420                 425                 430
Thr Val Pro Cys Gln Lys Arg Ile Val Thr Glu Asn Lys Thr Asp Glu
            435                 440                 445
Glu Pro Gly Tyr Ile Lys Lys Cys Cys Lys Gly Phe Cys Ile Asp Ile
    450                 455                 460
Leu Lys Lys Ile Ser Lys Ser Val Lys Phe Thr Tyr Asp Leu Tyr Leu
465                 470                 475                 480
Val Thr Asn Gly Lys His Gly Lys Lys Ile Asn Gly Thr Trp Asn Gly
                485                 490                 495
```

-continued

```
Met Ile Gly Glu Val Val Met Lys Arg Ala Tyr Met Ala Val Gly Ser
            500                 505                 510

Leu Thr Ile Asn Glu Glu Arg Ser Glu Val Val Asp Phe Ser Val Pro
            515                 520                 525

Phe Ile Glu Thr Gly Ile Ser Val Met Val Ser Arg Ser Asn Gly Thr
            530                 535                 540

Val Ser Pro Ser Ala Phe Leu Glu Pro Phe Ser Ala Asp Val Trp Val
545                 550                 555                 560

Met Met Phe Val Met Leu Leu Ile Val Ser Ala Val Ala Val Phe Val
            565                 570                 575

Phe Glu Tyr Phe Ser Pro Val Gly Tyr Asn Arg Cys Leu Ala Asp Gly
            580                 585                 590

Arg Glu Pro Gly Gly Pro Ser Phe Thr Ile Gly Lys Ala Ile Trp Leu
            595                 600                 605

Leu Trp Gly Leu Val Phe Asn Asn Ser Val Pro Val Gln Asn Pro Lys
            610                 615                 620

Gly Thr Thr Ser Lys Ile Met Val Ser Val Trp Ala Phe Phe Ala Val
625                 630                 635                 640

Ile Phe Leu Ala Ser Tyr Thr Ala Asn Leu Ala Ala Phe Met Ile Gln
            645                 650                 655

Glu Glu Tyr Val Asp Gln Val Ser Gly Leu Ser Asp Lys Lys Phe Gln
            660                 665                 670

Arg Pro Asn Asp Phe Ser Pro Pro Phe Arg Phe Gly Thr Val Pro Asn
            675                 680                 685

Gly Ser Thr Glu Arg Asn Ile Arg Asn Asn Tyr Ala Glu Met His Ala
            690                 695                 700

Tyr Met Gly Lys Phe Asn Gln Arg Gly Val Asp Asp Ala Leu Leu Ser
705                 710                 715                 720

Leu Lys Thr Gly Lys Leu Asp Ala Phe Ile Tyr Asp Ala Ala Val Leu
            725                 730                 735

Asn Tyr Met Ala Gly Arg Asp Glu Gly Cys Lys Leu Val Thr Ile Gly
            740                 745                 750

Ser Gly Lys Val Phe Ala Ser Thr Gly Tyr Gly Ile Ala Ile Gln Lys
            755                 760                 765

Asp Ser Gly Trp Lys Arg Gln Val Asp Leu Ala Ile Leu Gln Leu Phe
            770                 775                 780

Gly Asp Gly Glu Met Glu Glu Leu Glu Ala Leu Trp Leu Thr Gly Ile
785                 790                 795                 800

Cys His Asn Glu Lys Asn Glu Val Met Ser Ser Gln Leu Asp Ile Asp
            805                 810                 815

Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
            850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
            885                 890                 895

Asn Ile Leu Arg Leu Leu Arg Thr Ala Lys Asn Met Ala Asn Leu Ser
            900                 905                 910

Gly Val Asn Gly Ser Pro Gln Arg Pro Leu Asp Phe Ile Arg Arg Glu
```

-continued

```
                915                 920                 925
Ser Ser Val Tyr Asp Ile Ser Glu His Arg Arg Ser Phe Thr His Ser
            930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
            965                 970                 975

Asp Ser Asn Val Tyr Gln Asp His Tyr His His His Arg Pro His
            980                 985                 990

Ser Ile Gly Ser Ala Ser Ser Ile Asp Gly Leu Tyr Asp Cys Asp Asn
            995                 1000                1005

Pro Pro Phe Thr Thr Gln Ser Arg Ser Ile Ser Lys Lys Pro Leu Asp
            1010                1015                1020

Ile Gly Leu Pro Ser Ser Lys His Ser Gln Leu Ser Asp Leu Tyr Gly
1025                1030                1035                1040

Lys Phe Ser Phe Lys Ser Asp Arg Tyr Ser Gly His Asp Asp Leu Ile
                1045                1050                1055

Arg Ser Asp Val Ser Asp Ile Ser Thr His Thr Val Thr Tyr Gly Asn
            1060                1065                1070

Ile Glu Gly Asn Ala Ala Lys Arg Arg Lys Gln Gln Tyr Lys Asp Ser
            1075                1080                1085

Leu Lys Lys Arg Pro Ala Ser Ala Lys Ser Arg Arg Glu Phe Asp Glu
            1090                1095                1100

Ile Glu Leu Ala Tyr Arg Arg Arg Pro Pro Arg Ser Pro Asp His Lys
1105                1110                1115                1120

Arg Tyr Phe Arg Asp Lys Glu Gly Leu Arg Asp Phe Tyr Leu Asp Gln
                1125                1130                1135

Phe Arg Thr Lys Glu Asn Ser Pro His Trp Glu His Val Asp Leu Thr
            1140                1145                1150

Asp Ile Tyr Lys Glu Arg Ser Asp Asp Phe Lys Arg Asp Ser Val Ser
            1155                1160                1165

Gly Gly Gly Pro Cys Thr Asn Arg Ser His Ile Lys His Gly Thr Gly
            1170                1175                1180

Asp Lys His Gly Val Val Ser Gly Val Pro Ala Pro Trp Glu Lys Asn
1185                1190                1195                1200

Leu Thr Asn Val Glu Trp Glu Asp Arg Ser Gly Gly Asn Phe Cys Arg
                1205                1210                1215

Ser Cys Pro Ser Lys Leu His Asn Tyr Ser Thr Val Thr Gly Gln
            1220                1225                1230

Asn Ser Gly Arg Gln Ala Cys Ile Arg Cys Glu Ala Cys Lys Lys Ala
            1235                1240                1245

Gly Asn Leu Tyr Asp Ile Ser Glu Asp Asn Ser Leu Gln Glu Leu Asp
            1250                1255                1260

Gln Pro Ala Ala Pro Val Ala Val Thr Ser Asn Ala Ser Thr Thr Lys
1265                1270                1275                1280

Tyr Pro Gln Ser Pro Thr Asn Ser Lys Ala Gln Lys Lys Asn Arg Asn
                1285                1290                1295

Lys Leu Arg Arg Gln His Ser Tyr Asp Thr Phe Val Asp Leu Gln Lys
            1300                1305                1310

Glu Glu Ala Ala Leu Ala Pro Arg Ser Val Ser Leu Lys Asp Lys Gly
            1315                1320                1325

Arg Phe Met Asp Gly Ser Pro Tyr Ala His Met Phe Glu Met Ser Ala
            1330                1335                1340
```

```
Gly Glu Ser Thr Phe Ala Asn Asn Lys Ser Ser Val Pro Thr Ala Gly
1345                1350                1355                1360

His His His His Asn Asn Pro Gly Gly Gly Tyr Met Leu Ser Lys Ser
                1365                1370                1375

Leu Tyr Pro Asp Arg Val Thr Gln Asn Pro Phe Ile Pro Thr Phe Gly
            1380                1385                1390

Asp Asp Gln Cys Leu Leu His Gly Ser Lys Ser Tyr Phe Phe Arg Gln
                1395                1400                1405

Pro Thr Val Ala Gly Ala Ser Lys Ala Arg Pro Asp Phe Arg Ala Leu
            1410                1415                1420

Val Thr Asn Lys Pro Val Val Ser Ala Leu His Gly Ala Val Pro Ala
1425                1430                1435                1440

Arg Phe Gln Lys Asp Ile Cys Ile Gly Asn Gln Ser Asn Pro Cys Val
                1445                1450                1455

Pro Asn Asn Lys Asn Pro Arg Ala Phe Asn Gly Ser Ser Asn Gly His
                1460                1465                1470

Val Tyr Glu Lys Leu Ser Ser Ile Glu Ser Asp Val
            1475                1480
```

(2) INFORMATION FOR SEQ ID NO:3:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:3:

```
Tyr Val Trp Pro Arg Met Cys Pro Glu Thr Glu Gln Glu Asp Asp
1               5                   10                  15

His Leu Ser Ile
            20
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (xi) SEQUENCE DESCRIPTION: SEQ ID NO:4:

```
CTATGTGTGG CCCCGAATGT GTCCAGAGAC TGAAGAGCAG GAGGATGACC ATCTGAGCAT     60
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (xi) SEQUENCE DESCRIPTION: SEQ ID NO:5:

```
CTATGTGTGG CCCCGAATGT GTCCAGAGAC TGAAGAGCAG GAGGATGACC ATCTGAACAT     60
```

(2) INFORMATION FOR SEQ ID NO:6:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:6:

Tyr Val Trp Pro Arg Met Cys Pro Glu Thr Glu Glu Gln Glu Asp Asp
1               5                   10                  15

His Leu Asn Ile
            20

(2) INFORMATION FOR SEQ ID NO:7:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1785

(xi) SEQUENCE DESCRIPTION: SEQ ID NO:7:

```
GCC TTC TAC AGG CAC CTA CTG AAT GTC ACC TGG GAG GGC CGA GAC TTC        48
Ala Phe Tyr Arg His Leu Leu Asn Val Thr Trp Glu Gly Arg Asp Phe
 1               5                   10                  15

TCC TTC AGC CCT GGT GGG TAC CTG GTC CAG CCC ACC ATG GTG GTG ATC        96
Ser Phe Ser Pro Gly Gly Tyr Leu Val Gln Pro Thr Met Val Val Ile
                20                  25                  30

GCC CTC AAC CGG CAC CGC CTC TGG GAG ATG GTG GGG CGC TGG GAG CAT       144
Ala Leu Asn Arg His Arg Leu Trp Glu Met Val Gly Arg Trp Glu His
            35                  40                  45

GGC GTC CTA TAC ATG AAG TAC CCC GTG TGG CCT CGC TAC AGT GCC TCT       192
Gly Val Leu Tyr Met Lys Tyr Pro Val Trp Pro Arg Tyr Ser Ala Ser
        50                  55                  60

CTG CAG CCT GTG GTG GAC AGT CGG CAC CTG ACG GTG GCC ACG CTG GAA       240
Leu Gln Pro Val Val Asp Ser Arg His Leu Thr Val Ala Thr Leu Glu
65                  70                  75                  80

GAG CGG CCC TTT GTC ATC GTG GAG AGC CCT GAC CCT GGC ACA GGA GGC       288
Glu Arg Pro Phe Val Ile Val Glu Ser Pro Asp Pro Gly Thr Gly Gly
                85                  90                  95

TGT GTC CCC AAC ACC GTG CCC TGC CGC AGG CAG AGC AAC CAC ACC TTC       336
Cys Val Pro Asn Thr Val Pro Cys Arg Arg Gln Ser Asn His Thr Phe
            100                 105                 110

AGC AGC GGG GAC GTG GCC CCC TAC ACC AAG CTC TGC TGT AAG GGA TTC       384
Ser Ser Gly Asp Val Ala Pro Tyr Thr Lys Leu Cys Cys Lys Gly Phe
        115                 120                 125

TGC ATC GAC ATC CTC AAG AAG CTG GCC AGA GTG GTC AAA TTC TCC TAC       432
Cys Ile Asp Ile Leu Lys Lys Leu Ala Arg Val Val Lys Phe Ser Tyr
    130                 135                 140

GAC CTG TAC CTG GTG ACC AAC GGC AAG CAT GGC AAG CGG GTG CGC GGC       480
Asp Leu Tyr Leu Val Thr Asn Gly Lys His Gly Lys Arg Val Arg Gly
145                 150                 155                 160

GTA TGG AAC GGC ATG ATT GGG GAG GTG TAC TAC AAG CGG GCA GAC ATG       528
Val Trp Asn Gly Met Ile Gly Glu Val Tyr Tyr Lys Arg Ala Asp Met
                165                 170                 175

GCC ATC GGC TCC CTC ACC ATC AAT GAG GAA CGC TCC GAG ATC GTA GAC       576
Ala Ile Gly Ser Leu Thr Ile Asn Glu Glu Arg Ser Glu Ile Val Asp
            180                 185                 190

TTC TCT GTA CCC TTT GTG GAG ACG GGC ATC AGT GTG ATG GTG GCT CGC       624
Phe Ser Val Pro Phe Val Glu Thr Gly Ile Ser Val Met Val Ala Arg
        195                 200                 205

AGC AAT GGC ACC GTC TCC CCC TCG GCC TTC TTG GAG CCA TAT AGC CCT       672
Ser Asn Gly Thr Val Ser Pro Ser Ala Phe Leu Glu Pro Tyr Ser Pro
    210                 215                 220

GCA GTG TGG GTG ATG ATG TTT GTC ATG TGC CTC ACT GTG GTG GCC ATC       720
```

```
Ala Val Trp Val Met Met Phe Val Met Cys Leu Thr Val Val Ala Ile
225                 230                 235                 240

ACC GTC TTC ATG TTC GAG TAC TTC AGC CCT GTC AGC TAC AAC CAG AAC     768
Thr Val Phe Met Phe Glu Tyr Phe Ser Pro Val Ser Tyr Asn Gln Asn
                245                 250                 255

CTC ACC AGA GGC AAG AAG TCC GGG GGC CCA GCT TTC ACT ATC GGC AAG     816
Leu Thr Arg Gly Lys Lys Ser Gly Gly Pro Ala Phe Thr Ile Gly Lys
            260                 265                 270

TCC GTG TGG CTG CTG TGG GCG CTG GTC TTC AAC AAC TCA GTG CCC ATC     864
Ser Val Trp Leu Leu Trp Ala Leu Val Phe Asn Asn Ser Val Pro Ile
                275                 280                 285

GAG AAC CCG CGG GGC ACC ACC AGC AAG ATC ATG GTT CTG GTC TGG GCC     912
Glu Asn Pro Arg Gly Thr Thr Ser Lys Ile Met Val Leu Val Trp Ala
290                 295                 300

TTC TTT GCT GTC ATC TTC CTC GCC AGC TAC ACG GCC AAC CTG GCC GCC     960
Phe Phe Ala Val Ile Phe Leu Ala Ser Tyr Thr Ala Asn Leu Ala Ala
305                 310                 315                 320

TTC ATG ATC CAA GAG CAA TAC ATC GAC ACT GTG TCG GGC CTC AGT GAC    1008
Phe Met Ile Gln Glu Gln Tyr Ile Asp Thr Val Ser Gly Leu Ser Asp
                325                 330                 335

AAG AAG TTT CAG CGG CCT CAA GAT CAG TAC CCA CCT TTC CGC TTC GGC    1056
Lys Lys Phe Gln Arg Pro Gln Asp Gln Tyr Pro Pro Phe Arg Phe Gly
                340                 345                 350

ACG GTG CCC AAC GGC AGC ACG GAG CGG AAC ATC CGC AGT AAC TAC CGT    1104
Thr Val Pro Asn Gly Ser Thr Glu Arg Asn Ile Arg Ser Asn Tyr Arg
            355                 360                 365

GAC ATG CAC ACC CAC ATG GTC AAG TTC AAC CAG CGC TCG GTG GAG GAC    1152
Asp Met His Thr His Met Val Lys Phe Asn Gln Arg Ser Val Glu Asp
370                 375                 380

GCG CTC ACC AGC CTC AAG ATG GGG AAG CTG GAT GCC TTC ATC TAT GAT    1200
Ala Leu Thr Ser Leu Lys Met Gly Lys Leu Asp Ala Phe Ile Tyr Asp
385                 390                 395                 400

GCT GCT GTC CTC AAC TAC ATG GCA GGC AAG GAC GAG GGC TGC AAG CTG    1248
Ala Ala Val Leu Asn Tyr Met Ala Gly Lys Asp Glu Gly Cys Lys Leu
                405                 410                 415

GTC ACC ATT GGG TCT GGC AAG GTC TTT GCT ACC ACT GGC TAC GGC ATC    1296
Val Thr Ile Gly Ser Gly Lys Val Phe Ala Thr Thr Gly Tyr Gly Ile
                420                 425                 430

GCC ATG CAG AAG GAC TCC CAC TGG AAG CGG GCC ATA GAC CTG GCG CTC    1344
Ala Met Gln Lys Asp Ser His Trp Lys Arg Ala Ile Asp Leu Ala Leu
            435                 440                 445

TTG CAG TTC CTG GGG GAC GGA GAG ACA CAG AAA CTG GAG ACA GTG TGG    1392
Leu Gln Phe Leu Gly Asp Gly Glu Thr Gln Lys Leu Glu Thr Val Trp
            450                 455                 460

CTC TCA GGG ATC TGC CAG AAT GAG AAG AAC GAG GTG ATG AGC AGC AAG    1440
Leu Ser Gly Ile Cys Gln Asn Glu Lys Asn Glu Val Met Ser Ser Lys
465                 470                 475                 480

CTG GAC ATC GAC AAC ATG GCA GGC GTC TTC TAC ATG CTG CTG GTG GCC    1488
Leu Asp Ile Asp Asn Met Ala Gly Val Phe Tyr Met Leu Leu Val Ala
                485                 490                 495

ATG GGG CTG GCC CTG CTG GTC TTC GCC TGG GAG CAC CTG GTC TAC TGG    1536
Met Gly Leu Ala Leu Leu Val Phe Ala Trp Glu His Leu Val Tyr Trp
                500                 505                 510

AAG CTG CGC CAC TCG GTG CCC AAC TCA TCC CAG CTG GAC TTC CTG CTG    1584
Lys Leu Arg His Ser Val Pro Asn Ser Ser Gln Leu Asp Phe Leu Leu
                515                 520                 525

GCT TTC AGC AGG GGC ATC TAC AGC TGC TTC AGC GGG GTG CAG AGC CTC    1632
Ala Phe Ser Arg Gly Ile Tyr Ser Cys Phe Ser Gly Val Gln Ser Leu
                530                 535                 540
```

```
GCC AGC CCA CCG CGG CAG GCC AGC CCG GAC CTC ACG GCC AGC TCG GCC        1680
Ala Ser Pro Pro Arg Gln Ala Ser Pro Asp Leu Thr Ala Ser Ser Ala
545             550                 555                 560

CAG GCC AGC GTG CTC AAG ATC GTG CAG GCA GCC CGC GAC ATG GTG ACC        1728
Gln Ala Ser Val Leu Lys Ile Val Gln Ala Ala Arg Asp Met Val Thr
                565                 570                 575

ACG GCG GGC GTA AGC AGC TCC CTG GAC CGC GCC ACT CGC ACC ATC GAG        1776
Thr Ala Gly Val Ser Ser Ser Leu Asp Arg Ala Thr Arg Thr Ile Glu
            580                 585                 590

AAT TGG GGT                                                            1785
Asn Trp Gly
        595

(2) INFORMATION FOR SEQ ID NO:8:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:8:

Ala Phe Tyr Arg His Leu Leu Asn Val Thr Trp Glu Gly Arg Asp Phe
1               5                   10                  15

Ser Phe Ser Pro Gly Gly Tyr Leu Val Gln Pro Thr Met Val Val Ile
            20                  25                  30

Ala Leu Asn Arg His Arg Leu Trp Glu Met Val Gly Arg Trp Glu His
        35                  40                  45

Gly Val Leu Tyr Met Lys Tyr Pro Val Trp Pro Arg Tyr Ser Ala Ser
    50                  55                  60

Leu Gln Pro Val Val Asp Ser Arg His Leu Thr Val Ala Thr Leu Glu
65                  70                  75                  80

Glu Arg Pro Phe Val Ile Val Glu Ser Pro Asp Pro Gly Thr Gly Gly
                85                  90                  95

Cys Val Pro Asn Thr Val Pro Cys Arg Arg Gln Ser Asn His Thr Phe
            100                 105                 110

Ser Ser Gly Asp Val Ala Pro Tyr Thr Lys Leu Cys Cys Lys Gly Phe
        115                 120                 125

Cys Ile Asp Ile Leu Lys Lys Leu Ala Arg Val Val Lys Phe Ser Tyr
    130                 135                 140

Asp Leu Tyr Leu Val Thr Asn Gly Lys His Gly Lys Arg Val Arg Gly
145                 150                 155                 160

Val Trp Asn Gly Met Ile Gly Glu Val Tyr Tyr Lys Arg Ala Asp Met
                165                 170                 175

Ala Ile Gly Ser Leu Thr Ile Asn Glu Glu Arg Ser Glu Ile Val Asp
            180                 185                 190

Phe Ser Val Pro Phe Val Glu Thr Gly Ile Ser Val Met Val Ala Arg
        195                 200                 205

Ser Asn Gly Thr Val Ser Pro Ser Ala Phe Leu Glu Pro Tyr Ser Pro
    210                 215                 220

Ala Val Trp Val Met Met Phe Val Met Cys Leu Thr Val Val Ala Ile
225                 230                 235                 240

Thr Val Phe Met Phe Glu Tyr Phe Ser Pro Val Ser Tyr Asn Gln Asn
                245                 250                 255

Leu Thr Arg Gly Lys Lys Ser Gly Gly Pro Ala Phe Thr Ile Gly Lys
            260                 265                 270
```

Ser Val Trp Leu Leu Trp Ala Leu Val Phe Asn Asn Ser Val Pro Ile
            275                 280                 285

Glu Asn Pro Arg Gly Thr Thr Ser Lys Ile Met Val Leu Val Trp Ala
        290                 295                 300

Phe Phe Ala Val Ile Phe Leu Ala Ser Tyr Thr Ala Asn Leu Ala Ala
305                 310                 315                 320

Phe Met Ile Gln Glu Gln Tyr Ile Asp Thr Val Ser Gly Leu Ser Asp
                325                 330                 335

Lys Lys Phe Gln Arg Pro Gln Asp Gln Tyr Pro Pro Phe Arg Phe Gly
            340                 345                 350

Thr Val Pro Asn Gly Ser Thr Glu Arg Asn Ile Arg Ser Asn Tyr Arg
        355                 360                 365

Asp Met His Thr His Met Val Lys Phe Asn Gln Arg Ser Val Glu Asp
    370                 375                 380

Ala Leu Thr Ser Leu Lys Met Gly Lys Leu Asp Ala Phe Ile Tyr Asp
385                 390                 395                 400

Ala Ala Val Leu Asn Tyr Met Ala Gly Lys Asp Glu Gly Cys Lys Leu
                405                 410                 415

Val Thr Ile Gly Ser Gly Lys Val Phe Ala Thr Thr Gly Tyr Gly Ile
            420                 425                 430

Ala Met Gln Lys Asp Ser His Trp Lys Arg Ala Ile Asp Leu Ala Leu
        435                 440                 445

Leu Gln Phe Leu Gly Asp Gly Glu Thr Gln Lys Leu Glu Thr Val Trp
    450                 455                 460

Leu Ser Gly Ile Cys Gln Asn Glu Lys Asn Glu Val Met Ser Ser Lys
465                 470                 475                 480

Leu Asp Ile Asp Asn Met Ala Gly Val Phe Tyr Met Leu Leu Val Ala
                485                 490                 495

Met Gly Leu Ala Leu Leu Val Phe Ala Trp Glu His Leu Val Tyr Trp
        500                 505                 510

Lys Leu Arg His Ser Val Pro Asn Ser Ser Gln Leu Asp Phe Leu Leu
    515                 520                 525

Ala Phe Ser Arg Gly Ile Tyr Ser Cys Phe Ser Gly Val Gln Ser Leu
530                 535                 540

Ala Ser Pro Pro Arg Gln Ala Ser Pro Asp Leu Thr Ala Ser Ser Ala
545                 550                 555                 560

Gln Ala Ser Val Leu Lys Ile Val Gln Ala Ala Arg Asp Met Val Thr
                565                 570                 575

Thr Ala Gly Val Ser Ser Ser Leu Asp Arg Ala Thr Arg Thr Ile Glu
        580                 585                 590

Asn Trp Gly
    595

(2) INFORMATION FOR SEQ ID NO:9:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (xi) SEQUENCE DESCRIPTION: SEQ ID NO:9:

TCTGGGTGAT GATGTTTGTG ATGCTGCTCA TTGTTTCTGC CATAGCTGTT TTTGTCTTTG        60

AATACTTCAG CCCTGTTGGA TACAACAGAA ACTTAGCCAA AGGGAAAGCA CCCCATGGGC       120

CTTCTTTTAC AATTGGAAAA GCTATATGGC TTCTTTGGGG CCTGGTGTTC AATAACTCCG       180

| | | | | |
|---|---|---|---|---|
|TGCCTGTCCA|GAATCCTAAA|GGGACCACCA|GCAAGATCAT|GGTATCTGTA TGGGCCTTCT 240|
|TCGCTGTCAT|ATTCCTGGCT|AGCTACACAG|CCAATCTGGC|TGCCTTCATG ATCCAAGAGG 300|
|AATTTGTGGA|CCAAGTGACC|GGCCTCAGTG|ACAAAAAGTT|TCAGAGACCT CATGACTATT 360|
|CCCCACCTTT|TCGATTTGGG|ACAGTGCCTA|ATGGAAGCAC|GGAGAGAAAC ATTCGGAATA 420|
|ACTATCCCTA|CATGCATCAG|TACATGACCA|AATTTAATCA|GAAAGGAGTA GAGGACGCCT 480|
|TGGTCAGCCT|GAAAACGGGG|AAGCTGGACG|CTTTCATCTA|CGATGCCGCA 530|

(2) INFORMATION FOR SEQ ID NO:10:

(i) SEQUENCE CHARACTERISTICS:
        (A) LENGTH: 4659 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1099..3753

(ix) FEATURE:
        (A) NAME/KEY: sig_peptide
        (B) LOCATION: 1099..1152

(ix) FEATURE:
        (A) NAME/KEY: mat_peptide
        (B) LOCATION: 1153..3753

(ix) FEATURE:
        (A) NAME/KEY: misc_feature
        (B) LOCATION: 2781..2838
        (D) OTHER INFORMATION: /function= "transmembrane domain"

(ix) FEATURE:
        (A) NAME/KEY: misc_feature
        (B) LOCATION: 2895..2958
        (D) OTHER INFORMATION: /function= "transmembrane domain"

(ix) FEATURE:
        (A) NAME/KEY: misc_feature
        (B) LOCATION: 2988..3045
        (D) OTHER INFORMATION: /function= "transmembrane domain"

(ix) FEATURE:
        (A) NAME/KEY: misc_feature
        (B) LOCATION: 3534..3597
        (D) OTHER INFORMATION: /function= "transmembrane domain"

(xi) SEQUENCE DESCRIPTION: SEQ ID NO:10:

| | | | | |
|---|---|---|---|---|
|GAATTCCGGT|AAGGCTCTGG|AAAAGGGGGC|GCTGGGAGCG|CATTGCGAGG GGGCTGGAGA 60|
|GGGAGAGAGG|AGCGGAAGCT|GAGGGTGTGA|AACGGCTGGC|CCCGAACACA CCTCGCGGCG 120|
|CTCCAGTGAT|TCCTGGTGTC|CGACCTCAGC|CCCAGTCAGT|GCGGGTCCAG TTTCCAGGCT 180|
|CTCGCGGAAG|GCCTGGCTGA|GCACATGCGG|CAGCCACGGT|CGCCCTCCCT ATTCCTCTTA 240|
|GCCCGAGGAG|GGGGGTCCCA|AGTTACATGG|CCACGCAGAT|GGGGCCTCTC CCTCATTTCT 300|
|GAACCTTGTG|GGGAGGGGAA|CCTTGAAGGG|AGCGCCCCCC|AGAGCCATGG CTTAGGGCCT 360|
|CCCCCACCCC|TCTGGAGCTC|CAGTCTGCAA|GAGTCAGGAG|CCGAAATATC GCTGACTGTG 420|
|GGTGACGACT|CTTGCGCGCA|CACACACATA|CAAGCGGGCA|CGACGCGTTC GGTCCTATTA 480|
|AAAGGCACGC|AAGGGTGCGG|CTGCACGCGG|TGACACGGAC|CCCTCTAACG TTTCCAAACT 540|
|GAGCTCCCTG|CAGGTCCCCG|ACAGCACAGG|CCCCTGTCCC|AGGACCCCTC CAGGCACGCG 600|
|CTCACACGCA|CACGCGCGCT|CCCCGGCTCA|CGCGCGCTCC|GACACACACG CTCACGCGAA 660|
|CGCAGGCGCA|CGCTCTGGCG|CGGGAGGCGC|CCCTTCGCCT|CCGTGTTGGG AAGCGGGGGC 720|

-continued

```
GGCGGGAGGG GCAGGAGACG TTGGCCCCGC TCGCGTTTCT GCAGCTGCTG CAGTCGCCGC    780

AGCGTCCGGA CCGGAACCAG CGCCGTCCGC GGAGCCGCCG CCGCCGCCGC CGGGCCCTTT    840

CCAAGCCGGG CGCTCGGAGC TGTGCCCGGC CCCGCTTCAG CACCGCGGAC AGCTCCGGCC    900

GCGTGGGGCT GAGCCGAGCC CCCGCGCACG CTTCAGCCCC CTTCCCTCGG CCGACGTCCC    960

GGGACCGCCG CTCCGGGGGA GACGTGGCGT CCGCAGCCCG CGGGGCCGGG CGAGCGCAGG   1020

ACGGCCCGGA AGCCCCGCGG GGGATGCGCC GAGGGCCCGC GTTCGCGCCG CGCAGAGCCA   1080
```

| | | | | | | |
|---|---|---|---|---|---|---|
| GGCCCGCGGC CCGAGCCC | ATG | AGC | ACC | ATG | CGC | CTG CTG ACG CTC GCC CTG | 1131 |
| | Met | Ser | Thr | Met | Arg | Leu Leu Thr Leu Ala Leu | |
| | -18 | | | -15 | | -10 | |

```
CTG TTC TCC TGC TCC GTC GCC CGT GCC GCG TGC GAC CCC AAG ATC GTC   1179
Leu Phe Ser Cys Ser Val Ala Arg Ala Ala Cys Asp Pro Lys Ile Val
         -5                  1                5

AAC ATT GGC GCG GTG CTG AGC ACG CGG AAG CAC GAG CAG ATG TTC CGC   1227
Asn Ile Gly Ala Val Leu Ser Thr Arg Lys His Glu Gln Met Phe Arg
 10              15              20                  25

GAG GCC GTG AAC CAG GCC AAC AAG CGG CAC GGC TCC TGG AAG ATT CAG   1275
Glu Ala Val Asn Gln Ala Asn Lys Arg His Gly Ser Trp Lys Ile Gln
                 30              35                  40

CTC AAT GCC ACC TCC GTC ACG CAC AAG CCC AAC GCC ATC CAG ATG GCT   1323
Leu Asn Ala Thr Ser Val Thr His Lys Pro Asn Ala Ile Gln Met Ala
             45              50              55

CTG TCG GTG TGC GAG GAC CTC ATC TCC AGC CAG GTC TAC GCC ATC CTA   1371
Leu Ser Val Cys Glu Asp Leu Ile Ser Ser Gln Val Tyr Ala Ile Leu
         60              65              70

GTT AGC CAT CCA CCT ACC CCC AAC GAC CAC TTC ACT CCC ACC CCT GTC   1419
Val Ser His Pro Pro Thr Pro Asn Asp His Phe Thr Pro Thr Pro Val
 75              80              85

TCC TAC ACA GCC GGC TTC TAC CGC ATA CCC GTG CTG GGG CTG ACC ACC   1467
Ser Tyr Thr Ala Gly Phe Tyr Arg Ile Pro Val Leu Gly Leu Thr Thr
 90              95              100                 105

CGC ATG TCC ATC TAC TCG GAC AAG AGC ATC CAC CTG AGC TTC CTG CGC   1515
Arg Met Ser Ile Tyr Ser Asp Lys Ser Ile His Leu Ser Phe Leu Arg
                 110             115                 120

ACC GTG CCG CCC TAC TCC CAC CAG TCC AGC GTG TGG TTT GAG ATG ATG   1563
Thr Val Pro Pro Tyr Ser His Gln Ser Ser Val Trp Phe Glu Met Met
             125             130                 135

CGT GTC TAC AGC TGG AAC CAC ATC ATC CTG CTG GTC AGC GAC GAC CAC   1611
Arg Val Tyr Ser Trp Asn His Ile Ile Leu Leu Val Ser Asp Asp His
         140             145                 150

GAG GGC CGG GCG GCT CAG AAA CGC CTG GAG ACG CTG CTG GAG GAG CGT   1659
Glu Gly Arg Ala Ala Gln Lys Arg Leu Glu Thr Leu Leu Glu Glu Arg
     155             160             165

GAG TCC AAG GCA GAG AAG GTG CTG CAG TTT GAC CCA GGG ACC AAG AAC   1707
Glu Ser Lys Ala Glu Lys Val Leu Gln Phe Asp Pro Gly Thr Lys Asn
170             175             180             185

GTG ACG GCC CTG CTG ATG GAG GCG AAA GAG CTG GAG GCC CGG GTC ATC   1755
Val Thr Ala Leu Leu Met Glu Ala Lys Glu Leu Glu Ala Arg Val Ile
                 190             195                 200

ATC CTT TCT GCC AGC GAG GAC GAT GCT GCC ACT GTA TAC CGC GCA GCC   1803
Ile Leu Ser Ala Ser Glu Asp Asp Ala Ala Thr Val Tyr Arg Ala Ala
             205             210                 215

GCG ATG CTG AAC ATG ACG GGC TCC GGG TAC GTG TGG CTG GTC GGC GAG   1851
Ala Met Leu Asn Met Thr Gly Ser Gly Tyr Val Trp Leu Val Gly Glu
         220             225             230

CGC GAG ATC TCG GGG AAC GCC CTG CGC TAC GCC CCA GAC GGC ATC CTC   1899
Arg Glu Ile Ser Gly Asn Ala Leu Arg Tyr Ala Pro Asp Gly Ile Leu
```

```
                235                 240                 245
GGG CTG CAG CTC ATC AAC GGC AAG AAC GAG TCG GCC CAC ATC AGC GAC    1947
Gly Leu Gln Leu Ile Asn Gly Lys Asn Glu Ser Ala His Ile Ser Asp
250                 255                 260                 265

GCC GTG GGC GTG GTG GCC CAG GCC GTG CAC GAG CTC CTC GAG AAG GAG    1995
Ala Val Gly Val Val Ala Gln Ala Val His Glu Leu Leu Glu Lys Glu
                    270                 275                 280

AAC ATC ACC GAC CCG CCG CGG GGC TGC GTG GGC AAC ACC AAC ATC TGG    2043
Asn Ile Thr Asp Pro Pro Arg Gly Cys Val Gly Asn Thr Asn Ile Trp
            285                 290                 295

AAG ACC GGG CCG CTC TTC AAG AGA GTG CTG ATG TCT TCC AAG TAT GCG    2091
Lys Thr Gly Pro Leu Phe Lys Arg Val Leu Met Ser Ser Lys Tyr Ala
        300                 305                 310

GAT GGG GTG ACT GGT CGC GTG GAG TTC AAT GAG GAT GGG GAC CGG AAG    2139
Asp Gly Val Thr Gly Arg Val Glu Phe Asn Glu Asp Gly Asp Arg Lys
    315                 320                 325

TTC GCC AAC TAC AGC ATC ATG AAC CTG CAG AAC CGC AAG CTG GTG CAA    2187
Phe Ala Asn Tyr Ser Ile Met Asn Leu Gln Asn Arg Lys Leu Val Gln
330                 335                 340                 345

GTG GGC ATC TAC AAT GGC ACC CAC GTC ATC CCT AAT GAC AGG AAG ATC    2235
Val Gly Ile Tyr Asn Gly Thr His Val Ile Pro Asn Asp Arg Lys Ile
                350                 355                 360

ATC TGG CCA GGC GGA GAG ACA GAG AAG CCT CGA GGG TAC CAG ATG TCC    2283
Ile Trp Pro Gly Gly Glu Thr Glu Lys Pro Arg Gly Tyr Gln Met Ser
            365                 370                 375

ACC AGA CTG AAG ATT GTG ACG ATC CAC CAG GAG CCC TTC GTG TAC GTC    2331
Thr Arg Leu Lys Ile Val Thr Ile His Gln Glu Pro Phe Val Tyr Val
        380                 385                 390

AAG CCC ACG CTG AGT GAT GGG ACA TGC AAG GAG GAG TTC ACA GTC AAC    2379
Lys Pro Thr Leu Ser Asp Gly Thr Cys Lys Glu Glu Phe Thr Val Asn
395                 400                 405

GGC GAC CCA GTC AAG AAG GTG ATC TGC ACC GGG CCC AAC GAC ACG TCG    2427
Gly Asp Pro Val Lys Lys Val Ile Cys Thr Gly Pro Asn Asp Thr Ser
410                 415                 420                 425

CCG GGC AGC CCC CGC CAC ACG GTG CCT CAG TGT TGC TAC GGC TTT TGC    2475
Pro Gly Ser Pro Arg His Thr Val Pro Gln Cys Cys Tyr Gly Phe Cys
                430                 435                 440

ATC GAC CTG CTC ATC AAG CTG GCA CGG ACC ATG AAC TTC ACC TAC GAG    2523
Ile Asp Leu Leu Ile Lys Leu Ala Arg Thr Met Asn Phe Thr Tyr Glu
            445                 450                 455

GTG CAC CTG GTG GCA GAT GGC AAG TTC GGC ACA CAG GAG CGG GTG AAC    2571
Val His Leu Val Ala Asp Gly Lys Phe Gly Thr Gln Glu Arg Val Asn
        460                 465                 470

AAC AGC AAC AAG AAG GAG TGG AAT GGG ATG ATG GGC GAG CTG CTC AGC    2619
Asn Ser Asn Lys Lys Glu Trp Asn Gly Met Met Gly Glu Leu Leu Ser
475                 480                 485

GGG CAG GCA GAC ATG ATC GTG GCG CCG CTA ACC ATA AAC AAC GAG CGC    2667
Gly Gln Ala Asp Met Ile Val Ala Pro Leu Thr Ile Asn Asn Glu Arg
490                 495                 500                 505

GCG CAG TAC ATC GAG TTT TCC AAG CCC TTC AAG TAC CAG GGC CTG ACT    2715
Ala Gln Tyr Ile Glu Phe Ser Lys Pro Phe Lys Tyr Gln Gly Leu Thr
                510                 515                 520

ATT CTG GTC AAG AAG GAG ATT CCC CGG AGC ACG TTG GAC TCG TTC ATG    2763
Ile Leu Val Lys Lys Glu Ile Pro Arg Ser Thr Leu Asp Ser Phe Met
            525                 530                 535

CAG CCG TTC CAG AGC ACA CTG TGG CTG CTG GTG GGG CTG TCG GTG CAC    2811
Gln Pro Phe Gln Ser Thr Leu Trp Leu Leu Val Gly Leu Ser Val His
        540                 545                 550

GTG GTG GCC GTG ATG CTG TAC CTG CTG GAC CGC TTC AGC CCC TTC GGC    2859
```

-continued

```
                Val Val Ala Val Met Leu Tyr Leu Leu Asp Arg Phe Ser Pro Phe Gly
                                555                 560                 565

CGG TTC AAG GTG AAC AGC GAG GAG GAG GAG GAC GCA CTG ACC CTG                    2907
Arg Phe Lys Val Asn Ser Glu Glu Glu Glu Asp Ala Leu Thr Leu
570                 575                 580                 585

TCC TCG GCC ATG TGG TTC TCC TGG GGC GTC CTG CTC AAC TCC GGC ATC                2955
Ser Ser Ala Met Trp Phe Ser Trp Gly Val Leu Leu Asn Ser Gly Ile
                590                 595                 600

GGG GAA GGC GCC CCC AGA AGC TTC TCA GCG CGC ATC CTG GGC ATG GTG                3003
Gly Glu Gly Ala Pro Arg Ser Phe Ser Ala Arg Ile Leu Gly Met Val
                605                 610                 615

TGG GCC GGC TTT GCC ATG ATC ATC GTG GCC TCC TAC ACC GCC AAC CTG                3051
Trp Ala Gly Phe Ala Met Ile Ile Val Ala Ser Tyr Thr Ala Asn Leu
                620                 625                 630

GCG GCC TTC CTG GTG CTG GAC CGG CCG GAG GAG CGC ATC ACG GGC ATC                3099
Ala Ala Phe Leu Val Leu Asp Arg Pro Glu Glu Arg Ile Thr Gly Ile
                635                 640                 645

AAC GAC CCT CGG CTG AGG AAC CCC TCG GAC AAG TTT ATC TAC GCC ACG                3147
Asn Asp Pro Arg Leu Arg Asn Pro Ser Asp Lys Phe Ile Tyr Ala Thr
650                 655                 660                 665

GTG AAG CAG AGC TCC GTG GAT ATC TAC TTC CGG CGC CAG GTG GAG CTG                3195
Val Lys Gln Ser Ser Val Asp Ile Tyr Phe Arg Arg Gln Val Glu Leu
                670                 675                 680

AGC ACC ATG TAC CGG CAT ATG GAG AAG CAC AAC TAC GAG AGT GCG GCG                3243
Ser Thr Met Tyr Arg His Met Glu Lys His Asn Tyr Glu Ser Ala Ala
                685                 690                 695

GAG GCC ATC CAG GCC GTG AGA GAC AAC AAG CTG CAT GCC TTC ATC TGG                3291
Glu Ala Ile Gln Ala Val Arg Asp Asn Lys Leu His Ala Phe Ile Trp
                700                 705                 710

GAC TCG GCG GTG CTG GAG TTC GAG GCC TCG CAG AAG TGC GAC CTG GTG                3339
Asp Ser Ala Val Leu Glu Phe Glu Ala Ser Gln Lys Cys Asp Leu Val
715                 720                 725

ACG ACT GGA GAG CTG TTT TTC CGC TCG GGC TTC GGA ATA GGC ATG CGC                3387
Thr Thr Gly Glu Leu Phe Phe Arg Ser Gly Phe Gly Ile Gly Met Arg
730                 735                 740                 745

AAA GAC AGC CCC TGG AAG CAG AAC GTC TCC CTG TCC ATC CTC AAG TCC                3435
Lys Asp Ser Pro Trp Lys Gln Asn Val Ser Leu Ser Ile Leu Lys Ser
                750                 755                 760

CAC GAG AAT GGC TTC ATG GAA GAC CTG GAC AAG ACG TGG GTT CGG TAT                3483
His Glu Asn Gly Phe Met Glu Asp Leu Asp Lys Thr Trp Val Arg Tyr
                765                 770                 775

CAG GAA TGT GAC TCG CGC AGC AAC GCC CCT GCG ACC CTT ACT TTT GAG                3531
Gln Glu Cys Asp Ser Arg Ser Asn Ala Pro Ala Thr Leu Thr Phe Glu
                780                 785                 790

AAC ATG GCC GGG GTC TTC ATG CTG GTA GCT GGG GGC ATC GTG GCC GGG                3579
Asn Met Ala Gly Val Phe Met Leu Val Ala Gly Gly Ile Val Ala Gly
795                 800                 805

ATC TTC CTG ATT TTC ATC GAG ATT GCC TAC AAG CGG CAC AAG GAT GCT                3627
Ile Phe Leu Ile Phe Ile Glu Ile Ala Tyr Lys Arg His Lys Asp Ala
810                 815                 820                 825

CGC CGG AAG CAG ATG CAG CTG GCC TTT GCC GCC GTT AAC GTG TGG CGG                3675
Arg Arg Lys Gln Met Gln Leu Ala Phe Ala Ala Val Asn Val Trp Arg
                830                 835                 840

AAG AAC CTG CAG CAG TAC CAT CCC ACT GAT ATC ACG GGC CCG CTC AAC                3723
Lys Asn Leu Gln Gln Tyr His Pro Thr Asp Ile Thr Gly Pro Leu Asn
                845                 850                 855

CTC TCA GAT CCC TCG GTC AGC ACC GTG GTG TGAGGCCCCC GGAGGCGCCC                  3773
Leu Ser Asp Pro Ser Val Ser Thr Val Val
                860                 865
```

```
ACCTGCCCAG TTAGCCCGGC CAAGGACACT GATGGGTCCT GCTGCTCGGG AAGGCCTGAG    3833

GGAAGCCCAC CCGCCCCAGA GACTGCCCAC CCTGGGCCTC CCGTCCGTCC GCCCGCCCAC    3893

CCCGCTGCCT GGCGGGCAGC CCCTGCTGGA CCAAGGTGCG GACCGGAGCG GCTGAGGACG    3953

GGGCAGAGCT GAGTCGGCTG GCAGGGCGC  AGGGCGCTCC GGCAGAGGCA GGGCCCTGGG    4013

GTCTCTGAGC AGTGGGGAGC GGGGGCTAAC TGGCCCCAGG CGAAGGGGCT TGGAGCAGAG    4073

ACGGCAGCCC CATCCTTCCC GCAGCACCAG CCTGAGCCAC AGTGGGGCCC ATGGCCCCAG    4133

CTGGCTGGGT CGCCCCTCCT CGGGCGCCTG CGCTCCTCTG CAGCCTGAGC TCCACCCTCC    4193

CCTCTTCTTG CGGCACCGCC CACCCACACC CCGTCTGCCC CTTGACCCCA CACGCCGGGG    4253

CTGGCCCTGC CCTCCCCCAC GGCCGTCCCT GACTTCCCAG CTGGCAGCGC CTCCCGCCGC    4313

CTCGGGCCGC CTCCTCCAGA CTCGAGAGGG CTGAGCCCCT CCTCTCCTCG TCCGGCCTGC    4373

AGCCCAGAAC GGGCCTCCCC GGGGGTCCCC GGACGCTGGC TCGGGACTGT CTTCAACCCT    4433

GCCCTGCACC TTGGGCACGG GAGAGCGCCA CCCGCCCGCC CCCGCCCTCG CTCCGGGTGC    4493

GTGACCGGCC CGCCACCTTG TACAGAACCA GCACTCCCAG GGCCCGAGCG CGTGCCTTCC    4553

CCGTGCGGCC CGTGCGCAGC CGCGCTCTGC CCCTCCGTCC CCAGGGTGCA GGCGCGCACC    4613

GCCCAACCCC CACCTCCCGG TGTATGCAGT GGTGATGCCG GAATTC                  4659
```

(2) INFORMATION FOR SEQ ID NO:11:

(i) SEQUENCE CHARACTERISTICS:
        (A) LENGTH: 885 amino acids
        (B) TYPE: amino acid
        (D) TOPOLOGY: linear (ii) MOLECULE TYPE: protein (xi) SEQUENCE DESCRIPTION: SEQ ID NO:11:

```
Met Ser Thr Met Arg Leu Leu Thr Leu Ala Leu Leu Phe Ser Cys Ser
-18         -15                 -10                 -5

Val Ala Arg Ala Ala Cys Asp Pro Lys Ile Val Asn Ile Gly Ala Val
                1               5                   10

Leu Ser Thr Arg Lys His Glu Gln Met Phe Arg Glu Ala Val Asn Gln
    15              20                  25                  30

Ala Asn Lys Arg His Gly Ser Trp Lys Ile Gln Leu Asn Ala Thr Ser
                35                  40                  45

Val Thr His Lys Pro Asn Ala Ile Gln Met Ala Leu Ser Val Cys Glu
            50                  55                  60

Asp Leu Ile Ser Ser Gln Val Tyr Ala Ile Leu Val Ser His Pro Pro
            65                  70                  75

Thr Pro Asn Asp His Phe Thr Pro Thr Pro Val Ser Tyr Thr Ala Gly
    80                  85                  90

Phe Tyr Arg Ile Pro Val Leu Gly Leu Thr Thr Arg Met Ser Ile Tyr
95                  100                 105                 110

Ser Asp Lys Ser Ile His Leu Ser Phe Leu Arg Thr Val Pro Pro Tyr
                115                 120                 125

Ser His Gln Ser Ser Val Trp Phe Glu Met Met Arg Val Tyr Ser Trp
            130                 135                 140

Asn His Ile Ile Leu Leu Val Ser Asp Asp His Glu Gly Arg Ala Ala
            145                 150                 155

Gln Lys Arg Leu Glu Thr Leu Leu Glu Glu Arg Glu Ser Lys Ala Glu
    160                 165                 170

Lys Val Leu Gln Phe Asp Pro Gly Thr Lys Asn Val Thr Ala Leu Leu
```

```
                175                 180                 185                 190
Met Glu Ala Lys Glu Leu Glu Ala Arg Val Ile Ile Leu Ser Ala Ser
                    195                 200                 205

Glu Asp Ala Ala Thr Val Tyr Arg Ala Ala Met Leu Asn Met
            210                 215                 220

Thr Gly Ser Gly Tyr Val Trp Leu Val Gly Glu Arg Glu Ile Ser Gly
            225                 230                 235

Asn Ala Leu Arg Tyr Ala Pro Asp Gly Ile Leu Gly Leu Gln Leu Ile
            240                 245                 250

Asn Gly Lys Asn Glu Ser Ala His Ile Ser Asp Ala Val Gly Val Val
255                 260                 265                 270

Ala Gln Ala Val His Glu Leu Leu Glu Lys Glu Asn Ile Thr Asp Pro
                    275                 280                 285

Pro Arg Gly Cys Val Gly Asn Thr Asn Ile Trp Lys Thr Gly Pro Leu
                    290                 295                 300

Phe Lys Arg Val Leu Met Ser Ser Lys Tyr Ala Asp Gly Val Thr Gly
                    305                 310                 315

Arg Val Glu Phe Asn Glu Asp Gly Asp Arg Lys Phe Ala Asn Tyr Ser
            320                 325                 330

Ile Met Asn Leu Gln Asn Arg Lys Leu Val Gln Val Gly Ile Tyr Asn
335                 340                 345                 350

Gly Thr His Val Ile Pro Asn Asp Arg Lys Ile Ile Trp Pro Gly Gly
                    355                 360                 365

Glu Thr Glu Lys Pro Arg Gly Tyr Gln Met Ser Thr Arg Leu Lys Ile
                    370                 375                 380

Val Thr Ile His Gln Glu Pro Phe Val Tyr Val Lys Pro Thr Leu Ser
            385                 390                 395

Asp Gly Thr Cys Lys Glu Glu Phe Thr Val Asn Gly Asp Pro Val Lys
    400                 405                 410

Lys Val Ile Cys Thr Gly Pro Asn Asp Thr Ser Pro Gly Ser Pro Arg
415                 420                 425                 430

His Thr Val Pro Gln Cys Cys Tyr Gly Phe Cys Ile Asp Leu Leu Ile
                    435                 440                 445

Lys Leu Ala Arg Thr Met Asn Phe Thr Tyr Glu Val His Leu Val Ala
            450                 455                 460

Asp Gly Lys Phe Gly Thr Gln Glu Arg Val Asn Asn Ser Asn Lys Lys
            465                 470                 475

Glu Trp Asn Gly Met Met Gly Glu Leu Leu Ser Gly Gln Ala Asp Met
            480                 485                 490

Ile Val Ala Pro Leu Thr Ile Asn Asn Glu Arg Ala Gln Tyr Ile Glu
495                 500                 505                 510

Phe Ser Lys Pro Phe Lys Tyr Gln Gly Leu Thr Ile Leu Val Lys Lys
                    515                 520                 525

Glu Ile Pro Arg Ser Thr Leu Asp Ser Phe Met Gln Pro Phe Gln Ser
            530                 535                 540

Thr Leu Trp Leu Leu Val Gly Leu Ser Val His Val Ala Val Met
            545                 550                 555

Leu Tyr Leu Leu Asp Arg Phe Ser Pro Phe Gly Arg Phe Lys Val Asn
            560                 565                 570

Ser Glu Glu Glu Glu Asp Ala Leu Thr Leu Ser Ser Ala Met Trp
575                 580                 585                 590

Phe Ser Trp Gly Val Leu Leu Asn Ser Gly Ile Gly Glu Gly Ala Pro
                    595                 600                 605
```

```
Arg Ser Phe Ser Ala Arg Ile Leu Gly Met Val Trp Ala Gly Phe Ala
            610                 615                 620

Met Ile Ile Val Ala Ser Tyr Thr Ala Asn Leu Ala Ala Phe Leu Val
            625                 630                 635

Leu Asp Arg Pro Glu Glu Arg Ile Thr Gly Ile Asn Asp Pro Arg Leu
            640                 645                 650

Arg Asn Pro Ser Asp Lys Phe Ile Tyr Ala Thr Val Lys Gln Ser Ser
655                 660                 665                 670

Val Asp Ile Tyr Phe Arg Arg Gln Val Glu Leu Ser Thr Met Tyr Arg
            675                 680                 685

His Met Glu Lys His Asn Tyr Glu Ser Ala Ala Glu Ala Ile Gln Ala
            690                 695                 700

Val Arg Asp Asn Lys Leu His Ala Phe Ile Trp Asp Ser Ala Val Leu
            705                 710                 715

Glu Phe Glu Ala Ser Gln Lys Cys Asp Leu Val Thr Thr Gly Glu Leu
            720                 725                 730

Phe Phe Arg Ser Gly Phe Gly Ile Gly Met Arg Lys Asp Ser Pro Trp
735                 740                 745                 750

Lys Gln Asn Val Ser Leu Ser Ile Leu Lys Ser His Glu Asn Gly Phe
            755                 760                 765

Met Glu Asp Leu Asp Lys Thr Trp Val Arg Tyr Gln Glu Cys Asp Ser
            770                 775                 780

Arg Ser Asn Ala Pro Ala Thr Leu Thr Phe Glu Asn Met Ala Gly Val
            785                 790                 795

Phe Met Leu Val Ala Gly Gly Ile Val Ala Gly Ile Phe Leu Ile Phe
            800                 805                 810

Ile Glu Ile Ala Tyr Lys Arg His Lys Asp Ala Arg Arg Lys Gln Met
815                 820                 825                 830

Gln Leu Ala Phe Ala Ala Val Asn Val Trp Arg Lys Asn Leu Gln Gln
            835                 840                 845

Tyr His Pro Thr Asp Ile Thr Gly Pro Leu Asn Leu Ser Asp Pro Ser
            850                 855                 860

Val Ser Thr Val Val
        865

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (xi) SEQUENCE DESCRIPTION: SEQ ID NO:12:

GAAGAACCTG CAGCAGTACC ATCCCACT                                          28

(2) INFORMATION FOR SEQ ID NO:13:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (xi) SEQUENCE DESCRIPTION: SEQ ID NO:13:

GAAGAACCTG CAGAGCACCG GGGGTGGACG CGGCGCTTTG CAAAACCAAA AAGACACAGT        60

GCTGCCGCGA CGCGCTATTG AGAGGGAGGA GGGCCAGCTG CAGCTGTGTT CCCGTCATAG       120
```

| GGAGAGCTGA GACTCCCCGC CCGCCCTCCT CTGCCCCCTC CCCCGCAGAC AGACAGACAG | 180 |
| ACGGATGGGA CAGCGGCCCG GCCCACGCAG AGCCCCGGAG CACCACGGGG TCGGGGGAGG | 240 |
| AGCACCCCCA GCCTCCCCCA GGCTGCGCCT GCCCGCCCGC CGGTTGGCCG GCTGGCCGGT | 300 |
| CCACCCCGTC CCGGCCCCGC GCGTGCCCCC AGCGTGGGGC TAACGGGCGC CTTGTCTGTG | 360 |
| TATTTCTATT TTGCAGCAGT ACCATCCCAC T | 391 |

(2) INFORMATION FOR SEQ ID NO:14:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (xi) SEQUENCE DESCRIPTION: SEQ ID NO:14:

| GAAGAACCTG CAGGATAGAA AGAGTGGTAG AGCAGAGCCT GACCCTAAAA AGAAAGCCAC | 60 |
| ATTTAGGGCT ATCACCTCCA CCCTGGCTTC CAGCTTCAAG AGGCGTAGGT CCTCCAAAGA | 120 |
| CACGAGCACC GGGGGTGGAC GCGGCGCTTT GCAAAACCAA AAAGACACAG TGCTGCCGCG | 180 |
| ACGCGCTATT GAGAGGGAGG AGGGCCAGCT GCAGCTGTGT TCCCGTCATA GGGAGAGCTG | 240 |
| AGACTCCCCG CCCGCCCTCC TCTGCCCCCT CCCCCGCAGA CAGACAGACA GACGGATGGG | 300 |
| ACAGCGGCCC GGCCCACGCA GAGCCCCGGA GCACCACGGG GTCGGGGGAG GAGCACCCCC | 360 |
| AGCCTCCCCC AGGCTGCGCC TGCCCGCCCG CCGGTTGGCC GGCTGGCCGG TCCACCCCGT | 420 |
| CCCGGCCCCG CGCGTGCCCC CAGCGTGGGG CTAACGGGCG CCTTGTCTGT GTATTTCTAT | 480 |
| TTTGCAGCAG TACCATCCCA CT | 502 |

(2) INFORMATION FOR SEQ ID NO:15:

(i) SEQUENCE CHARACTERISTICS:
        (A) LENGTH: 1004 base pairs
        (B) TYPE: nucleic acid
        (C) STRANDEDNESS: double
        (D) TOPOLOGY: linear (xi) SEQUENCE DESCRIPTION: SEQ ID NO:15:

| GAAGAACCTG CAGGATAGAA AGAGTGGTAG AGCAGAGCCT GACCCTAAAA AGAAAGCCAC | 60 |
| ATTTAGGGCT ATCACCTCCA CCCTGGCTTC CAGCTTCAAG AGGCGTAGGT CCTCCAAAGA | 120 |
| CACGAGCACC GGGGGTGGAC GCGGCGCTTT GCAAAACCAA AAAGACACAG TGCTGCCGCG | 180 |
| ACGCGCTATT GAGAGGGAGG AGGGCCAGCT GCAGCTGTGT TCCCGTCATA CGGAGAGCTG | 240 |
| AGACTCCCCG CCCGCCCTCC TCTGCCCCCT CCCCCGCAGA CAGACAGACA GACGGATGGG | 300 |
| ACAGCGGCCC GGCCCACGCA GAGCCCCGGA GCACCACGGG GTCGGGGGAG GAGCACCCCC | 360 |
| AGCCTCCCCC AGGCTGCGCC TGCCCGCCCG CCGGTTGGCC GGCTGGCCGG TCCACCCCGT | 420 |
| CCCGGCCCCG CGCGTGCCCC CAGCGTGGGG CTAACGGGCG CCTTGTCTGT GTATTTCTAT | 480 |
| TTTGCAGCAG TACCATCCCA CTGAAGAACC TGCAGGATAG AAAGAGTGGT AGAGCAGAGC | 540 |
| CTGACCCTAA AAAGAAAGCC ACATTTAGGG CTATCACCTC CACCCTGGCT TCCAGCTTCA | 600 |
| AGAGGCGTAG GTCCTCCAAA GACACGAGCA CCGGGGGTGG ACGCGGCGCT TTGCAAAACC | 660 |
| AAAAAGACAC AGTGCTGCCG CGACGCGCTA TTGAGAGGGA GGAGGGCCAG CTGCAGCTGT | 720 |
| GTTCCCGTCA TAGGGAGAGC TGAGACTCCC CGCCCGCCCT CCTCTGCCCC CTCCCCCGCA | 780 |
| GACAGACAGA CAGACGGATG GGACAGCGGC CCGGCCCACG CAGAGCCCCG GAGCACCACG | 840 |

```
GGGTCGGGGG AGGAGCACCC CCAGCCTCCC CCAGGCTGCG CCTGCCCGCC CGCCGGTTGG      900

CCGGCTGGCC GGTCCACCCC GTCCCGGCCC CGCGCGTGCC CCAGCGTGG GGCTAACGGG       960

CGCCTTGTCT GTGTATTTCT ATTTTGCAGC AGTACCATCC CACT                      1004
```

(2) INFORMATION FOR SEQ ID NO:16:

(i) SEQUENCE CHARACTERISTICS:
        (A) LENGTH: 65 amino acids
        (B) TYPE: amino acid
        (D) TOPOLOGY: linear (xi) SEQUENCE DESCRIPTION: SEQ ID NO:16:

```
Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
                20                  25                  30

Ala Ala Val Asn Val Trp Arg Lys Asn Leu Gln Gln Tyr His Pro Thr
            35                  40                  45

Asp Ile Thr Gly Pro Leu Asn Leu Ser Asp Pro Ser Val Ser Thr Val
        50                  55                  60

Val
65
```

(2) INFORMATION FOR SEQ ID NO:17:

(i) SEQUENCE CHARACTERISTICS:
        (A) LENGTH: 102 amino acids
        (B) TYPE: amino acid
        (D) TOPOLOGY: linear (xi) SEQUENCE DESCRIPTION: SEQ ID NO:17:

```
Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
                20                  25                  30

Ala Ala Val Asn Val Trp Arg Lys Asn Leu Gln Asp Arg Lys Ser Gly
            35                  40                  45

Arg Ala Glu Pro Asp Pro Lys Lys Lys Ala Thr Phe Arg Ala Ile Thr
        50                  55                  60

Ser Thr Leu Ala Ser Ser Phe Lys Arg Arg Ser Ser Lys Asp Thr
65                  70                  75                  80

Gln Tyr His Pro Thr Asp Ile Thr Gly Pro Leu Asn Leu Ser Asp Pro
                85                  90                  95

Ser Val Ser Thr Val Val
            100
```

(2) INFORMATION FOR SEQ ID NO:18:

(i) SEQUENCE CHARACTERISTICS:
        (A) LENGTH: 26 amino acids
        (B) TYPE: amino acid
        (D) TOPOLOGY: linear (xi) SEQUENCE DESCRIPTION: SEQ ID NO:18:

```
Lys Arg Leu Glu Thr Leu Leu Glu Glu Arg Glu Ser Lys Ala Glu Lys
1               5                   10                  15

Val Leu Gln Phe Asp Pro Gly Thr Lys Asn
                20                  25
```

-continued (2) INFORMATION FOR SEQ ID NO:19:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION: SEQ ID NO:19:

Lys Arg Leu Glu Thr Leu Leu Glu Glu Arg Glu Ser Lys Ser Lys Lys
1               5                   10                  15

Arg Asn Tyr Glu Asn Leu Asp Gln Leu Ser Tyr Asp Asn Lys Arg Gly
            20                  25                  30

Pro Lys Ala Glu Lys Val Leu Gln Phe Asp Pro Gly Thr Lys Asn
        35                  40                  45

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

GGGGTTTAGA TCTGGGTNAT GATGTTYGTN ATG                                33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:21:

GGGGTTTAGA TCTGCNGCRT CRTADATRAA NGC                                33

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:22:

GGGGTTTGGA TCCAARGART GGAAYGGNAT GATG                               34

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:23:

GGGGTTTAAG CTTYTCRTAR TTRTGYTTYT CCAT                               34